US009827243B2

(12) United States Patent
Kreilein et al.

(10) Patent No.: US 9,827,243 B2
(45) Date of Patent: *Nov. 28, 2017

(54) PHARMACEUTICAL FORMULATIONS, PROCESSES, SOLID FORMS AND METHODS OF USE RELATING TO 1-ETHYL-7-(2-METHYL-6-(1H-1,2,4-TRIAZOL-3-YL)PYRIDIN-3-YL)-3,4-DIHYDROPYRAZINO[2,3-B]PYRAZIN-2(1H)-ONE

(71) Applicant: SIGNAL PHARMACEUTICALS, LLC, San Diego, CA (US)

(72) Inventors: Matthew Michael Kreilein, Hillsborough, NJ (US); Thomas Lee, Bedminster, NJ (US); Ying Li, Millburn, NJ (US); Jean Xu, Warren, NJ (US); William Wei-Hwa Leong, Westfield, NJ (US); Benjamin Cohen, Cranford, NJ (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/150,577

(22) Filed: May 10, 2016

(65) Prior Publication Data

US 2016/0250210 A1 Sep. 1, 2016

Related U.S. Application Data

(63) Continuation of application No. 14/254,023, filed on Apr. 16, 2014, now Pat. No. 9,359,364.

(60) Provisional application No. 61/911,201, filed on Dec. 3, 2013, provisional application No. 61/813,064, filed on Apr. 17, 2013.

(51) Int. Cl.
| | | |
|---|---|---|
| *C07D 487/04* | (2006.01) | |
| *A61K 31/4985* | (2006.01) | |
| *C07D 471/04* | (2006.01) | |
| *A61K 9/20* | (2006.01) | |
| *A61K 9/48* | (2006.01) | |

(52) U.S. Cl.
CPC ........ *A61K 31/4985* (2013.01); *A61K 9/2018* (2013.01); *A61K 9/2054* (2013.01); *A61K 9/4858* (2013.01); *C07D 471/04* (2013.01); *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 3,507,866 A | 4/1970 | Jones et al. | |
| 3,567,725 A | 3/1971 | Grabowski et al. | |
| 4,294,836 A | 10/1981 | Lesher et al. | |
| 4,294,837 A | 10/1981 | Lesher et al. | |
| 4,309,537 A | 1/1982 | Lesher et al. | |
| 4,317,909 A | 3/1982 | Lesher et al. | |
| 4,898,872 A | 2/1990 | Campbell et al. | |
| 4,963,561 A | 10/1990 | Lesher et al. | |
| 5,424,311 A | 6/1995 | Billhardt-Troughton | |
| 5,869,659 A | 2/1999 | Stolle et al. | |
| 6,031,105 A | 2/2000 | Wright | |
| 6,093,728 A | 7/2000 | McMahon et al. | |
| 6,372,740 B1 | 4/2002 | Murata et al. | |
| 6,566,367 B2 | 5/2003 | Bakthavatchalam et al. | |
| 6,791,006 B2 | 9/2004 | Nezu et al. | |
| 6,800,436 B1 | 10/2004 | Jenne et al. | |
| 6,825,184 B2 | 11/2004 | Ciriillo et al. | |
| 6,855,723 B2 | 2/2005 | McMahon et al. | |
| 7,199,119 B2 | 4/2007 | Burkitt et al. | |
| 7,247,621 B2 | 7/2007 | Hong et al. | |
| 7,429,572 B2 | 9/2008 | Clark | |
| 7,476,665 B2 | 1/2009 | Burgey | |
| 7,608,622 B2 | 10/2009 | Liu et al. | |
| 7,700,594 B2 | 4/2010 | Chen et al. | |
| 7,767,687 B2 | 8/2010 | Oslob et al. | |
| 7,902,187 B2 | 3/2011 | Neagu et al. | |
| 7,919,490 B2 | 4/2011 | Neagu et al. | |
| 7,968,556 B2 | 6/2011 | Mortensen et al. | |
| 7,981,893 B2 | 7/2011 | Mortensen et al. | |
| 8,110,578 B2 * | 2/2012 | Perrin-Ninkovic | C07D 487/04 514/252.11 |
| 8,268,809 B2 | 9/2012 | Kalman | |
| 8,372,976 B2 | 2/2013 | Mortensen et al. | |
| 8,383,634 B2 | 2/2013 | Mortensen et al. | |
| 8,492,381 B2 | 7/2013 | Perrin-Ninkovic et al. | |
| 8,507,492 B2 * | 8/2013 | Perrin-Ninkovic | C07D 487/04 514/252.11 |
| 8,569,494 B2 | 10/2013 | Harris et al. | |
| 8,642,660 B2 | 2/2014 | Goldfard | |
| 8,686,135 B2 | 4/2014 | Jokiel | |
| 9,079,900 B2 | 7/2015 | Harris | |
| 9,155,736 B2 | 10/2015 | Xu et al. | |
| 9,359,364 B2 * | 6/2016 | Menon | A61K 31/4985 |

(Continued)

FOREIGN PATENT DOCUMENTS

| | | |
|---|---|---|
| CA | 2 458 699 | 3/2003 |
| DE | 262 026 | 11/1988 |

(Continued)

OTHER PUBLICATIONS

Background Information for the October ACPS Meeting, FDA, 2002.*

(Continued)

*Primary Examiner* — Matthew Coughlin

(74) *Attorney, Agent, or Firm* — Jones Day

(57) ABSTRACT

Provided herein are formulations, processes, solid forms and methods of use relating to 1-ethyl-7-(2-methyl-6-(1H-1,2,4-triazol-3-yl)pyridin-3-yl)-3,4-dihydropyrazino[2,3-b]pyrazin-2(1H)-one.

17 Claims, 41 Drawing Sheets

(56) References Cited

U.S. PATENT DOCUMENTS

| | | | |
|---|---|---|---|
| 9,416,134 B2* | 8/2016 | Eckert | C07D 487/04 |
| 9,474,757 B2* | 10/2016 | Hege | A61K 39/3955 |
| 9,505,764 B2* | 11/2016 | Raymon | C07D 487/04 |
| 9,512,129 B2* | 12/2016 | Eckert | C07D 487/04 |
| 2004/0063658 A1 | 4/2004 | Roberts et al. | |
| 2006/0004014 A1 | 1/2006 | Hoffmann et al. | |
| 2006/0142269 A1 | 6/2006 | Dykes | |
| 2007/0036793 A1 | 2/2007 | Hardie et al. | |
| 2008/0194019 A1 | 8/2008 | Cantley et al. | |
| 2009/0181963 A1 | 7/2009 | Dehnhardt et al. | |
| 2009/0186929 A1* | 7/2009 | Weinberg | A61K 31/155 514/396 |
| 2009/0281075 A1 | 11/2009 | Roughton et al. | |
| 2010/0144738 A1 | 6/2010 | Bornmann et al. | |
| 2010/0216781 A1* | 8/2010 | Perrin-Ninkovic | C07D 487/04 514/230.2 |
| 2010/0324112 A1* | 12/2010 | Gollin | G01N 33/5091 514/44 A |
| 2011/0257167 A1 | 10/2011 | Chopra et al. | |
| 2011/0318336 A1 | 12/2011 | Petricoin, III et al. | |
| 2012/0028972 A1 | 2/2012 | Wong et al. | |
| 2012/0238562 A1* | 9/2012 | Cinar | A61K 31/436 514/232.5 |
| 2013/0102613 A1 | 4/2013 | Xu et al. | |
| 2013/0142873 A1 | 6/2013 | Assaf et al. | |
| 2013/0158023 A1 | 6/2013 | Ning et al. | |
| 2013/0225518 A1 | 8/2013 | Xu et al. | |
| 2013/0245026 A1 | 9/2013 | Xu et al. | |
| 2013/0245027 A1 | 9/2013 | Xu et al. | |
| 2013/0245028 A1 | 9/2013 | Xu et al. | |
| 2013/0245029 A1 | 9/2013 | Xu et al. | |
| 2014/0314673 A1 | 10/2014 | Raymon et al. | |
| 2014/0314674 A1 | 10/2014 | Raymon et al. | |
| 2014/0314751 A1 | 10/2014 | Hege et al. | |
| 2014/0314752 A1 | 10/2014 | Lopez-Girona et al. | |
| 2014/0315848 A1 | 10/2014 | Raymon | |
| 2014/0315900 A1 | 10/2014 | Raymon et al. | |
| 2014/0315907 A1 | 10/2014 | Raymon et al. | |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 99/16438 | 4/1999 |
| WO | WO 99/28320 | 6/1999 |
| WO | WO 99/28459 | 6/1999 |
| WO | WO 00/73306 | 12/2000 |
| WO | WO 02/48152 | 6/2002 |
| WO | WO 02/076954 | 10/2002 |
| WO | WO 03/032989 | 4/2003 |
| WO | WO 03/072557 | 9/2003 |
| WO | WO 03/093290 | 11/2003 |
| WO | WO 2004/042002 | 5/2004 |
| WO | WO 2004/048365 | 6/2004 |
| WO | WO 2004/065378 | 8/2004 |
| WO | WO 2004/076454 | 9/2004 |
| WO | WO 2004/078754 | 9/2004 |
| WO | WO 2004/085409 | 10/2004 |
| WO | WO 2004/096797 | 11/2004 |
| WO | WO 2005/003147 | 1/2005 |
| WO | WO 2005/021519 | 3/2005 |
| WO | WO 2005/120511 | 12/2005 |
| WO | WO 2006/001266 | 1/2006 |
| WO | WO 2006/018182 | 2/2006 |
| WO | WO 2006/030031 | 3/2006 |
| WO | WO 2006/036883 | 4/2006 |
| WO | WO 2006/045828 | 5/2006 |
| WO | WO 2006/046031 | 5/2006 |
| WO | WO 2006/050076 | 5/2006 |
| WO | WO 2006/065703 | 6/2006 |
| WO | WO 2006/087530 | 8/2006 |
| WO | WO 2006/090167 | 8/2006 |
| WO | WO 2006/090169 | 8/2006 |
| WO | WO 2006/091737 | 8/2006 |
| WO | WO 2006/108103 | 10/2006 |
| WO | WO 2007/044698 | 4/2007 |
| WO | WO 2007/044729 | 4/2007 |
| WO | WO 2007/044813 | 4/2007 |
| WO | WO 2007/047754 | 4/2007 |
| WO | WO 2007/060404 | 5/2007 |
| WO | WO 2007/066099 | 6/2007 |
| WO | WO 2007/066102 | 6/2007 |
| WO | WO 2007/080382 | 7/2007 |
| WO | WO 2007/125321 | 11/2007 |
| WO | WO 2007/129044 | 11/2007 |
| WO | WO 2007/129052 | 11/2007 |
| WO | WO 2007/129161 | 11/2007 |
| WO | WO 2007/135398 | 11/2007 |
| WO | WO 2008/016669 | 2/2008 |
| WO | WO 2008/023161 | 2/2008 |
| WO | WO 2008/032027 | 3/2008 |
| WO | WO 2008/032028 | 3/2008 |
| WO | WO 2008/032033 | 3/2008 |
| WO | WO 2008/032036 | 3/2008 |
| WO | WO 2008/032060 | 3/2008 |
| WO | WO 2008/032064 | 3/2008 |
| WO | WO 2008/032072 | 3/2008 |
| WO | WO 2008/032077 | 3/2008 |
| WO | WO 2008/032089 | 3/2008 |
| WO | WO 2008/032091 | 3/2008 |
| WO | WO 2008/051493 | 5/2008 |
| WO | WO 2008/064093 | 5/2008 |
| WO | WO 2008/115974 | 9/2008 |
| WO | WO 2008/140947 | 11/2008 |
| WO | WO 2009/007748 | 1/2009 |
| WO | WO 2009/007750 | 1/2009 |
| WO | WO 2009/007751 | 1/2009 |
| WO | WO 2009/052145 | 4/2009 |
| WO | WO 2009/102986 | 8/2009 |
| WO | WO 2010/006072 | 1/2010 |
| WO | WO 2010/062571 | 6/2010 |
| WO | WO 2010/068483 | 6/2010 |
| WO | WO 2011/031965 | 3/2011 |
| WO | WO 2011/053518 A1 | 5/2011 |
| WO | WO 2011/079114 | 6/2011 |
| WO | WO 2011/097333 | 8/2011 |

OTHER PUBLICATIONS

B. Rodriquez-Spong et al. Advanced Drug Delivery Reviews, 2004, 56, pp. 241-274.*
Albert et al. Cancer Genomics & Proteomics 2009, 6, 255-262.*
Park et al. Transitional Oncology 2012, 5, 393-397.*
Nguyen et al. Current Treatment Options in Oncology 2012, 13, 71-81.*
Kunderfranco et al. PLoS One, 2010, 5, e10547, pp. 1-17.*
Subbiah et al. Discov. Med. 2012, 13, 405-415.*
McKinsey et al. Oncogene 2011, 30, 4910-4920.*
Zent et al. Cancer. 2010, 116, 2201-2207.*
Barlin 1982, "Purine analogs as amplifiers of phleomycin. VII. Some 1H-inidazo[4,5-b]pyrazines and related compound," Australian Journal of Chemistry, vol. 35:2299-2306.
Beresnev et al., 2000, "Interaction of 5-methoxy-1,2,4-traizines with uras as a new route to 6-azapurines," Medeleev Commu., vol. 2:58-59.
Bergmann et al., 1963, "2-Phenylpurines, their chemical and enzumological reactivity," J. Chem Org. , pp. 3729-3735.
Booth et al., 1992, "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemistry, vol. 2119-26.
Booth et al., 1995, "Synthesis of [1α, 2β,3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-675.
Booth et al., 2001, "The Reactions of Diaminomaleonitrile with Isocyanates and Either Aldehydes or Ketones Revisited," J. Org Chem, vol. 66:8436-8441.

(56) References Cited

OTHER PUBLICATIONS

Booth, et al., 1994, "Synthesis of 4- and 5-Disubstituted 1-Benzylimidazoles, Important Precursors of Purine Analogs," J. of Heterocyclic of Chemistry, vol. 31(2):345-50.
Caira et al., 1998, "Crystalline Polymorphism of Organic Compounds," Topics in Current Chemistry, Jan. 1, 1998, pp. 163-208, vol. 198, Springer, Berlin, DE.
Carretero et al. 2010, "Integrative Genomic and Proteomic Analyses Indentity Targets for Lkb1-Deficient Metastatic Lung Tumors," Cancer Cell, vol. 17(6): 547-559.
Chupakhin et al., 2001, "A simple one pot synthesis of condensed 1,2,4-triazines by using the tandem $A_N$-$S_N$ipso and $S_N^H$—$S_N$ipso reactions," J. of Heterocyclic Chemistry, vol. 38(4):901-907.
Cohen, 2005, *Protein Kinase Inhibitors for the Treatment of Disease: The Promise and the Problems*, Handbook of Experimental Pharmacology, Springer Berlin Heidelberg, 167:1-7.
Cohen, P. 2001, "The role of protein phosphorylation in human health and disease," Eur. J. Biochem,vol. 268:5001-5010.
Cohen, P. 2002, "Protein kinases—the major drug targets of the twenty-first century?" Nature Reviews/Drug Discovery, vol. 1:309-315.
Coish, et al., 2006, "Small molecule inhibitors of IKK kinase activity," Expert Opin. Ther. Patents, vol. 16(1):1-12.
Crofts et al., 1997 "Metabolism of 2-amino-1-methyl-6-phenylimidazo [4,5-b]pyridine (PhIP) by human cytochrome P4501B1," Carcinogenesis, vol. 18(9):1793-1798.
Dang et al., 1999, "Efficient synthesis of purines and purine nucelosides via an inverse electron demand diels-alder reaction," J. Am Chem Soc., vol. 121(24):5833-5834.
Database CAPLUS Online Chemical Abstracts Service, Columbus, Ohio, Database Accession No. 1951:49974 (XP-002472261) (1951).
Database CAPLUS Online Chemical Abstracts Service, Columbus, Ohio, Database Accession No. 1966:26849 (XP-002472263) (1965).
Database CAPLUS Online Chemical Abstracts Service, Columbus, Ohio, Database Accession No. 1978:433195 (XP-002472262) (1978).
Dornow et al., 1957, "Synthese von2-Oxy-imidazolo-(5',4':2,3)-pyridinen)," Arch Pharm. vol. 290, pp. 20-31 (w/English language abstract).
Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47, pp. 5783-5790.
Fabbro et al., 2002, "Protein kinases as targets for anticancer agents: from inhibitors to useful drugs," Pharmacol Ther., 93(2-3):79-98.
Farhadi et al., 2006, "The role of protein kinase C isoforms in modulating injury and repair of the intestinal barrier," J. Pharm Exp. Ther., vol. 316(1):1-7.
Frandsen et al., 1992, "Reaction of the N2-acetoxy derivative of 2-amino-1-methyl-6-phenylimidazo[4,5,b]pyridine . . . ," Carcinogenesis, vol. 13(4):629-635.
Furniss et al., 1989, "Vogel's Textbook of Practical Organic Chemistry Fifth Edition," 1989, p. 132-136, Longman.
Gao et al., 2010, "LKB1 inhibits lung cancer progression through lysyl oxidase and extracellular matrix remodeling," Proceedings of the National Academy of Sciences, vol. 107(44): 18892-18897.
Gao et al.: 2011, "LKB1 in lung cancerigenesis: a serine/threonine kinase as tumor suppressor," Protein & Cell, Gaodeng Jiaoyu Chubanshe, China, vol. 2(2): 99-107.
Georgakis and Younes, 2006, "From rapi nui to rapamycin: targeting PI3K/Akt/mTOR for cancer therapy," Expert Rev. Anticancer Ther., vol. 6(1):131-140.
Gini et al., 2013, "The mTOR Kinase Inhibitors, CC214-1 and CC214-2, Preferentially Block the Growth of EGFRvIII-Activated Glioblastomas," Clin Cancer Res 2013;19:5722-5732.
Grimmiger et al., 2010, "Targeting non-malignant disorders with tyrosine kinase inhibitors," Nat. Rev. Drug Disc., 9(12):956-970.
Hamad, 2001, "A new synthesis of 4-cyano-1,3-dihydro-2-oxo-2H-imidazole-5-($N^1$-tosyl)carboxamide: Reactive precursor for thiopurine analogues," J of Heterocyclic Chemistry, vol. 38(4):939-944.
Hernan et al., "De novo germline mutation in the serine-threonine kinase STK11/LKB1 gene associated with Peutz-Jeghers syndrome," Clin Genet., 66(1):58-62, 2004.
Huang et al., 2010, "Genetic and epigenetic silencing of SCARA5 may contribute to human hepatocellular carcinoma by activating FAK signaling," Journal of Clinical Investigation, American Society for Clinical investigation, vol. 120(1): 223-241.
Inge et al., 2009, "Expression of LKB1 tumor suppressor in non-small cell lung cancer determines sensitivity to 2-deoxyglucose," Journal of Thoracic and Cardiovascular Surgery, vol. 137(3): 580-586.
Irie et al., 2005, "Toward the development of new medicinal leads with selectivity for protein kinase C isozymes," The Chemical Record, vol. 5:185-195.
Itoh et al., 2004, "A novel practical synthesis of C-2-arylpurines," Advanced Synthesis & Catalysis, vol. 346:1859-1867.
Ji et al., 2007, "LKB1 modulates lung cancer differentiation and metastasis," Nature, 448(7155):807-810.
Jones et al., 1973, "6-Substituted-5-chloro-1,3-dihydro-2H-imidazo(4,5-b)pyrazin-2-ones with hypotensive activity," J. Med. Chem., vol. 16(5):537-542.
Kazaoka et al., 2003, "Synthesis of 6-substituted 9-benzyl-8-hydroxypurines with potential interferon-indcuing activity," Chemical & Pharmaceutical Bulletin, vol. 51(5):608-611.
Killday et al., 2001, "Microxine, a new cdc2 kinase inhibitor from the Australian marine sponge Microxina species," J. of Natural Products, vol. 64(4):525-526.
Mahoney et al., 2009, "LKB1/KRAS mutant lung cancers constitute a genetic subset of NSCLC with increased sensitivity to MAPK and mTOR signalling inhibition," Br J Cancer, 100(2):370-375.
Minehan et al., 2000, "Molecular recognition of DNA by Hoechst Benzimidazoles: Exploring beyond theopyrrole-imidazole-hydroxypyrrole polyamide-pairing code," Helvitica Chima Acta, vol. 83(9):2197-2213.
Nagashima et al., 2004, "Solution-Phase parallel synthesis of an N-Alkylated dihydropteridinone library from fluorous amino acids," J of Comb. Chemistry, vol. 6(6):942-949.
Park et al., 2000, "A novel mechanism of TRAF signaling revealed by structural and functional analyses of the TRADD-TRAF2 interaction," Cell, vol. 101:777-787.
Patani et al., 1998, "Bioisosterim: A rational approach in drug design," Chemical Reviews, vol. 96:3147-3176.
PCT Annex to Form PCT/ISA?206 Communication Relating to the Results of the Partial International Search issued in connection with PCT/US2012/049281,filed Aug. 2, 2012.
PCT International Search Report issued in connection with PCT/US2012/049281, filed Aug. 2, 2012.
PCT Written Opinion of the International Searching Authority issued in connection with PCT/US2012/049281, filed Aug. 2, 2012.
Registry File Document for RN 863501-03-5, 863502-39-0 and others (Sep. 20, 2005).
Seela et al., 2004, "Product Class 17: Purines," Science of Synthesis, vol. 16, pp. 945-1108.
Shaw et al., 2004, "The LKB1 tumor suppressor negativiely regulates mTOR signaling," Cancer Cell, vol. 6(1):91-99.
Shaw et al., 2009, "LKB1 and AMP-activated protein kinase control of mTOR signalling and growth," Acta. Physiol (Oxf.) 196(1):65-80.
Shoji et al. 2012, "Genotype-dependent efficacy of a dual PI3K/mTOR inhibitor, NVP-BEZ235, and an mTOR inhibitor, RAD001, in endometrial carcinomas." *PloS one* 7.5, 2012, e37431.
Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem., vol. 37(2):248-54.
Sridhar et al., 2000, "Protein kinases as therapeutic targets," Pharm. Res., 17(11):1345-1353.
Wallace 2008, "Palladium-catalyzed synthesis of quinoxaline derivatives," Tetrahedron, vol. 64:9675-9684.

(56) References Cited

OTHER PUBLICATIONS

Wei et al., 2009, "Chemopreventive efficacy of rapamycin on Peutz-Jeghers syndrome in a mouse model," Cancer Lett., 277(2):149-154.

Westover et al., 1981, "Synthesis and antiviral activity of certain 9-β-D-Riofuranoaylpurine-6-carboxamides," J.Med. Chem., vol. 24(8):941-46.

Wingo et al., 2009, "Somatic LKB1 mutations promote cervical cancer progression," PloS One, 4(4):1-8.

Yoneda et al., 1976, "A transformationof 7-azapteridines into 6-azapurines (Imidazo[4,5-e]-as-triazines)," Heterocycles, vol. 4(9):1503-1508.

Yoneda et al., 1978, "Synthesis of imadazo[4,5-e]-as-triazine (6-Azapurine) Deriviatives," Chem & Pharm Bulletin, vol. 26(10):3154-3160.

Yuan et al., 2009, "Targeting tumorigenesis: development and use of mTOR inhibitors in cancer therapy," Journal of Hematology & Oncology, Biomed Central Ltd., London UK, vol. 2(1): 45.

Zaki et al., 2007, "The synthesis of imidazol[4,5-d]pyridines from a substituted imidazole and acyl or sulfonyl acetonitrile," Tetrahedron, vol. 63(18):3745-3753.

Zhong et al., 2006, "LKB1 mutation in large cell carcinoma of the lung," Cancer Lung, vol. 53(3):285-294.

\* cited by examiner (70% major tautomer)

(30% minor tautomer)

PHARMACEUTICAL FORMULATIONS, PROCESSES, SOLID FORMS AND METHODS OF USE RELATING TO 1-ETHYL-7-(2-METHYL-6-(1H-1,2,4-TRIAZOL-3-YL)PYRIDIN-3-YL)-3,4-DIHYDROPYRAZINO[2,3-B]PYRAZIN-2(1H)-ONE

This application is a continuation of U.S. Non-Provisional application Ser. No. 14/254,023, filed Apr. 16, 2014, currently allowed, which claims the benefit of U.S. Provisional Application No. 61/813,064, filed Apr. 17, 2013 and U.S. Provisional Application No. 61/911,201, filed Dec. 3, 2013, the entire contents of which are incorporated herein by reference.

1. FIELD

Provided herein are formulations, processes, solid forms and methods of use relating to 1-ethyl-7-(2-methyl-6-(1H-1,2,4-triazol-3-yl)pyridin-3-yl)-3,4-dihydropyrazino[2,3]pyrazin-2(1H)-one.

2. BACKGROUND

The connection between abnormal protein phosphorylation and the cause or consequence of diseases has been known for over 20 years. Accordingly, protein kinases have become a very important group of drug targets. See Cohen, *Nat. Rev. Drug Discov.* 1(4):309-15 (2002). Various protein kinase inhibitors have been used clinically in the treatment of a wide variety of diseases, such as cancer and chronic inflammatory diseases, including diabetes and stroke. See Cohen, *Eur. J. Biochem.*, 268:5001-5010 (2001).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

The protein named mTOR (mammalian target of rapamycin), which is also called FRAP, RAFTI or RAPT1), is a 2549-amino acid Ser/Thr protein kinase, that has been shown to be one of the most critical proteins in the mTOR/PI3K/Akt pathway that regulates cell growth and proliferation. Georgakis and Younes *Expert Rev. Anticancer Ther.* 6(1):131-140 (2006). mTOR exists within two complexes, mTORC1 and mTORC2. mTORC1 is sensitive to rapamycin analogs (such as temsirolimus or everolimus) and mTORC2 is largely rapamycin-insensitive. Several mTOR inhibitors have been or are being evaluated in clinical trials for the treatment of cancer. Temsirolimus was approved for use in renal cell carcinoma in 2007 and everolimus was approved in 2009 for renal cell carcinoma patients that have progressed on vascular endothelial growth factor receptor inhibitors. In addition, sirolimus was approved in 1999 for the prophylaxis of renal transplant rejection. The interesting but limited clinical success of these mTORC1 compounds demonstrates the usefulness of mTOR inhibitors in the treatment of cancer and transplant rejection, and the increased potential for compounds with both mTORC1 and mTORC2 inhibitory activity.

Citation or identification of any reference in Section 2 of this application is not to be construed as an admission that the reference is prior art to the present application.

3. SUMMARY

Provided herein are methods of preparing Compound 1:

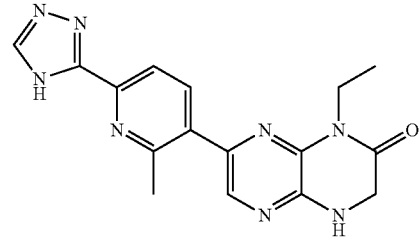

having the name 1-ethyl-7-(2-methyl-6-(1H-1,2,4-triazol-3-yl)pyridin-3-yl)-3,4-dihydropyrazino[2,3-b]pyrazin-2(1H)-one, or a tautomer thereof, for example, 1-ethyl-7-(2-methyl-6-(4H-1,2,4-triazol-3-yl)pyridin-3-yl)-3,4-dihydropyrazino[2,3-b]pyrazin-2(1H)-one, or 1-ethyl-7-(2-methyl-6-(1H-1,2,4-triazol-5-yl)pyridin-3-yl)-3,4-dihydropyrazino[2,3-b]pyrazin-2(1H)-one, and pharmaceutically acceptable salts, isotopologues, metabolites and stereoisomers thereof.

Also provided herein are solid forms of Compound 1 or a pharmaceutical salt thereof.

Also provided herein are formulations of Compound 1 and pharmaceutically acceptable salts, tautomers, isotopologues, metabolites and stereoisomers thereof.

In certain embodiments, Compound 1 and pharmaceutically acceptable salts, tautomers, isotopologues, metabolites, solid forms and stereoisomers thereof are useful for treating or preventing cancer and conditions treatable or preventable by inhibition of a kinase pathway, for example, the mTOR/PI3K/Akt pathway.

The present embodiments can be understood more fully by reference to the detailed description and examples, which are intended to exemplify non-limiting embodiments.

4. BRIEF DESCRIPTION OF THE DRAWINGS

5. DETAILED DESCRIPTION

5.1 Definitions

Figure 1:
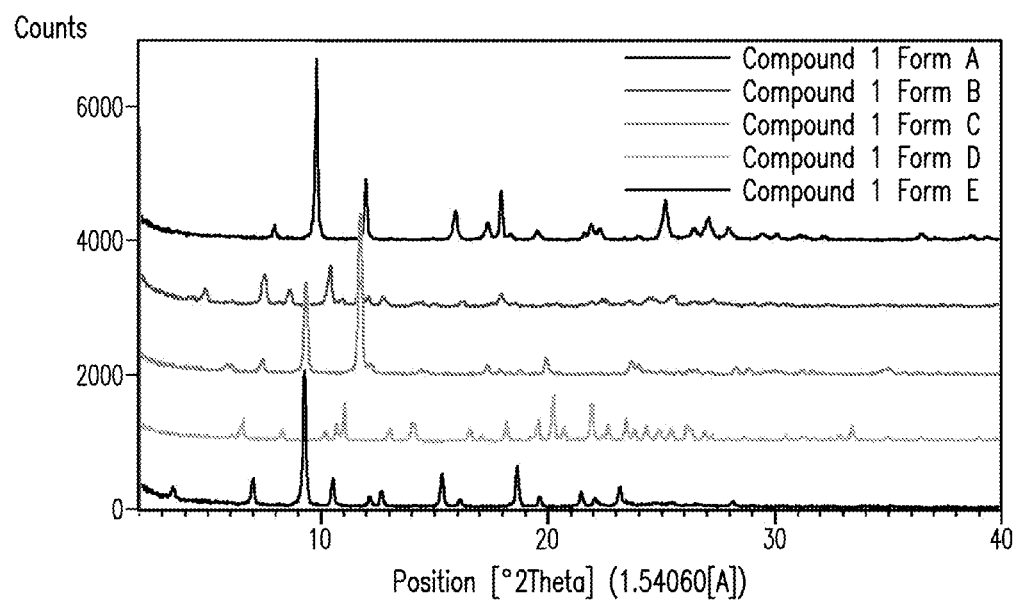
FIG. 1 depicts an X-ray powder diffractogram Stack Plot of Forms of Compound 1.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. Compounds can have chiral centers and can occur as racemates, individual enantiomers or diastereomers, and mixtures thereof. All such isomeric forms are included within the embodiments disclosed herein, including mixtures thereof. The use of stereomerically pure forms of such compounds, as well as the use of mixtures of those forms are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the compounds can include E and Z isomers, or a mixture thereof, and cis and trans isomers or a mixture thereof. In certain embodiments, compounds are isolated as either the cis or trans isomer. In other embodiments, compounds are a mixture of the cis and trans isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

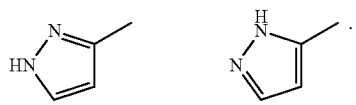

As readily understood by one skilled in the art, a wide variety of functional groups and other structures may exhibit tautomerism and all tautomers of Compound 1 are within the scope of the present invention.

It should also be noted that Compound 1 can contain unnatural proportions of atomic isotopes at one or more of the atoms. For example, Compound 1 may be radiolabeled with radioactive isotopes, such as for example tritium ($^3H$), or carbon-14 ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of Compound 1, whether radioactive or not, are intended to be encompassed within the scope of the embodiments provided herein. In some embodiments, there are provided isotopologues of Compound 1, for example, the isotopologues are deuterium, carbon-13, or nitrogen-15 enriched Compound 1.

The term "solid form" refers to a physical form which is not predominantly in a liquid or a gaseous state. As used herein and unless otherwise specified, the term "solid form," when used herein to refer to Compound 1, refers to a physical form comprising Compound 1 which is not predominantly in a liquid or a gaseous state. A solid form may be a crystalline form, an amorphous form, or a mixture thereof. In certain embodiments, a solid form may be a liquid crystal. In certain embodiments, the term "solid forms comprising Compound 1" includes crystal forms comprising Compound 1, amorphous forms comprising Compound 1, and mixtures thereof. In certain embodiments, the solid form of Compound 1 is Form A, Form B, Form C, Form D or Form E.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, $23^{rd}$ ed., 1843-1844 (1995).

The term "crystal form" or "crystalline form" refers to a solid form that is crystalline. In certain embodiments, crystal forms include salts. In certain embodiments, a crystal form of a substance may be substantially free of amorphous forms and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous forms and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 90% physically and/or chemically pure.

The term "amorphous" or "amorphous form" means that the substance, component, or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In certain embodiments, an amorphous form of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous forms and/or crystal forms on a weight basis. In certain embodiments, an amorphous form of a substance may be physically and/or chemically pure. In certain embodiments, an amorphous form of a substance be about 99%, about 98%, about 97%, about 96%, about 95%, about 94%, about 93%, about 92%, about 91%, or about 90% physically and/or chemically pure.

"Treating" as used herein, means an alleviation, in whole or in part, of the disease or disorder, or symptoms associated with the disease or disorder, or slowing, or halting of further progression or worsening of the disease or disorder, or symptoms associated with the disease or disorder.

"Preventing" as used herein, means prevention of the onset, recurrence, or spread of the disease or disorder, or symptoms associated with the disorder or disease, in a patient at risk for developing the disease or disorder.

The term "effective amount" in connection with Compound 1 means, in one embodiment, an amount capable of alleviating, in whole or in part, symptoms associated with a disorder or disease, or slowing or halting further progression or worsening of those symptoms, or, in another embodiment, an amount capable of preventing or providing prophylaxis for the disease or disorder in a subject at risk for developing the disease or disorder as disclosed herein, such as cancer. In one embodiment an effective amount of Compound 1 is an amount that inhibits a kinase in a cell, such as, for example, in vitro or in vivo. In one embodiment the kinase is mTOR, DNA-PK, PI3K or a combination thereof. In some embodiments, the effective amount of Compound 1 inhibits the kinase in a cell by 10%, 20%, 30%, 40%, 50%, 60%, 70%, 80%, 90% or 99%, compared to the activity of the kinase in an untreated cell. The effective amount of Compound 1, for example in a pharmaceutical composition, may be at a level that will exercise the desired effect; for example, about 0.005 mg/kg of a subject's body weight to about 100 mg/kg of a patient's body weight in unit dosage for both oral and parenteral administration. As will be apparent to those skilled in the art, it is to be expected that the effective amount of Compound 1 disclosed herein may vary depending on the indication being treated, e.g., the effective amount of Compound 1 would likely be different for treating patients suffering from, or at risk for, inflammatory conditions relative to the effective amount of Compound 1 for treating patients suffering from, or at risk of, a different disorder, e.g., cancer or a metabolic disorder.

The term "patient" includes an animal, including, but not limited to, an animal such as a cow, monkey, horse, sheep, pig, chicken, turkey, quail, cat, dog, mouse, rat, rabbit or guinea pig, in one embodiment a mammal, in another embodiment a human.

The term "cancer" refers to any of various malignant neoplasms characterized by the proliferation of cells that can invade surrounding tissue and metastasize to new body sites. Both benign and malignant tumors are classified according to the type of tissue in which they are found. For example, fibromas are neoplasms of fibrous connective tissue, and melanomas are abnormal growths of pigment (melanin) cells. Malignant tumors originating from epithelial tissue, e.g., in skin, bronchi, and stomach, are termed carcinomas. Malignancies of epithelial glandular tissue such as are found in the breast, prostate, and colon, are known as adenocarcinomas. Malignant growths of connective tissue, e.g., muscle, cartilage, lymph tissue, and bone, are called sarcomas. Lymphomas and leukemias are malignancies arising among white blood cells. Through the process of metastasis, tumor cell migration to other areas of the body establishes neoplasms in areas away from the site of initial appearance. Bone tissues are one of the most favored sites of metastases of malignant tumors, occurring in about 30% of all cancer cases. Among malignant tumors, cancers of the lung, breast, prostate or the like are particularly known to be likely to metastasize to bone.

In the context of neoplasm, cancer, tumor growth or tumor cell growth, inhibition may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention. In this context, the term "prevention" includes either preventing the onset of clinically evident neoplasia altogether or preventing the onset of a preclinically evident stage of neoplasia in individuals at risk. Also intended to be encompassed by this definition is the prevention of transformation into malignant cells or to arrest or reverse the progression of premalignant cells to malignant cells. This includes prophylactic treatment of those at risk of developing the neoplasia.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
|---|---|---|---|---|
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | Infiltrate cleared on repeat biopsy; if indeterminate by morphology, immunohisto- chemistry should be negative |
| PR | Regression of measurable disease and no new sites | ≥50% decrease in SPD of up to 6 largest dominant masses; no increase in size of other nodes (a) FDG-avid or PET positive prior to therapy; one or more PET positive at previously involved site (b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or PD | (a) FDG-avid or PET positive prior to therapy; PET positive at prior sites of disease and no new sites on CT or PET (b) Variably FDG-avid or PET negative; no change in size of previous lesions on CT | | |
| PD or relapsed disease | Any new lesion or increase by ≥50% of previously involved sites from nadir | Appearance of a new lesion(s) ≥1.5 cm in any axis, ≥50% increase in SPD of more than one node, or ≥50% increase in longest diameter of a previously identifed node ≥1 cm in short axis Lesions PET positive if FDG-avid lymphoma or PET positive prior to therapy | ≥50% increase from nadir in the SPD of any previous lesions | New or recurrent involvement |

Abbreviations: CR, complete remission; FDG, [$^{18}$F]fluorodeoxyglucose; PET, positron emission tomography; CT, computed tomography; PR, partial remission; SPD, sum of the product of the diameters; SD, stable disease; PD, progressive disease.

| End point | Patients | Definition | Measured from |
|---|---|---|---|
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations: CR: complete remission; PR: partial remission.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of CLL may be assessed by the International Workshop Guidelines for CLL (see Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood, 2008; (111) 12: 5446-5456) using the response and endpoint definitions shown therein and in particular:

| Parameter | CR | PR | PD |
|---|---|---|---|
| Group A | | | |
| Lymphadenopathy[‡] | None > 1.5 cm | Decrease ≥50% | Increase ≥50% |
| Hepatomegaly | None | Decrease ≥50% | Increase ≥50% |
| Splenomegaly | None | Decrease ≥50% | Increase ≥50% |
| Blood lymphocytes | <4000/μL | Decrease ≥50% from baseline | Increase ≥50% over baseline |
| Marrow[‡] | Normocellular, <30% lymphocytes, no B-lymphoid nodules. Hypocellular marrow defines CRi (5.1.6). | 50% reduction in marrow infiltrate, or B-lymphoid nodules | |
| Group B | | | |
| Platelet count | >100 000/μL | >100 000/μL or increase ≥50% over baseline | Decrease of ≥50% from baseline secondary to CLL |
| Hemoglobin | >11.0 g/dL | >11 g/dL or increase ≥50% over baseline | Decrease of >2 g/dL from baseline secondary to CLL |
| Neutrophils[‡] | >1500/μL | >1500/μL or >50% improvement over baseline | |

Group A criteria define the tumor load; Group B criteria define the function of the hematopoietic system (or marrow). CR (complete remission): all of the criteria have to be met, and patients have to lack disease-related constitutional symptoms; PR (partial remission): at least two of the criteria of group A plus one of the criteria of group B have to be met; SD is absence of progressive disease (PD) and failure to achieve at least a PR; PD: at least one of the above criteria of group A or group B has to be met. Sum of the products of multiple lymph nodes (as evaluated by CT scans in clinical trials, or by physical examination in general practice). These parameters are irrelevant for some response categories.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7), using the response and endpoint definitions shown below:

| Response Subcategory | Response Criteria[a] |
|---|---|
| sCR | CR as defined below plus Normal FLC ratio and Absence of clonal cells in bone marrow[b] by immunohistochemistry or immunofluorescence[c] |
| CR | Negative immunofixation on the serum and urine and Disappearance of any soft tissue plasmacytomas and <5% plasma cells in bone marrow[b] |
| VGPR | Serum and urine M-protein detectable by immunofixation but not on electrophoresis or 90% or greater reduction in serum M-protein plus urine M-protein level <100 mg per 24 h |
| PR | ≥50% reduction of serum M-protein and reduction in 24-h urinary M-protein by ≥90% or to <200 mg per 24 h If the serum and urine M-protein are unmeasurable,[d] a ≥50% decrease in the difference between involved and uninvolved FLC levels is required in place of the M-protein criteria If serum and urine M-protein are unmeasurable, and serum free light assay is also unmeasurable, ≥50% reduction in plasma cells is required in place of M-protein, provided baseline bone marrow plasma cell percentage was ≥30% In addition to the above listed criteria, if present at baseline, a ≥50% reduction in the size of soft tissue plasmacytomas is also required |
| SD (not recommended for use as an indicator of response; stability of disease is best described by providing the time to progression estimates) | Not meeting criteria for CR, VGPR, PR or progressive disease |

Abbreviations: CR, complete response; FLC, free light chain; PR, partial response; SD, stable disease; sCR, stringent complete response; VGPR, very good partial response;
[a]All response categories require two consecutive assessments made at anytime before the institution of any new therapy; all categories also require no known evidence of progressive or new bone lesions if radiographic studies were performed. Radiographic studies are not required to satisfy these response requirements; [b]Confirmation with repeat bone marrow biopsy not needed; [c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2. [d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

In certain embodiments, the treatment of a cancer may be assessed by Response Evaluation Criteria in Solid Tumors (RECIST 1.1) (see Thereasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumours: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response; PR = partial response; SD = stable disease; and PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for highgrade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MM scan is defined as the assessment performed at the end of the post-surgery rest period, prior to re-initiating compound treatment. The baseline MM is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined Mill scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bidimensionally. A measurement is made of the maximal enhancing tumor diameter (also known as the longest diameter, LD). The greatest perpendicular diameter is measured on the same image. The cross hairs of bidimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bidimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (ie., less than 5 mm by 5 mm), nonenhancing lesions (eg., as seen on T1-weighted post-contrast, T2-weighted, or fluid-attenuated inversion recovery (FLAIR) images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (eg., recorded in the same order on source documents and eCRFs). All measurable and nonmeasurable lesions must be assessed using the same technique as at baseline (e.g., subjects should be imaged on the same Mill scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

formation into malignant cells or to arrest or reverse the progression of premalignant cells to malignant cells. This includes prophylactic treatment of those at risk of developing a cancer.

5.2 Compound 1

The processes, formulations, solid forms and methods of use provided herein relate to Compound 1:

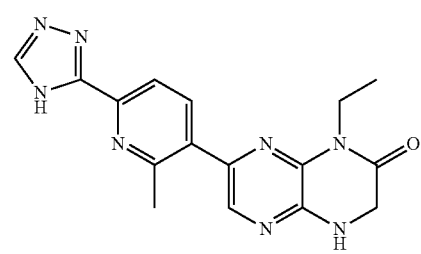

I having the name 1-ethyl-7-(2-methyl-6-(1H-1,2,4-triazol-3-yl)pyridin-3-yl)-3,4-dihydropyrazino[2,3-b]pyrazin-2(1H)-one or a tautomer thereof, for example, 1-ethyl-7-(2-methyl-6-(4H-1,2,4-triazol-3-yl)pyridin-3-yl)-3,4-dihydropyrazino[2,3-b]pyrazin-2(1H)-one, or 1-ethyl-7-(2-methyl-6-(1H-1,2,4-triazol-5-yl)pyridin-3-yl)-3,4-dihydropyrazino[2,3-b]pyrazin-2(1H)-one, and pharmaceutically acceptable salts, isotopologues, metabolites and stereoisomers thereof.

Tautomers of Compound 1 include the following:

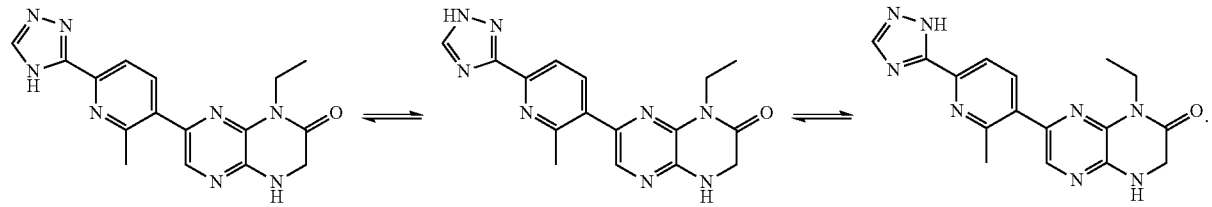 [SMILES: CCN1C(=O)CNc2ncc(-c3ccc(-c4nnc[nH]4)nc3C)nc21 ; CCN1C(=O)CNc2ncc(-c3ccc(-c4nc[nH]n4)nc3C)nc21 ; CCN1C(=O)CNc2ncc(-c3ccc(-c4ncn[nH]4)nc3C)nc21]

In certain embodiments, treatment of a cancer may be assessed by the inhibition of phosphorylation of S6RP, 4E-BP1, AKT and/or DNA-PK in circulating blood and/or tumor cells, and/or skin biopsies or tumor biopsies/aspirates, before, during and/or after treatment with a TOR kinase inhibitor. For example, the inhibition of phosphorylation of S6RP, 4E-BP1, AKT and/or DNA-PK is assessed in B-cells, T-cells and/or monocytes. In other embodiments, treatment of a cancer may be assessed by the inhibition of DNA-dependent protein kinase (DNA-PK) activity in skin samples and/or tumor biopsies/aspirates, such as by assessment of the amount of pDNA-PK 52056 as a biomarker for DNA damage pathways, before, during, and/or after TOR kinase inhibitor treatment. In one embodiment, the skin sample is irradiated by UV light.

In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of trans-

5.3 Methods for Preparing Compound 1

Provided herein are methods of preparing Compound 1

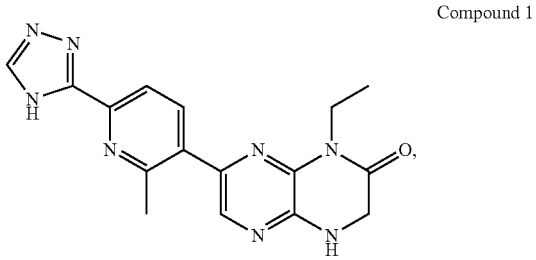 [SMILES: CCN1C(=O)CNc2ncc(-c3ccc(-c4nnc[nH]4)nc3C)nc21]

Compound 1 the methods comprising contacting a compound of Formula G

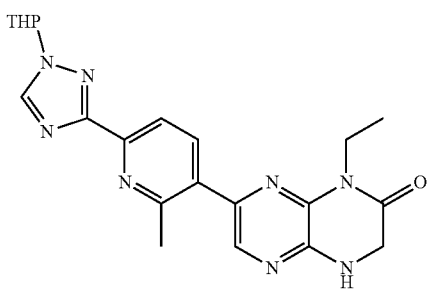

G with an acid, optionally in a solvent, followed by neutralization with a base. In certain embodiments, the solvent comprises one or more of 1-propanol, methanol, ethanol, or isopropanol. In a particular embodiment, the acid is aqueous HCl, acetic acid or trifluoroacetic acid. In certain embodiments, the base is aqueous KHCO₃ or aqueous NH₄OH. In one embodiment, the solvent additionally comprises butylated hydroxytoluene. In certain embodiments, the methods comprise: (a) dissolving the protected compound G in a mixture of ethanol, water, and HCl; (b) neutralizing with NH₄OH; (c) filtering the mixture; (d) collecting the solid; (e) dissolving the deprotected compound in a mixture of ethanol, water, and HCl; (f) treating the solution with activated carbon; (g) removing the activated carbon by filtration; (h) neutralizing with NH₄OH; and (i) filtering the mixture.

In some such embodiments, the methods further comprise preparing a compound of formula G

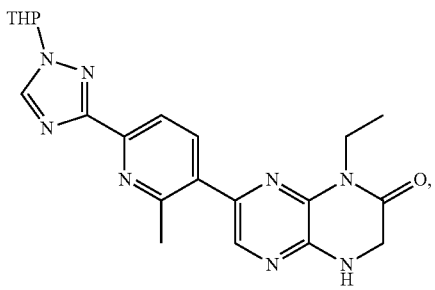

G the methods comprising contacting a compound of formula E

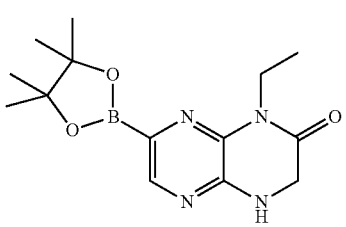

E with a compound of formula F,

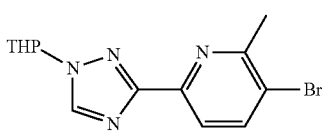

F in the presence of a palladium catalyst, a solvent and a base. In certain embodiments, the palladium catalyst is PdAmphos₂Cl₂. In certain embodiments, the solvent is a mixture of tetrahydrofuran and water. In certain embodiments, the base is K₂CO₃ or KHCO₃. In certain embodiments, the methods additionally comprise use of activated carbon to remove impurities. In certain embodiments, the methods comprise: (a) contacting KHCO₃, PdAmphos₂Cl₂, and compounds E and F, in tetrahydrofuran and water; (b) treating the solution with activated carbon; (c) removing the activated carbon by filtration; (d) concentrating the filtrate to about 70% of the original volume; (e) cooling the filtrate; (f) contacting the filtrate with water; (g) seeding the filtrate with crystalline G; and (h) filtering the mixture.

In some such embodiments, the methods further comprise preparing a compound of formula E

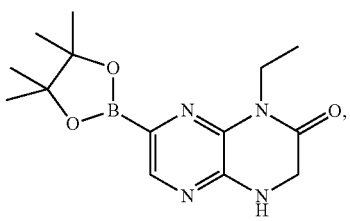

E the methods comprising contacting a compound of formula D

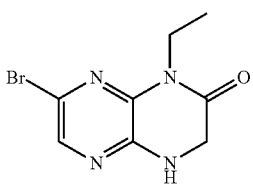

D with a boron source and a palladium catalyst in the presence of a base in a solvent. In one embodiment, the boron source is bis(pinacolato)diboron. In one embodiment, the palladium catalyst is PdAmphos₂Cl₂. In one embodiment, the base is KOAc. In one embodiment, the solvent is tetrahydrofuran. In certain embodiments, the methods additionally comprise use of activated carbon to remove impurities. In certain embodiments, the methods comprise: (a) contacting compound D with bis(pinacolato)diboron, PdAmphos₂Cl₂, and potassium acetate in tetrahydrofuran; (b) filtering the mixture; (c) treating a warm tetrahydrofuran solution of compound E with activated carbon; (d) removing the activated carbon by filtration; (e) concentrating the filtrate to about 20% of the original volume; (f) cooling the filtrate; (g) contacting the filtrate with heptane; and (h) filtering the mixture.

In some such embodiments, the methods further comprise preparing a compound of formula D

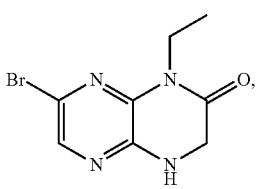

D the methods comprising contacting a compound of formula C

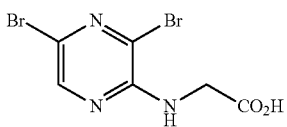

with EtNH$_2$ optionally in the presence of a base optionally in a solvent, followed by acidification. In certain embodiments, the base is EtNH$_2$ or Hunig's Base. In certain embodiments, the solvent is water. In certain embodiments, acidification is carried out by the addition of aqueous H$_3$PO$_4$. In certain embodiments, the methods comprise: (a) contacting compound C with an excess of ethylamine in water; (b) treating the solution with phosphoric acid; and (c) filtering the mixture.

In some such embodiments, the methods further comprise preparing a compound of formula C

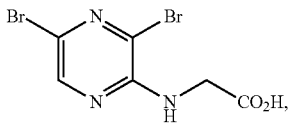

the methods comprising contacting a compound of formula B

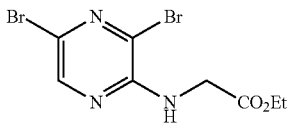

with a base optionally in a solvent, followed by neutralization with an acid. In certain embodiments, the base is NAOH. In certain embodiments the solvent is tetrahydrofuran. In certain embodiments, neutralization is carried out by the addition of aqueous H$_3$PO$_4$. In certain embodiments, the methods comprise: (a) contacting Compound B with NaOH in tetrahydrofuran and water; (b) treating the solution with phosphoric acid and heptane; (c) concentrating the organic layer; (d) distilling with addition of heptane; (e) seeding the solution with crystalline Compound C; (f) distilling with addition of heptane; (g) cooling the slurry; and (h) filtering the mixture.

In one embodiment, provided herein are methods of recrystallizing Compound 1, which comprise the steps of:
(a) dissolving Compound 1 in a mixture of ethanol, water, and HCl at elevated temperature, for example about 45° C.;
(b) neutralizing the mixture with NH$_4$OH at elevated temperature, for example, about 45° C.; and
(c) filtering the mixture, for example at room temperature.

In some embodiments, the methods additionally comprise treating the Compound 1 solution with activated carbon at elevated temperature, for example, about 45° C., and removing the activated carbon prior to neutralization. In some embodiments, the methods additionally comprise treating the Compound 1 solution with a metal scavenger at elevated temperature, for example 60° C., and removing the metal scavenger, prior to treating with activating carbon.

In one embodiment, provided herein are methods of recrystallizing Compound 1, which comprise the steps of:
(a) dissolving Compound 1 in a mixture of 1-propanol, water, and HCl;
(b) neutralizing the mixture with an aqueous base, for example NH$_4$OH or KHCO$_3$, at elevated temperature, for example about 45° C. to about 60° C.; and
(c) filtering the mixture for example, at room temperature.

In some embodiments, the methods additionally comprise treating the Compound 1 solution with activated carbon at elevated temperature, for example, about 45° C., and removing the activated carbon prior to neutralization. In some embodiments, the methods additionally comprise treating the Compound 1 solution with a metal scavenger at elevated temperature, for example 60° C., and removing the metal scavenger, prior to treating with activating carbon.

In certain embodiments, provided herein are synthetic steps i-v, including combinations thereof, which are useful for the preparation of Compound 1:

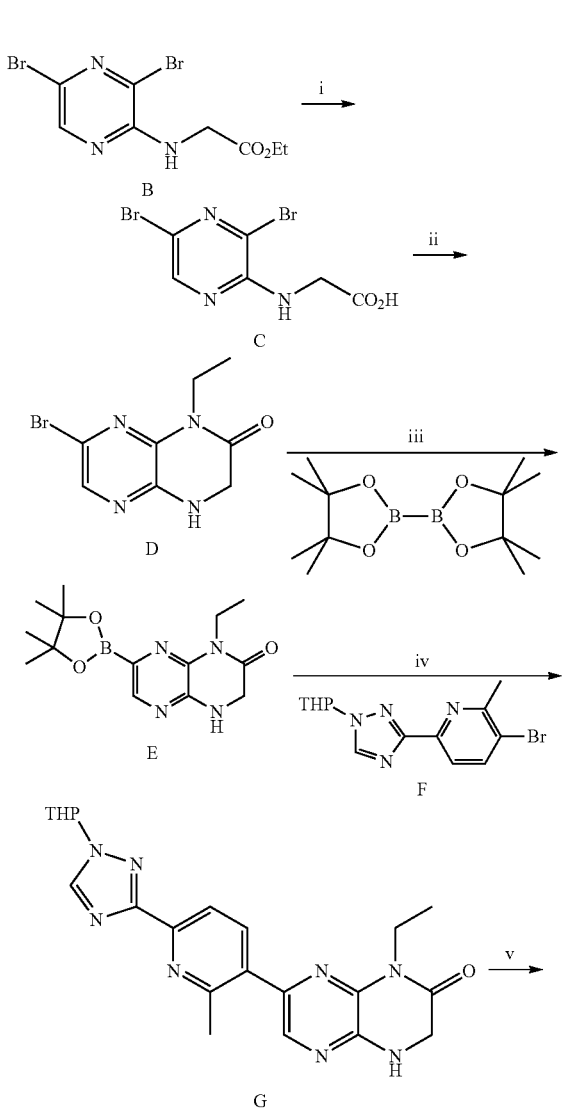

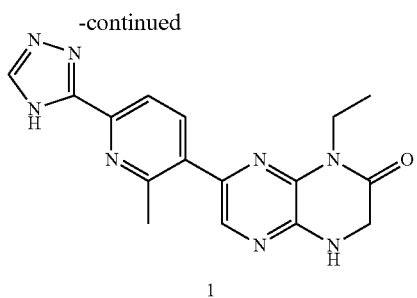

wherein step i) comprises:
  (a) contacting Compound B with aqueous NaOH in tetrahydrofuran;
  (b) treating the solution with phosphoric acid and heptane;
  (c) concentrating the organic layer;
  (d) distilling with addition of heptane;
  (e) seeding the solution with crystalline Compound C;
  (f) distilling with addition of heptane;
  (g) cooling the slurry; and
  (h) filtering the mixture;
step ii) comprises:
  (a) contacting Compound C with an excess of ethylamine in water;
  (b) treating the solution with phosphoric acid; and
  (c) filtering the mixture;
step iii) comprises:
  (a) contacting Compound D with bis(pinacolato)diboron, PdAmphos$_2$Cl$_2$, and potassium acetate in tetrahydrofuran;
  (b) filtering the mixture;
  (c) treating a warm tetrahydrofuran solution of Compound E with activated carbon;
  (d) removing the activated carbon by filtration;
  (e) concentrating the filtrate;
  (f) cooling the filtrate;
  (g) seeding the solution with crystalline Compound E;
  (h) contacting the filtrate with heptane; and
  (i) filtering the mixture;
step iv) comprises:
  (a) contacting KHCO$_3$ or K$_2$HCO$_3$, PdAmphos$_2$Cl$_2$, and Compounds E and F, in tetrahydrofuran and water;
  (b) treating the solution with activated carbon;
  (c) removing the activated carbon by filtration;
  (d) concentrating the filtrate;
  (e) cooling the filtrate;
  (f) contacting the filtrate with water;
  (g) seeding the filtrate with crystalline Compound G; and
  (h) filtering the mixture;
step v) comprises:
  (a) dissolving the protected compound G in a mixture of ethanol, water, and HCl at elevated temperature, for example, about 45° C.;
  (b) neutralizing with NH$_4$OH;
  (c) filtering the mixture;
  (d) collecting the solid;
  (e) dissolving the deprotected compound in a mixture of ethanol, water, and HCl at elevated temperature, for example, about 45° C.;
  (f) treating the solution with activated carbon;
  (g) removing the activated carbon by filtration;
  (h) neutralizing with NH$_4$OH at elevated temperature, for example, about 45° C.;
  (g) seeding the solution with crystalline Compound 1;
  (h) neutralizing with NH$_4$OH;
  (i) cooling the filtrate, and
  (j) filtering the mixture.

The methods for preparing Compound 1 are further exemplified by the working examples provided herein.

In one embodiment, certain isotopologues of Compound 1 are prepared as follows:

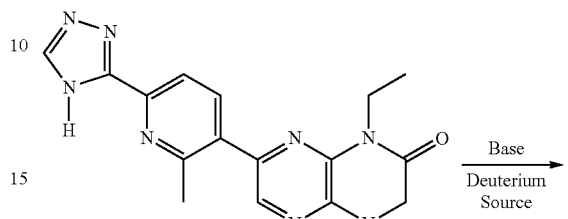

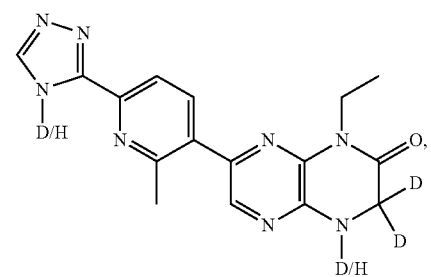

wherein "D/H" indicates that the amine or triazole nitrogens may each be independently exchanged with deuterium, and wherein the base and the deuterium source are selected to perform the isotopic enrichment, as known by one skilled in the art.

In certain embodiments, the base used to promote the transformation from Compound 1 to an isotopologue (i.e., contacting Compound 1 with a base and an exchangeable deuterium source) is sodium C$_{1-14}$ alkoxide, potassium C$_{1-14}$ alkoxide, sodium hydride, potassium hydride, calcium hydride, cesium carbonate, lithium hexamethyldisilazide (LiHMDS), lithium diisopropylamide (LDA), 2-tert-butyl-1,1,3,3-tetramethyl-guanidine (Barton's Base), 1,8-diazabicyclo[5.4.0]undec-7-ene (DBU), 1,5-diazabicyclo[4.3.0]non-5-ene (DBN), 1,4-diazabicyclo(2.2.2)octane (DABCO), N,N-diisopropylethylamine (DIPEA or Hünig's base), pyridine, 2,6-di-tert-butyl-pyridine, 2,6-lutidine, lithium tetramethylpiperidide (LiTMP or harpoon base), 7-methyl-1,5,7 triazabicyclo[4.4.0]dec-5-ene (MTBD), 1,2,2,6,6-pentamethylpiperidine (PMP), 2,2,6,6-tetramethylpiperidine (TMP), tributylamine, 2,4,6-tri-tert-butylpyridine, tris(trimethylsilyl)amine, n-butyllithium, sec-butyllithium, tert-butyllithium, potassium bis(trimethylsilyl)amide, sodium tert-butoxide, tert-butylimino-tris(dimethylamino)phosphorane, or 2-tert-butylimino-2-diethylamino-1,3-dimethylperhydro-1,3,2-diazaphosphorine. In some embodiments, the base is potassium tert-butoxide.

In certain embodiments, the deuterium source used to promote the transformation from Compound 1 to an isotopologue (i.e., contacting Compound 1 with a base and an exchangeable deuterium source) is selected from the group consisting of D$_2$O, C$_{1-14}$ alkyl-OD, C$_{1-14}$ alkyl-COOD, aryl- OD, heteroaryl-OD, aryl-SO$_3$D, deuterium chloride, deuterium bromide, deuterium iodide, sulfuric acid-D$_2$, and nitric acid-D$_1$. In some embodiments, the deuterium source is monodeuterated tert-butyl alcohol (t-BuOD).

In some embodiments, the base used to promote the transformation from Compound 1 to an isotopologue is potassium tert-butoxide and the deuterium source is monodeuterated tert-butyl alcohol (t-BuOD).

In one embodiment, certain isotopologues of Compound 1 are prepared according to the following synthetic pathway, using conditions as set forth above in connection with the preparation of Compound 1:

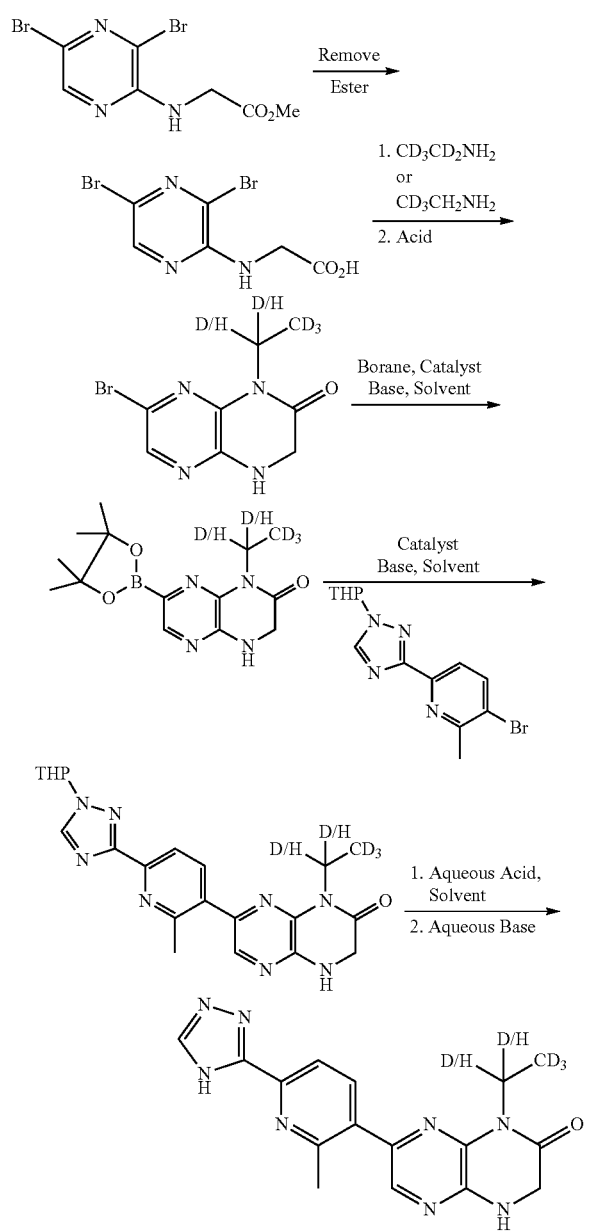

In one embodiment, certain isotopologues of Compound 1 are prepared according to the following synthetic pathway, using conditions as set forth above in connection with the preparation of Compound 1:

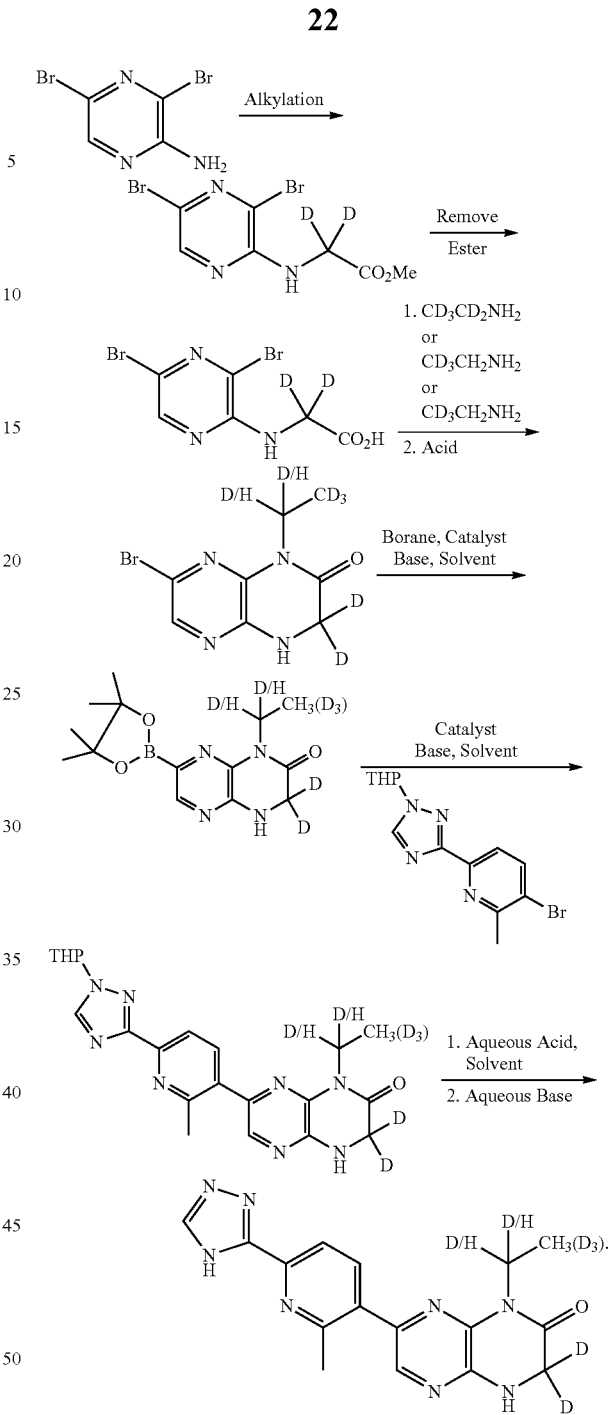

5.4 Solid Forms of Compound 1

In certain embodiments, provided herein are solid forms of Compound 1 or a pharmaceutically acceptable salt thereof. In certain embodiments, the solid form is crystalline. In certain embodiments, the solid form is a single-component solid form. In certain embodiments, the solid form is anhydrous.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

The solid forms provided herein (e.g., Form A, Form B, Form C, Form D and Form E of Compound 1) may be characterized using a number of methods known to a person skilled in the art, including, but not limited to, single crystal X-ray diffraction, X-ray powder diffraction (XRPD), microscopy (e.g., scanning electron microscopy (SEM)), thermal analysis (e.g., differential scanning calorimetry (DSC), thermal gravimetric analysis (TGA), and hot-stage microscopy), and spectroscopy (e.g., infrared, Raman, and solid-state nuclear magnetic resonance). The particle size and size distribution of the solid form provided herein may be determined by conventional methods, such as laser light scattering technique.

The purity of the solid form provided herein may be determined by standard analytical methods, such as thin layer chromatography (TLC), gel electrophoresis, gas chromatography, high performance liquid chromatography (HPLC), and mass spectrometry (MS).

It should be understood that the numerical values of the peaks of an X-ray powder diffraction pattern may vary slightly from one machine to another or from one sample to another, and so the values quoted are not to be construed as absolute, but with an allowable variability, such as ±0.2 degrees 2 theta (see United State Pharmacopoeia, page 2228 (2003)). A stack plot of X-ray powder diffraction pattern for various solid forms of Compound 1 is shown in FIG. 1.

Figure 2:
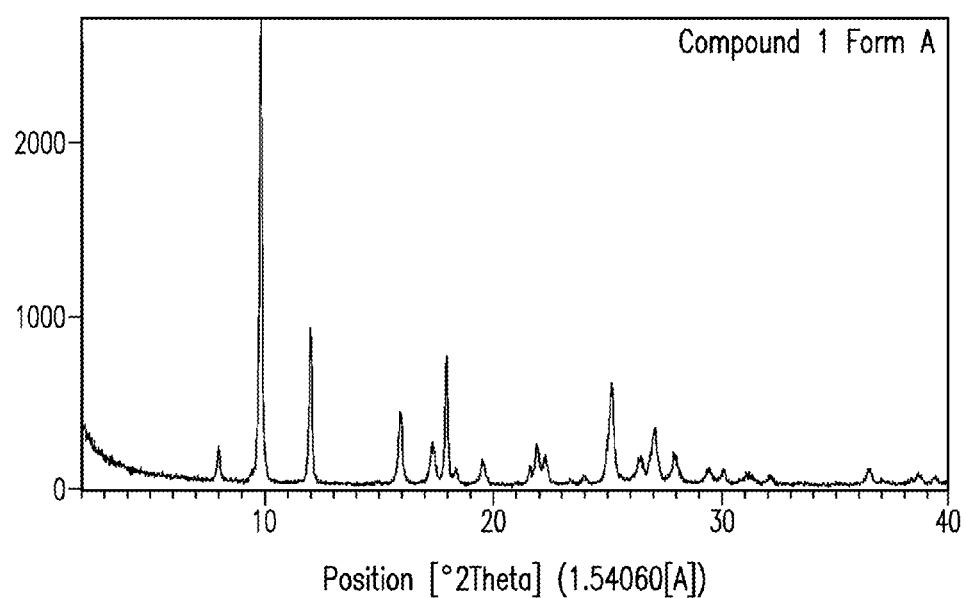
FIG. 2 depicts an X-ray powder diffractogram of Form A of Compound 1.

In one embodiment, provided herein is Form A of Compound 1. In one embodiment, Form A of Compound 1 is anhydrous. In another embodiment, Form A of Compound 1 is non-hygroscopic. In another embodiment, Form A of Compound 1 is crystalline. In one embodiment, Form A of Compound 1 has an X-ray powder diffraction pattern substantially as shown in FIG. 2. In one embodiment, Form A of Compound 1 has one or more characteristic X-ray powder diffraction peaks at a two-theta angle of approximately 8.0, 9.8, 12.0, 15.9, 17.4, 17.9, 18.3, 19.5, 21.6, 21.9, 22.3, 24.0, 25.2, 26.4, 26.5, 27.1, 28.0, 29.4, 30.1, 31.3, 32.1, 36.4, 38.6 or 39.4 degrees. In a specific embodiment, Form A of Compound 1 has one, two, three, four, five, six, seven or eight characteristic X-ray powder diffraction peaks at a two-theta angle of approximately 9.8, 12.0, 15.9, 17.4, 17.9, 21.9, 25.2 or 27.1 degrees. In another embodiment, Form A of Compound 1 has one, two, three or four characteristic X-ray powder diffraction peaks at a two-theta angle of approximately 9.8, 12.0, 17.9 or 25.2 degrees. In another embodiment, Form A of Compound one has one, two, three, four, five, six, seven or eight characteristic X-ray powder diffraction peaks as set forth in Table 2.

Figure 3:
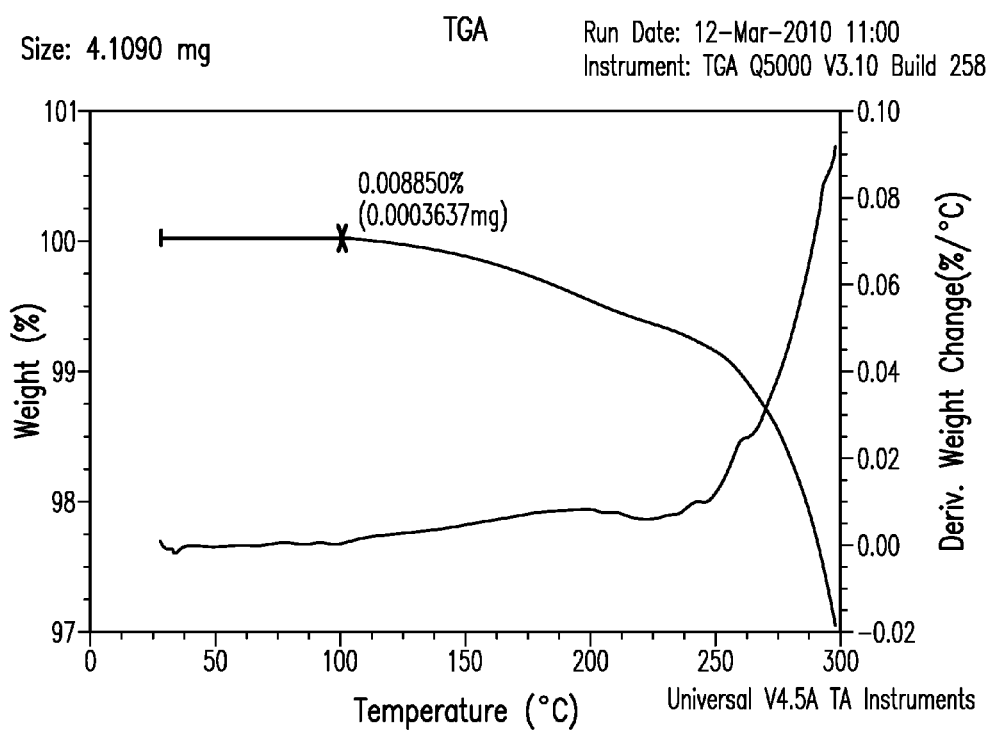
FIG. 3 depicts a thermogravimetric thermogram of Form A of Compound 1.

In another embodiment, Form A of Compound 1 has a thermogravimetric thermogram substantially as shown in FIG. 3. In certain embodiments, Form A of Compound 1 shows less than about 10%, less than about 5%, less than about 3%, less than about 2%, less than about 1%, less than about 0.5%, less than about 0.2%, less than about 0.1%, less than about 0.05%, or less than about 0.01%, e.g., about 0.009%, weight loss between about 25° C. to about 100° C. in a thermogravimetric thermogram. In certain embodiments, Form A of Compound 1 shows less than about 0.1% weight loss between about 25° C. to about 100° C. in a thermogravimetric thermogram. In certain embodiments, Form A of Compound 1 shows about 0.01% weight loss between about 25° C. to about 100° C. in a thermogravimetric thermogram. In certain embodiments, Form A of Compound 1 shows no weight loss until degradation at about 260° C. in a thermogravimetric thermogram. In certain embodiments, Form A of Compound 1 is anhydrous. In certain embodiments, Form A of Compound 1 is unsolvated.

Figure 4:
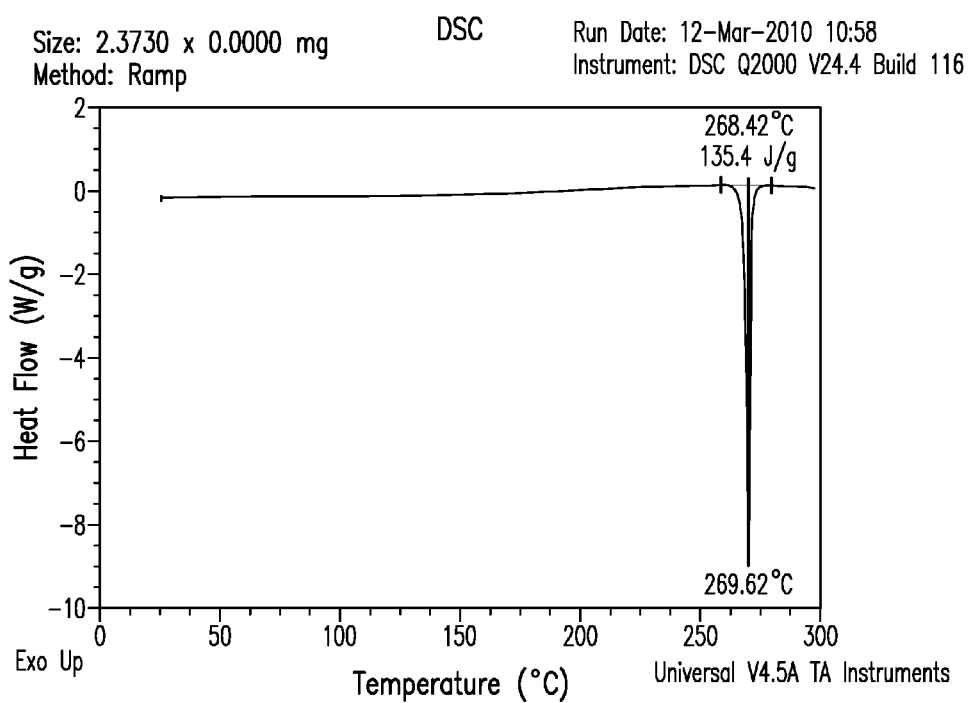
FIG. 4 depicts a differential scanning calorimetric thermogram of Form A of Compound 1.

In yet another embodiment, Form A of Compound 1 has a differential scanning calorimetric (DSC) thermogram substantially as shown in FIG. 4. In certain embodiments, Form A of Compound 1 has an endotherm with a peak temperature of about 270° C. in a DSC thermogram. In certain embodiments, Form A of Compound 1 has an endotherm with an onset temperature of about 268° C. in a DSC thermogram. In certain embodiments, Form A of Compound 1 has an endotherm with a peak temperature of about 270° C. and an onset temperature of about 268° C. in a DSC thermogram. In one embodiment, Form A of Compound 1 has a melting temperature of about 268-270° C. In certain embodiment, Form A of Compound 1 has a melting temperature of about 270° C.

Figure 5:
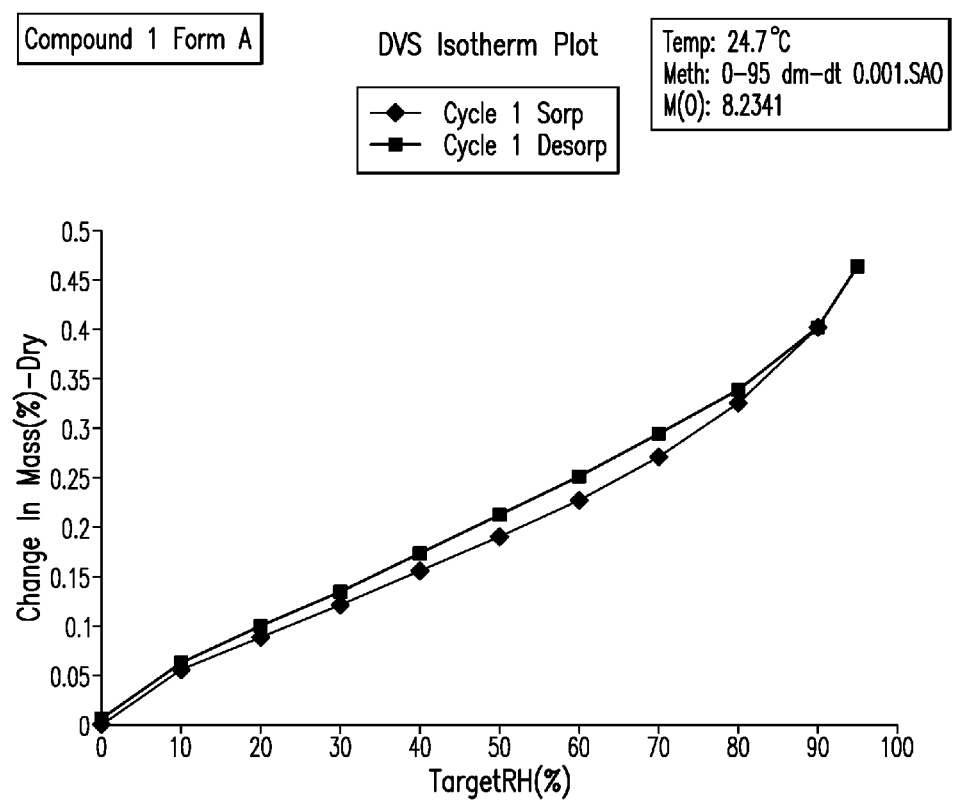
FIG. 5 depicts a dynamic vapor sorption plot of Form A of Compound 1.

In yet another embodiment, Form A of Compound 1 has a dynamic vapor sorption (DVS) plot substantially as shown in FIG. 5. In yet another embodiment, Form A of Compound 1 is non-hygroscopic, e.g., exhibits a mass gain of less than about 0.35% w/w of when subjected to an increase in humidity from about 0% to about 80% relative humidity (RH). In another embodiment, Form A of Compound exhibits a mass gain of about 0.08% w/w of when subjected to an increase in humidity from about 80% to about 90% relative humidity. In certain embodiments, Form A of Compound 1 exhibits no greater than about 2% w/w, no greater than about 1% w/w, no greater than about 0.6% w/w, no greater than about 0.5% w/w weight gain in response to an increase in humidity from about 0% to about 95% relative humidity at about 25° C. In certain embodiments, Form A of Compound 1 exhibits about 0.5% w/w weight gain in response to an increase in humidity from about 0% to about 95% relative humidity at about 25° C. In certain embodiments, Form A of Compound 1 exhibits no greater than about 2% w/w, no greater than about 1% w/w, no greater than about 0.6% w/w, no greater than about 0.4% w/w, no greater than about 0.2% w/w weight gain in response to an increase in humidity from about 0% to about 50% relative humidity at about 25° C. In certain embodiments, Form A of Compound 1 exhibits about 0.2% w/w weight gain in response to an increase in humidity from about 0% to about 50% relative humidity at about 25° C.

Figure 6:
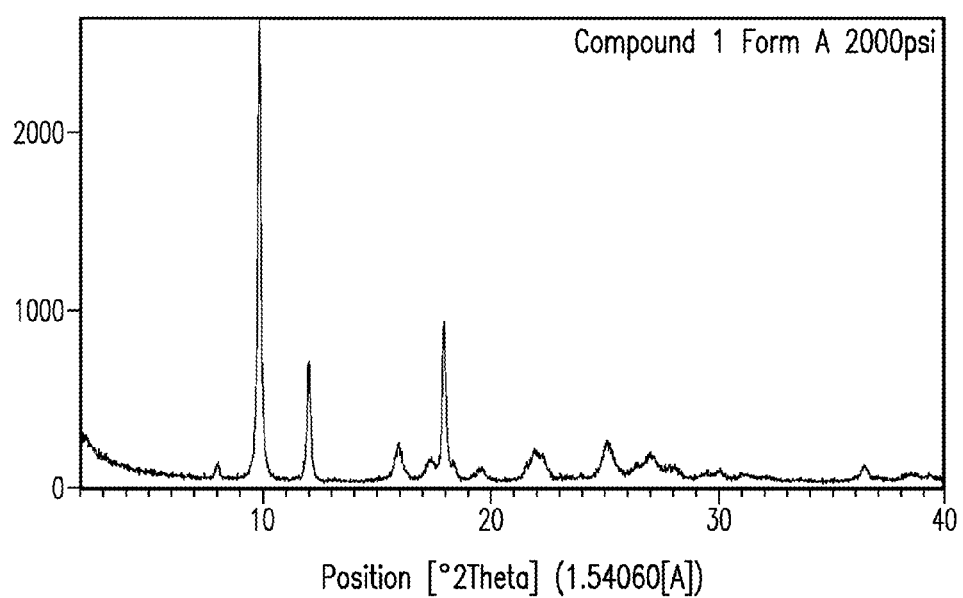
FIG. 6 depicts an X-ray powder diffractogram of Form A of Compound 1 after compression at 2000 psi for 1 minute.

In one embodiment, Form A of Compound 1 is stable to high pressure. In one embodiment, Form A of Compound 1, upon application of 2000-psi pressure for about 1 minute, has an X-ray powder diffraction pattern substantially as shown in FIG. 6. In one embodiment, Form A of Compound 1 upon application of 2000-psi pressure for about 1 minute has one or more characteristic X-ray powder diffraction peaks at a two-theta angle of approximately 8.0, 9.9, 12.1, 15.9, 17.3, 18.1, 18.3, 19.5, 21.8, 25.2, or 27.1 degrees. In a specific embodiment, Form A of Compound 1 upon application of 2000-psi pressure for about 1 minute has one, two, three, four, five, six, seven or eight characteristic X-ray powder diffraction peaks at a two-theta angle of approximately 8.0, 9.9, 12.1, 15.9, 17.3, 18.1, 21.8, or 25.2 degrees. In another embodiment, Form A of Compound 1 upon application of 2000-psi pressure for about 1 minute has one, two, three or four characteristic X-ray powder diffraction peaks at a two-theta angle of approximately 9.9, 12.1, 18.1, or 25.2 degrees. In a specific embodiment, Form A of Compound 1 upon application of 2000-psi pressure for about 1 minute has one, two, three, four, five, six, seven or eight characteristic X-ray powder diffraction peaks at a two-theta angle of approximately 8.0, 10.0, 12.0, 16.0, 17.5, 18.0, 22.0, or 25.0 degrees. In another embodiment, Form A of Compound 1 upon application of 2000-psi pressure for about 1 minute has one, two, three or four characteristic X-ray powder diffraction peaks at a two-theta angle of approximately 10.0, 12.0, 18.0, or 25.0 degrees.

In still another embodiment, Form A of Compound 1 is substantially pure. In certain embodiments, the substantially pure Form A of Compound 1 is substantially free of other solid forms, e.g., amorphous form. In certain embodiments, the purity of the substantially pure Form A of Compound 1 is no less than about 95%, no less than about 96%, no less than about 97%, no less than about 98%, no less than about 98.5%, no less than about 99%, no less than about 99.5%, or no less than about 99.8%.

Figure 7:
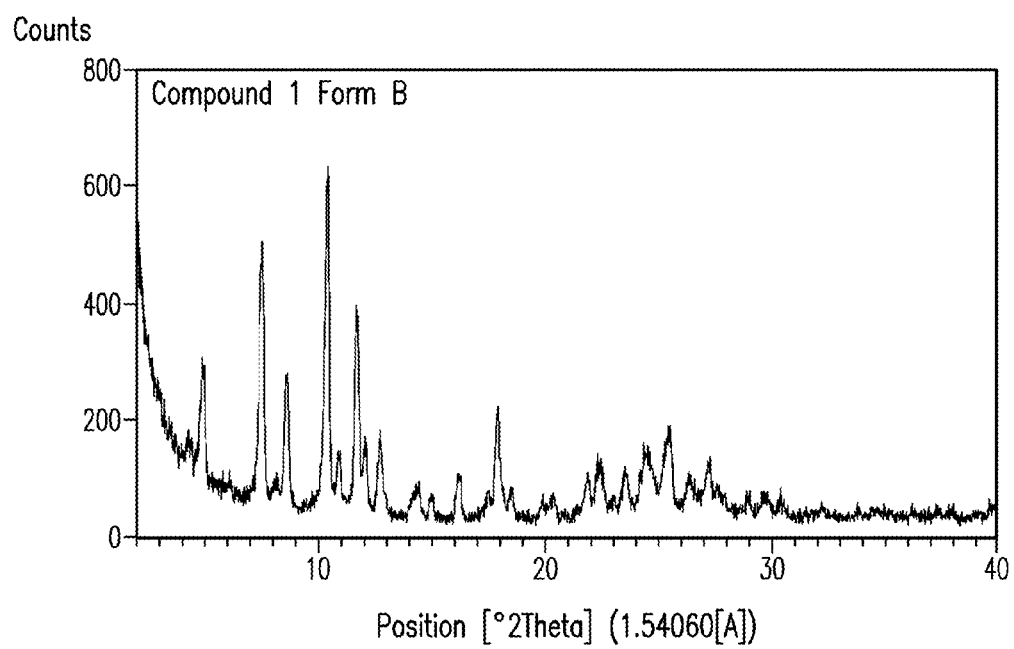
FIG. 7 depicts an X-ray powder diffractogram of Form B of Compound 1.

In one embodiment, provided herein is Form B of Compound 1. In one embodiment, Form B of Compound 1 is a hydrate. In another embodiment, Form B of Compound 1 is crystalline. In one embodiment, Form B of Compound 1 has an X-ray powder diffraction pattern substantially as shown in FIG. 7. In one embodiment, Form B of Compound 1 has one or more characteristic X-ray powder diffraction peaks at a two-theta angle of approximately 4.9, 7.5, 8.6, 10.4, 10.9, 11.7, 12.1, 12.7, 14.4, 15.0, 16.2, 17.5, 17.9, 18.5, 19.9, 20.4, 21.9, 22.4, 23.6, 24.5, 25.5, 26.4, 27.3, 29.0, 29.8 or 30.5 degrees. In a specific embodiment, Form B of Compound 1 has one, two, three, four, five, six, seven or eight characteristic X-ray powder diffraction peaks at a two-theta angle of approximately 4.9, 7.5, 8.6, 10.4, 11.7, 12.7, 17.9 or 25.5 degrees. In another embodiment, Form B of Compound 1 has one, two, three or four characteristic X-ray powder diffraction peaks at a two-theta angle of approximately 7.5, 8.6, 10.4 or 11.7 degrees. In another embodiment, Form B of Compound one has one, two, three, four, five, six, seven or eight characteristic X-ray powder diffraction peaks as set forth in Table 3.

Figure 8:
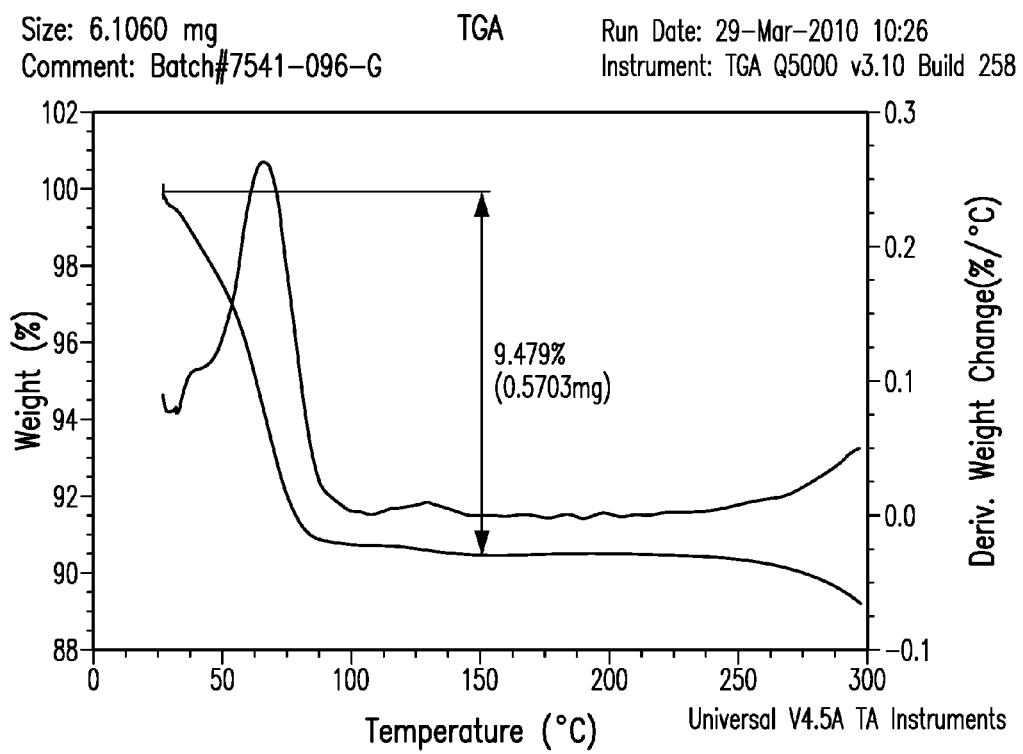
FIG. 8 depicts a thermogravimetric thermogram of Form B of Compound 1.

In another embodiment, Form B of Compound 1 has a thermogravimetric thermogram substantially as shown in FIG. 8. In certain embodiments, Form B of Compound 1 shows less than about 20%, less than about 15%, less than about 10% e.g., about 9.5%, weight loss between about 25° C. to about 100° C. in a thermogravimetric thermogram. In certain embodiments, Form B of Compound 1 shows less than about 10% weight loss between about 25° C. to about 100° C. in a thermogravimetric thermogram. In certain embodiments, Form B of Compound 1 is a hydrate. In certain embodiments, Form B of Compound 1 is unsolvated.

Figure 9:
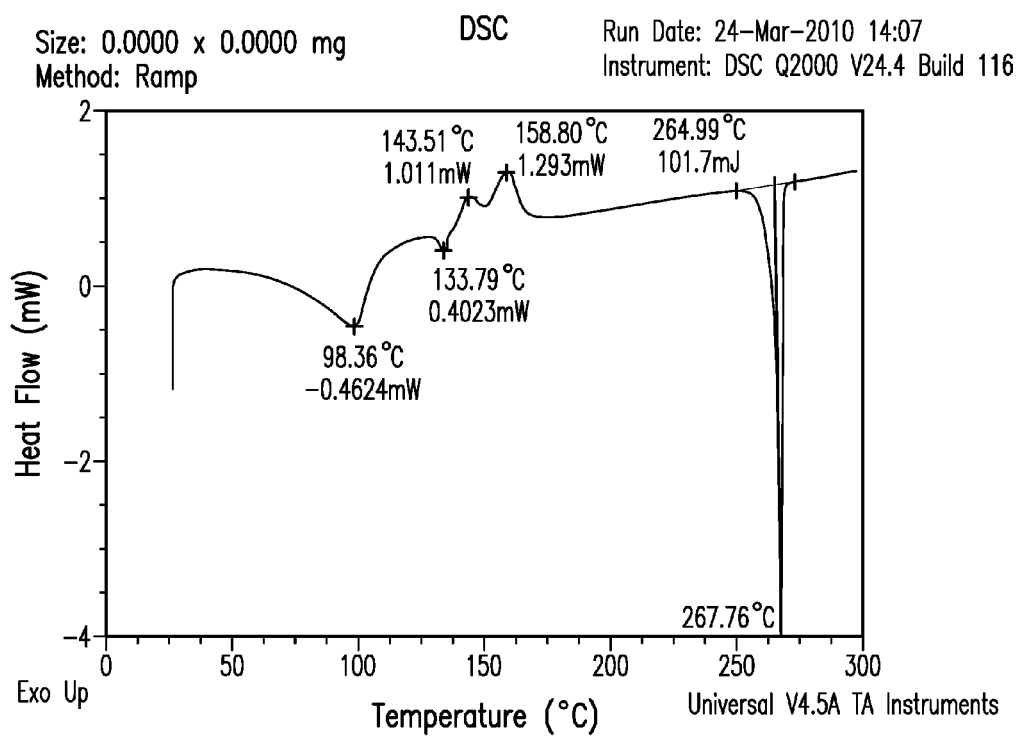
FIG. 9 depicts a differential scanning calorimetric thermogram of Form B of Compound 1.

In yet another embodiment, Form B of Compound 1 has a differential scanning calorimetric (DSC) thermogram substantially as shown in FIG. 9. In certain embodiments, Form B of Compound 1 has an endotherm with a peak temperature of about 268° C. in a DSC thermogram. In certain embodiments, Form B of Compound 1 has an endotherm with an onset temperature of about 265° C. in a DSC thermogram. In certain embodiments, Form B of Compound 1 has an endotherm with a peak temperature of about 268° C. and an onset temperature of about 265° C. in a DSC thermogram. In one embodiment, Form B of Compound 1 has a melting temperature of about 265-268° C. In certain embodiment, Form B of Compound 1 has a melting temperature of about 268° C.

Figure 10:
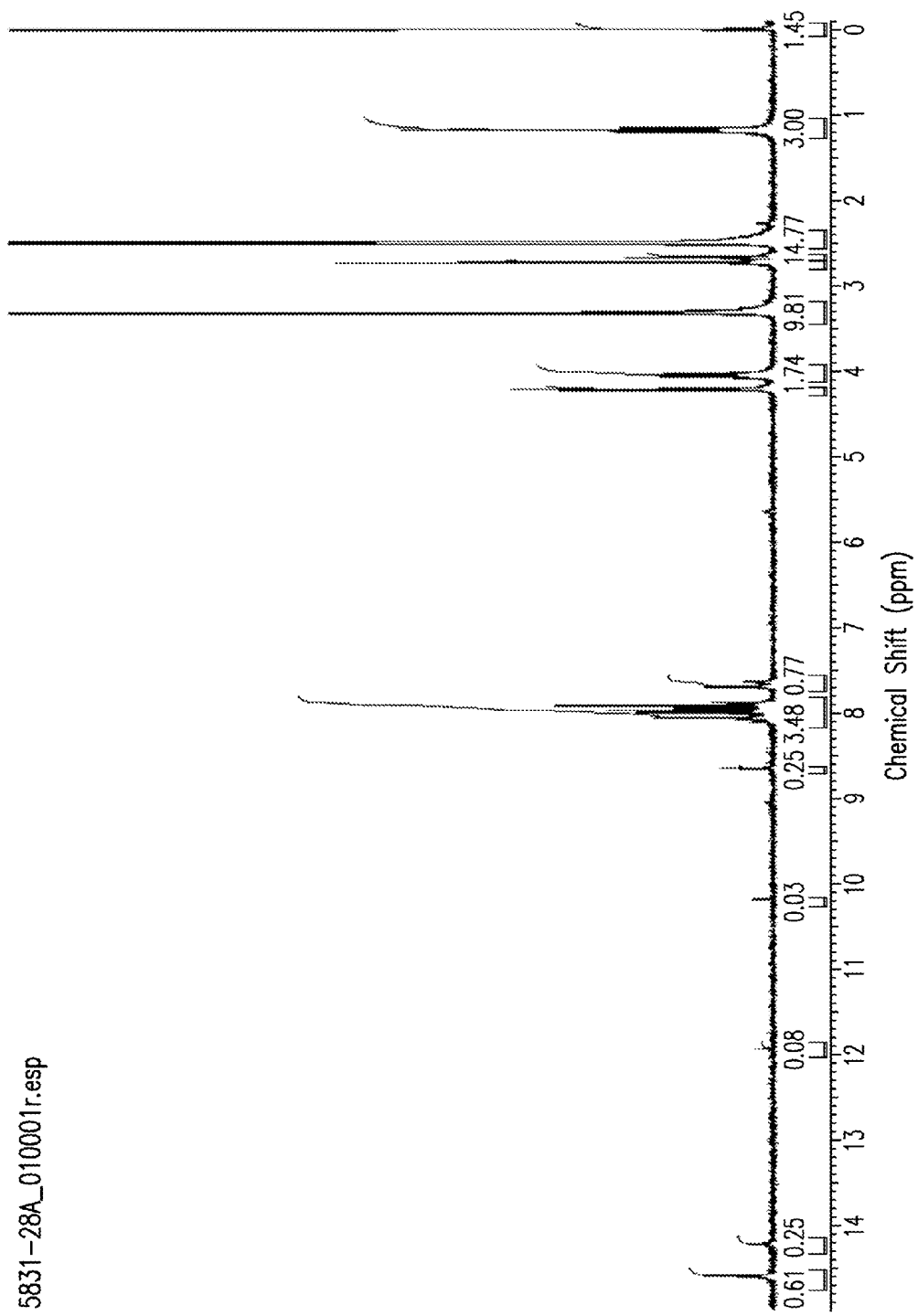
FIG. 10 depicts the $^1$H NMR Spectrum of Form B of Compound 1.

In another embodiment, Form B of Compound 1 has a $^1$H NMR spectrum substantially as shown in FIG. 10.

Figure 11:
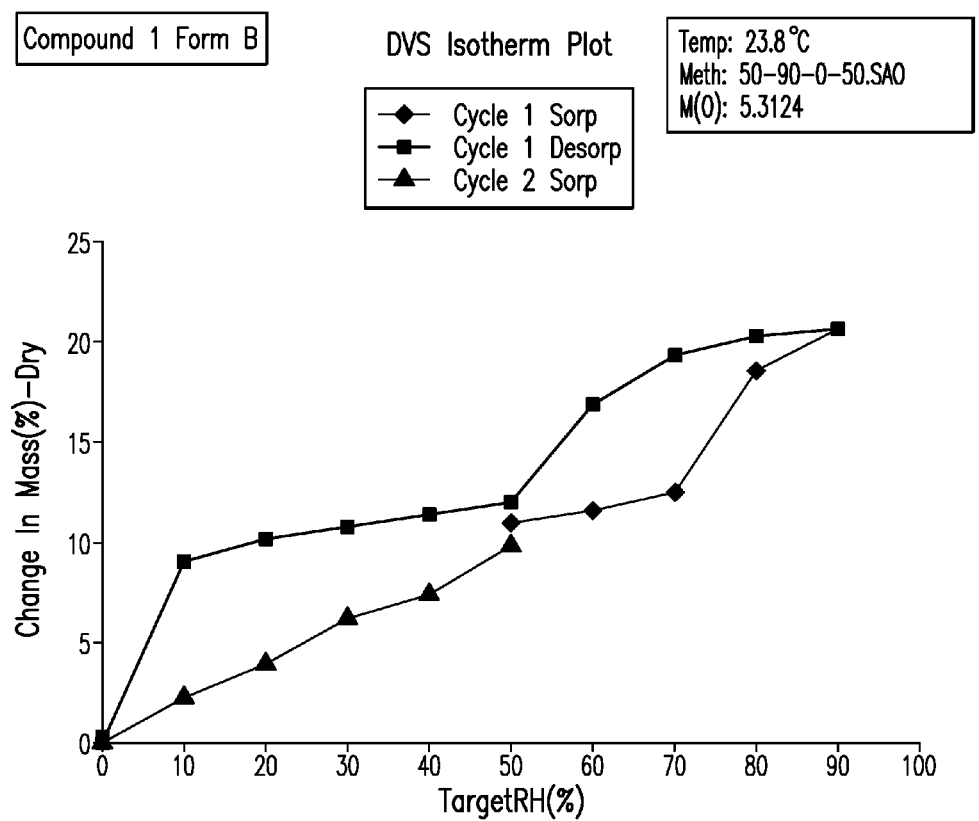
FIG. 11 depicts a dynamic vapor sorption plot of Form B of Compound 1.

In yet another embodiment, Form B of Compound 1 has a dynamic vapor sorption (DVS) plot substantially as shown in FIG. 11.

In still another embodiment, Form B of Compound 1 is substantially pure. In certain embodiments, the substantially pure Form B of Compound 1 is substantially free of other solid forms, e.g., amorphous form. In certain embodiments, the purity of the substantially pure Form B of Compound 1 is no less than about 95%, no less than about 96%, no less than about 97%, no less than about 98%, no less than about 98.5%, no less than about 99%, no less than about 99.5%, or no less than about 99.8%.

Figure 12:
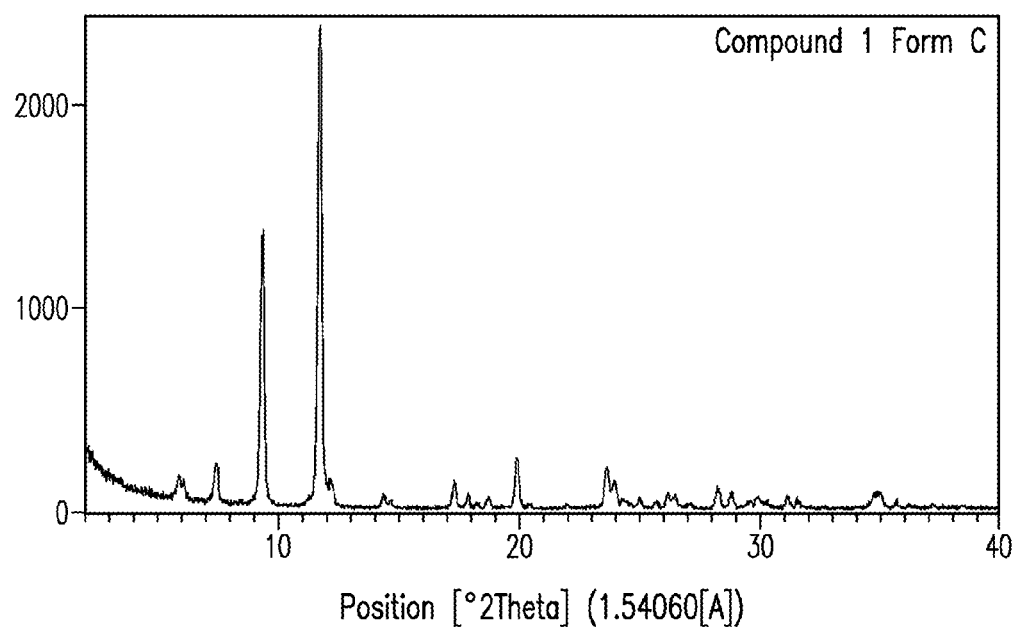
FIG. 12 depicts an X-ray powder diffractogram of Form C of Compound 1.

In one embodiment, provided herein is Form C of Compound 1. In one embodiment, Form C of Compound 1 is a hydrate. In another embodiment, Form C of Compound 1 is crystalline. In one embodiment, Form C of Compound 1 has an X-ray powder diffraction pattern substantially as shown in FIG. 12. In one embodiment, Form C of Compound 1 has one or more characteristic X-ray powder diffraction peaks at a two-theta angle of approximately 5.9, 6.1, 7.4, 9.3, 11.7, 12.2, 12.3, 14.4, 14.7, 17.3, 17.9, 18.3, 18.7, 19.9, 23.7, 24.0, 24.3, 25.0, 25.7, 26.2, 26.5, 27.1, 28.3, 28.4, 28.9, 29.6, 29.9, 30.3, 31.1, 31.6, 34.8 or 35.1 degrees. In a specific embodiment, Form C of Compound 1 has one, two, three, four, five, six, seven or eight characteristic X-ray powder diffraction peaks at a two-theta angle of approximately 5.9, 7.4, 9.3, 11.7, 12.2, 17.3, 19.9 or 23.7 degrees. In another embodiment, Form C of Compound 1 has one, two, three or four characteristic X-ray powder diffraction peaks at a two-theta angle of approximately 7.4, 9.3, 11.7 or 19.9 degrees. In another embodiment, Form C of Compound one has one, two, three, four, five, six, seven or eight characteristic X-ray powder diffraction peaks as set forth in Table 4.

Figure 13:
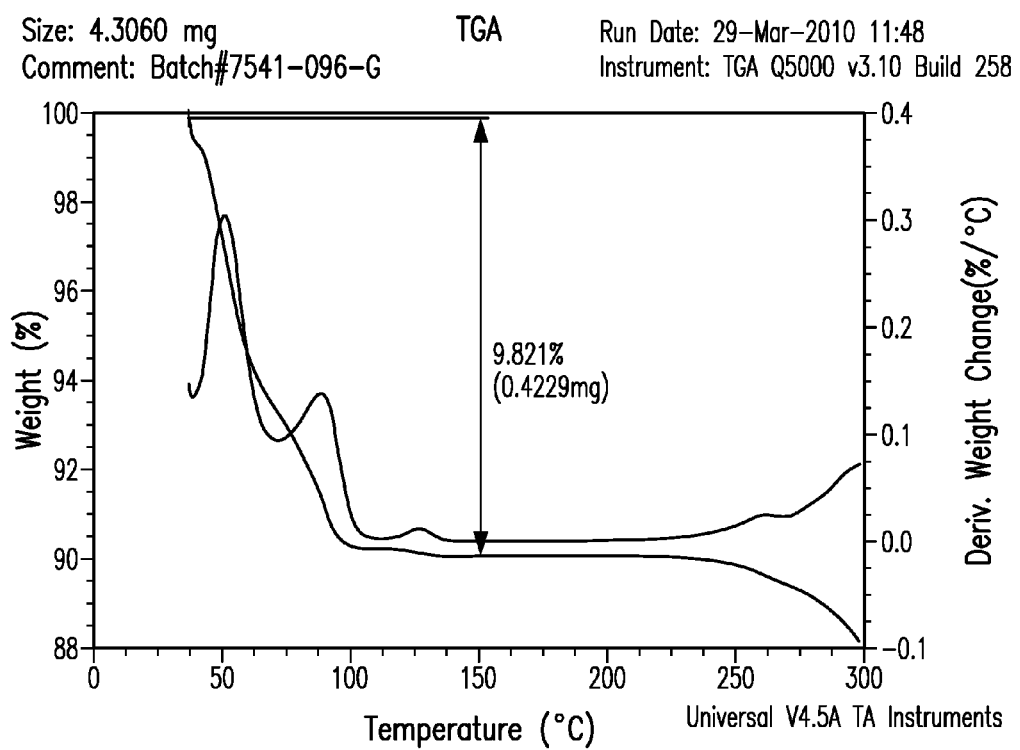
FIG. 13 depicts a thermogravimetric thermogram of Form C of Compound 1.

In another embodiment, Form C of Compound 1 has a thermogravimetric thermogram substantially as shown in FIG. 13. In certain embodiments, Form C of Compound 1 shows less than about 20%, less than about 15%, less than about 10% e.g., about 9.8%, weight loss between about 25° C. to about 100° C. in a thermogravimetric thermogram. In certain embodiments, Form C of Compound 1 shows less than about 10% weight loss between about 25° C. to about 100° C. in a thermogravimetric thermogram. In certain embodiments, Form C of Compound 1 is a di-hydrate. In certain embodiments, Form C of Compound 1 is unsolvated.

Figure 14:
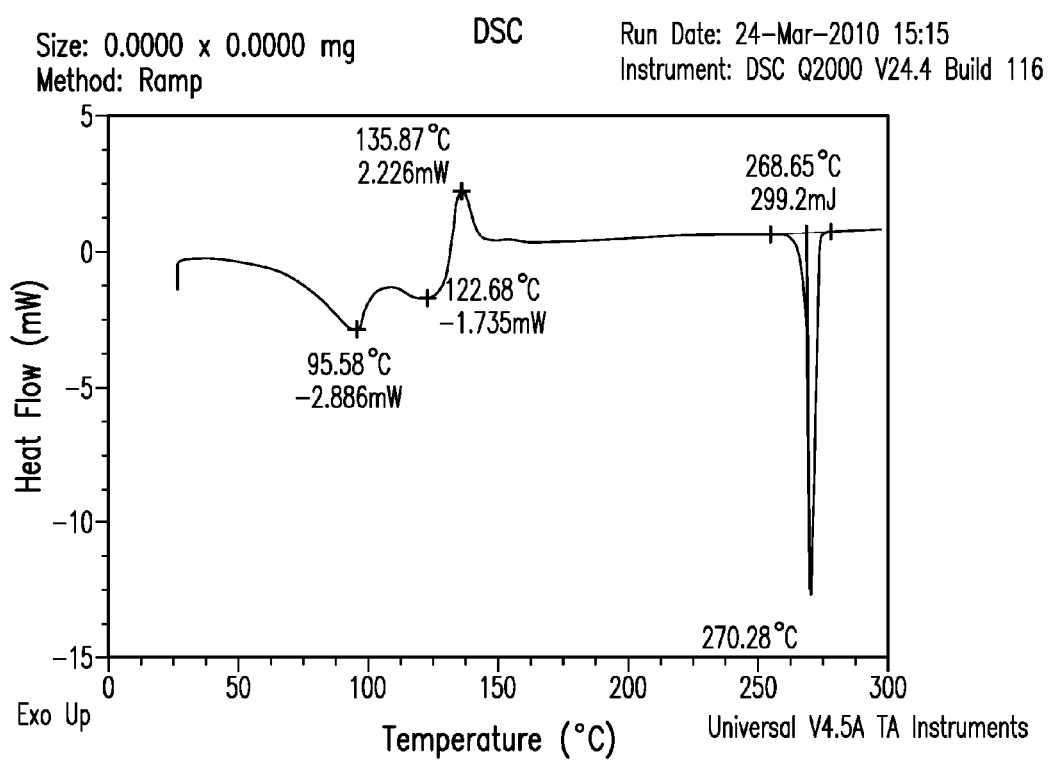
FIG. 14 depicts a differential scanning calorimetric thermogram of Form C of Compound 1.

In yet another embodiment, Form C of Compound 1 has a differential scanning calorimetric (DSC) thermogram substantially as shown in FIG. 14. In certain embodiments, Form C of Compound 1 has an endotherm with a peak temperature of about 268° C. in a DSC thermogram. In certain embodiments, Form C of Compound 1 has an endotherm with an onset temperature of about 265° C. in a DSC thermogram. In certain embodiments, Form C of Compound 1 has an endotherm with a peak temperature of about 268° C. and an onset temperature of about 265° C. in a DSC thermogram. In one embodiment, Form C of Compound 1 has a melting temperature of about 265-268° C. In certain embodiment, Form C of Compound 1 has a melting temperature of about 268° C.

Figure 15:
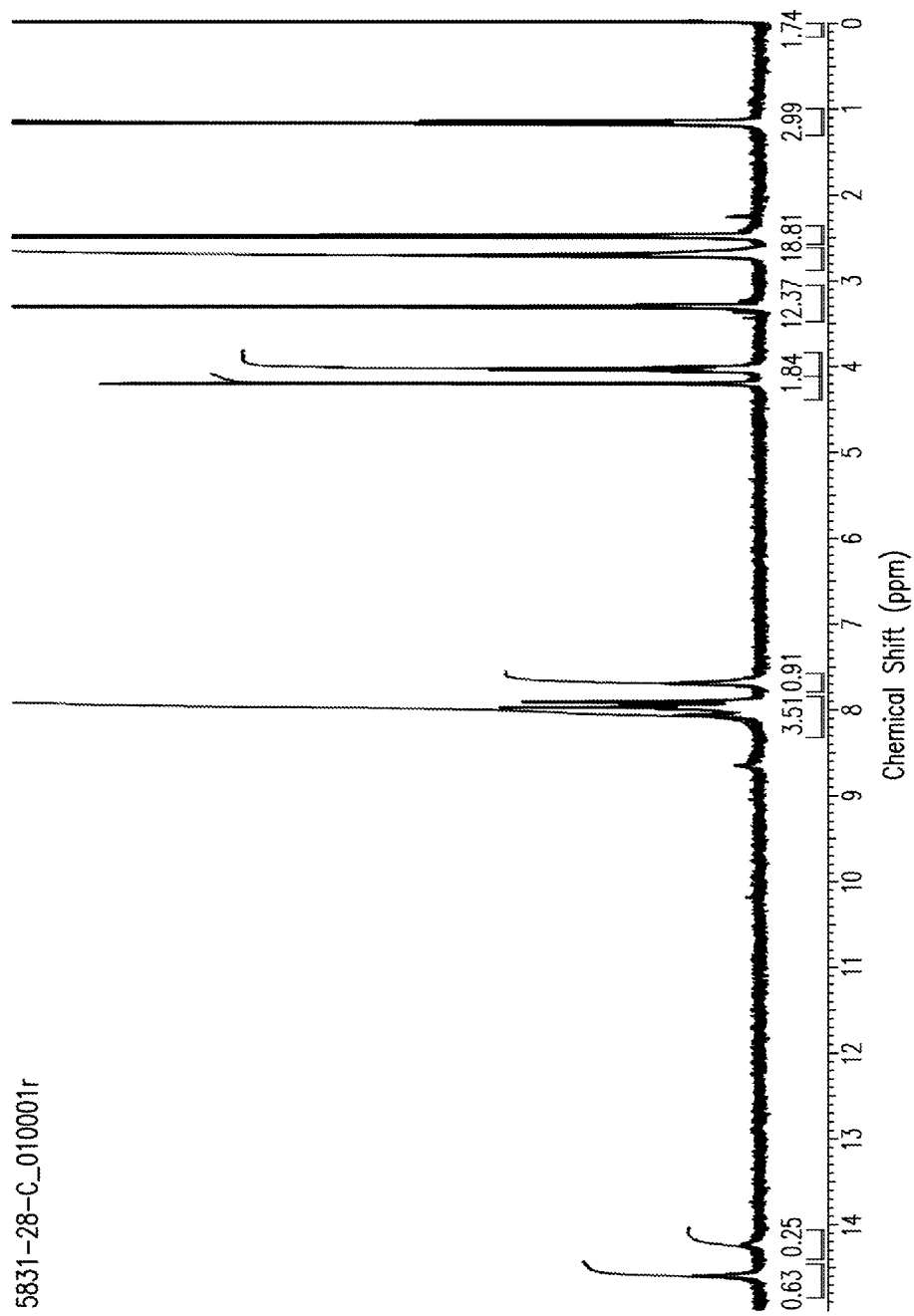
FIG. 15 depicts the $^1$H NMR Spectrum of Form C of Compound 1.

In another embodiment, Form C of Compound 1 has a $^1$H NMR spectrum substantially as shown in FIG. 15.

Figure 16:
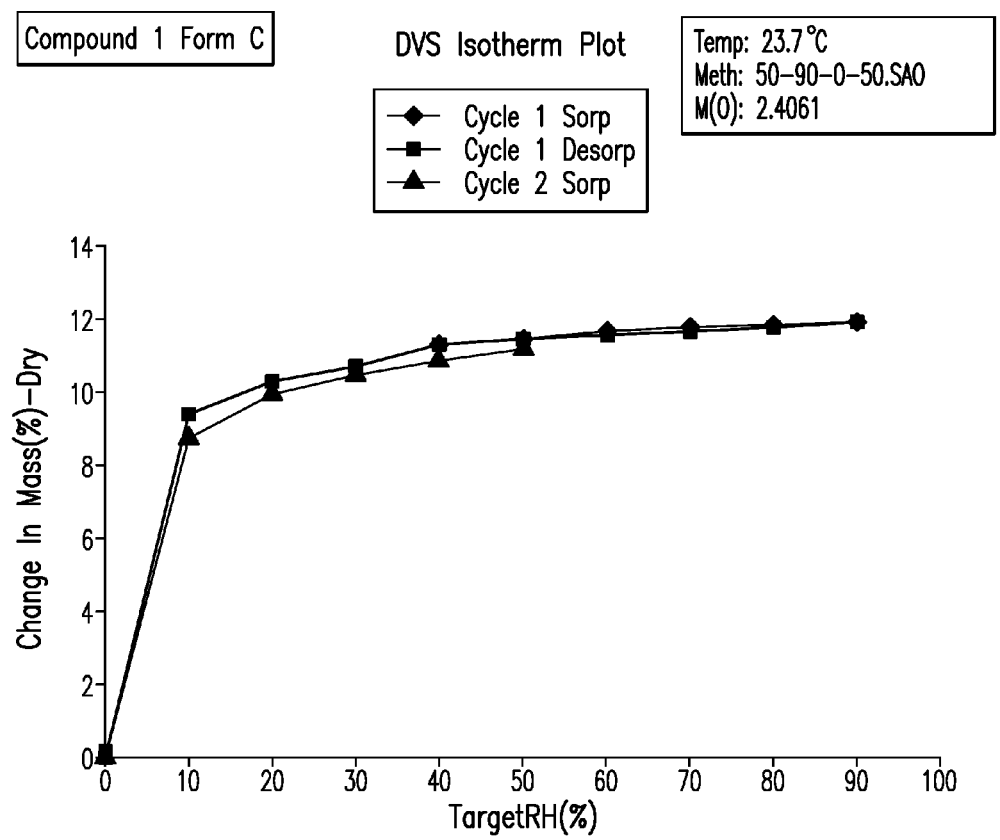
FIG. 16 depicts a dynamic vapor sorption plot of Form C of Compound 1.

In yet another embodiment, Form C of Compound 1 has a dynamic vapor sorption (DVS) plot substantially as shown in FIG. 16.

In still another embodiment, Form C of Compound 1 is substantially pure. In certain embodiments, the substantially pure Form C of Compound 1 is substantially free of other solid forms, e.g., amorphous form. In certain embodiments, the purity of the substantially pure Form C of Compound 1 is no less than about 95%, no less than about 96%, no less than about 97%, no less than about 98%, no less than about 98.5%, no less than about 99%, no less than about 99.5%, or no less than about 99.8%.

Figure 17:
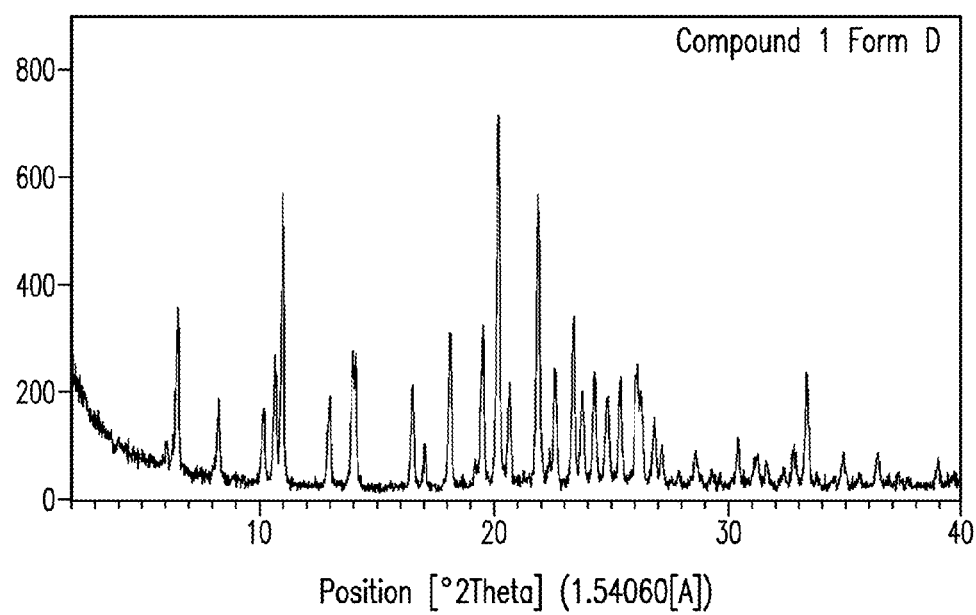
FIG. 17 depicts an X-ray powder diffractogram of Form D of Compound 1.

In one embodiment, provided herein is Form D of Compound 1. In one embodiment, Form D of Compound 1 is a DMSO solvate. In another embodiment, Form D of Compound 1 is crystalline. In one embodiment, Form D of Compound 1 has an X-ray powder diffraction pattern substantially as shown in FIG. 17. In one embodiment, Form D of Compound 1 has one or more characteristic X-ray powder diffraction peaks at a two-theta angle of approximately 6.1, 6.5, 8.3, 10.2, 10.7, 11.0, 13.0, 14.0, 14.1, 16.6, 17.1, 18.2, 19.2, 19.6, 20.2, 20.7, 21.9, 22.7, 23.4, 23.8, 24.3, 24.8, 24.9, 25.4, 26.1, 26.3, 26.9, 27.2, 27.9, 28.6, 29.4, 29.7, 30.5, 31.3, 31.7, 32.4, 32.8, 33.4, 33.8, 34.2, 35.0, 35.7, 36.4, 37.3 or 39.0 degrees. In a specific embodiment, Form D of Compound 1 has one, two, three, four, five, six, seven or eight characteristic X-ray powder diffraction peaks at a two-theta angle of approximately 6.5, 11.0, 14.0, 18.2, 19.6, 20.2, 21.9 or 23.4 degrees. In another embodiment, Form D of Compound 1 has one, two, three or four characteristic X-ray powder diffraction peaks at a two-theta angle of approximately 11.0, 20.2, 21.9 or 23.4 degrees. In another embodiment, Form C of Compound one has one, two, three, four, five, six, seven or eight characteristic X-ray powder diffraction peaks as set forth in Table 5.

Figure 18:
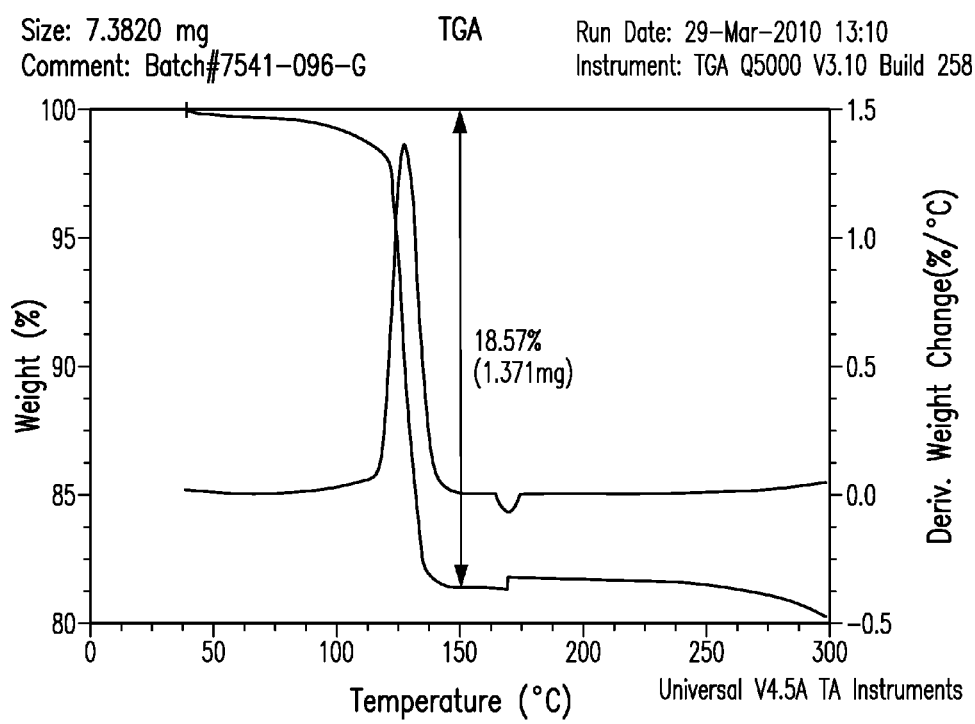
FIG. 18 depicts a thermogravimetric thermogram of Form D of Compound 1.

In another embodiment, Form D of Compound 1 has a thermogravimetric thermogram substantially as shown in FIG. 18. In certain embodiments, Form D of Compound 1 shows less than about 30%, less than about 25%, less than about 20%, e.g., about 19%, weight loss between about 25° C. to about 150° C. in a thermogravimetric thermogram. In certain embodiments, Form D of Compound 1 shows less than about 20% weight loss between about 25° C. to about 150° C. in a thermogravimetric thermogram. In certain embodiments, Form D of Compound 1 shows no weight loss until degradation at about 120° C. in a thermogravimetric thermogram. In certain embodiments, Form D of Compound 1 is a solvate.

Figure 19:
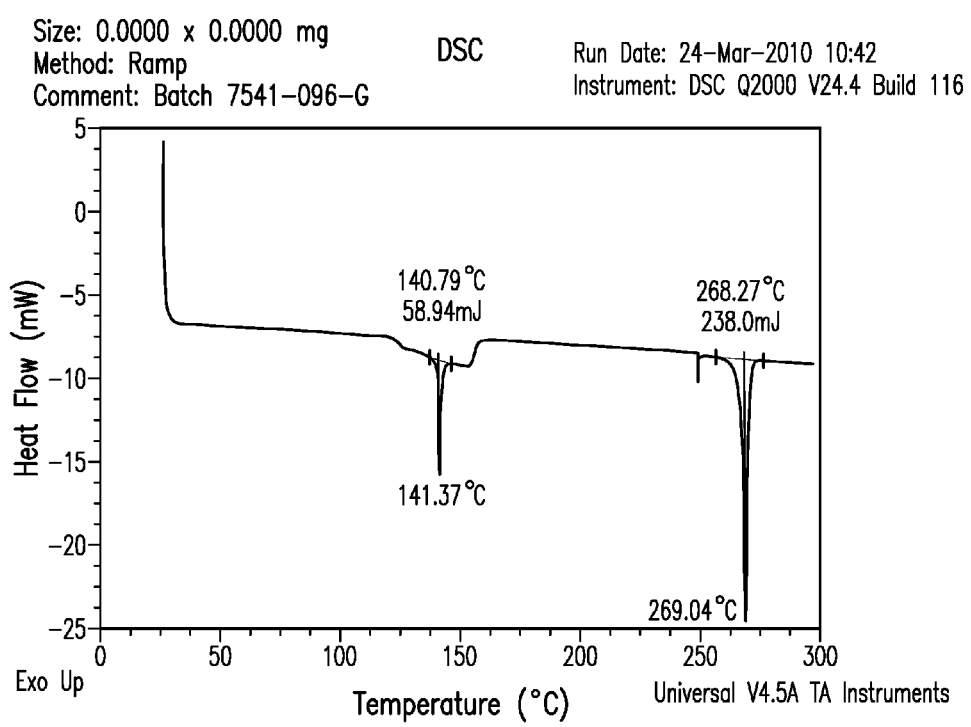
FIG. 19 depicts a differential scanning calorimetric thermogram of Form D of Compound 1.

In yet another embodiment, Form D of Compound 1 has a differential scanning calorimetric (DSC) thermogram substantially as shown in FIG. 19. In certain embodiments, Form D of Compound 1 has an endotherm with a peak temperature of about 269° C. in a DSC thermogram. In certain embodiments, Form D of Compound 1 has an endotherm with an onset temperature of about 268° C. in a DSC thermogram. In certain embodiments, Form D of Compound 1 has an endotherm with a peak temperature of about 269° C. and an onset temperature of about 268° C. in a DSC thermogram. In one embodiment, Form D of Compound 1 has a melting temperature of about 268-269° C. In certain embodiment, Form D of Compound 1 has a melting temperature of about 269° C.

Figure 20:
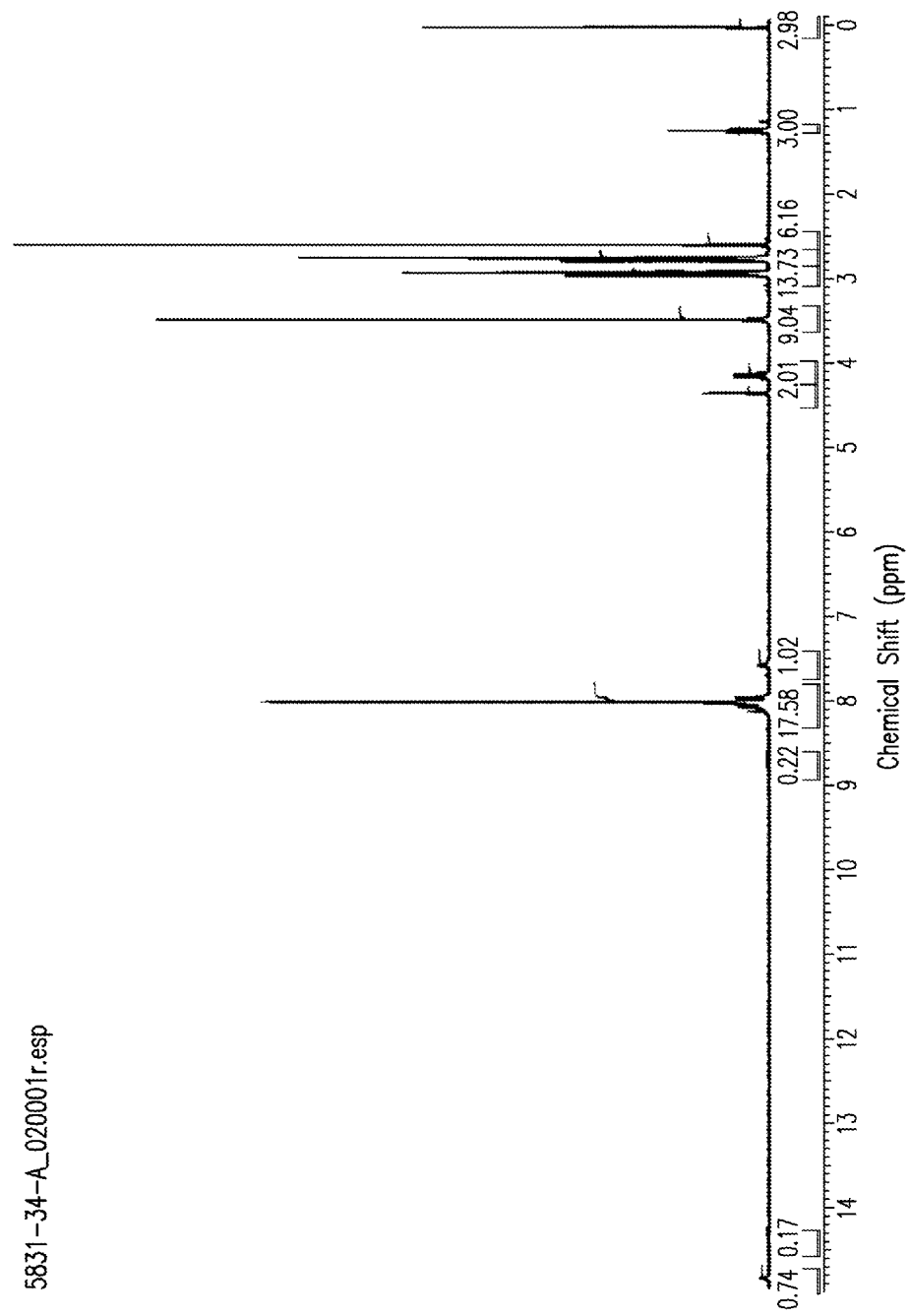
FIG. 20 depicts the $^1$H NMR Spectrum of Form D of Compound 1.

In another embodiment, Form D of Compound 1 has a $^1$H NMR spectrum substantially as shown in FIG. 20.

In still another embodiment, Form D of Compound 1 is substantially pure. In certain embodiments, the substantially pure Form D of Compound 1 is substantially free of other solid forms, e.g., amorphous form. In certain embodiments, the purity of the substantially pure Form D of Compound 1 is no less than about 95%, no less than about 96%, no less than about 97%, no less than about 98%, no less than about 98.5%, no less than about 99%, no less than about 99.5%, or no less than about 99.8%.

Figure 21:
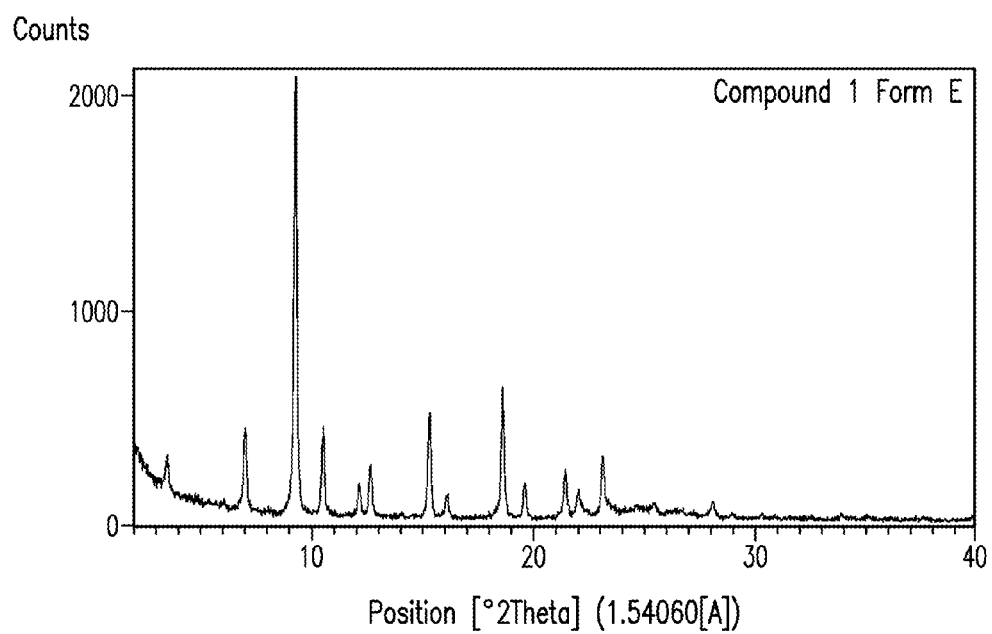
FIG. 21 depicts an X-ray powder diffractogram of Form E of Compound 1.

In one embodiment, provided herein is Form E of Compound 1. In one embodiment, Form E of Compound 1 is a hydrate. In another embodiment, Form E of Compound 1 is crystalline. In one embodiment, Form E of Compound 1 has an X-ray powder diffraction pattern substantially as shown in FIG. 21. In one embodiment, Form E of Compound 1 has one or more characteristic X-ray powder diffraction peaks at a two-theta angle of approximately 3.5, 7.0, 9.3, 10.5, 12.1, 12.7, 15.3, 16.1, 18.6, 19.6, 21.5, 22.1, 23.2, 24.7, 25.5, 26.5 or 28.1 degrees. In a specific embodiment, Form E of Compound 1 has one, two, three, four, five, six, seven or eight characteristic X-ray powder diffraction peaks at a two-theta angle of approximately 7.0, 9.3, 10.5, 12.7, 15.3, 18.6, 21.5 or 23.2 degrees. In another embodiment, Form E of Compound 1 has one, two, three or four characteristic X-ray powder diffraction peaks at a two-theta angle of approximately 9.3, 10.5, 15.3 or 18.6 degrees. In another embodiment, Form E of Compound one has one, two, three, four, five, six, seven or eight characteristic X-ray powder diffraction peaks as set forth in Table 6.

Figure 22:
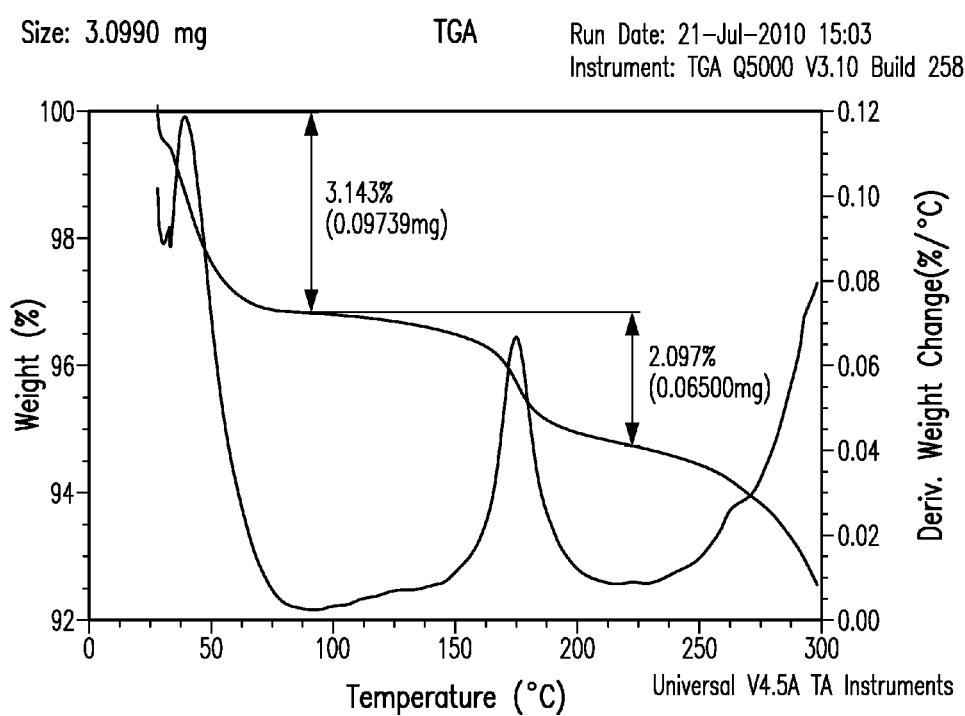
FIG. 22 depicts a thermogravimetric thermogram of Form E of Compound 1.

In another embodiment, Form E of Compound 1 has a thermogravimetric thermogram substantially as shown in FIG. 22. In certain embodiments, Form E of Compound 1 shows less than about 10%, less than about 5%, less than about 4%, e.g., about 3.1%, weight loss between about 25° C. to about 100° C. in a thermogravimetric thermogram. In certain embodiments, Form E of Compound 1 shows less than about 3.2% weight loss between about 25° C. to about 100° C. in a thermogravimetric thermogram. In certain embodiments, Form E of Compound 1 shows about 3.1% weight loss between about 25° C. to about 100° C. in a thermogravimetric thermogram. In certain embodiments, Form E of Compound 1 is a hydrate. In certain embodiments, Form E of Compound 1 is unsolvated.

Figure 23:
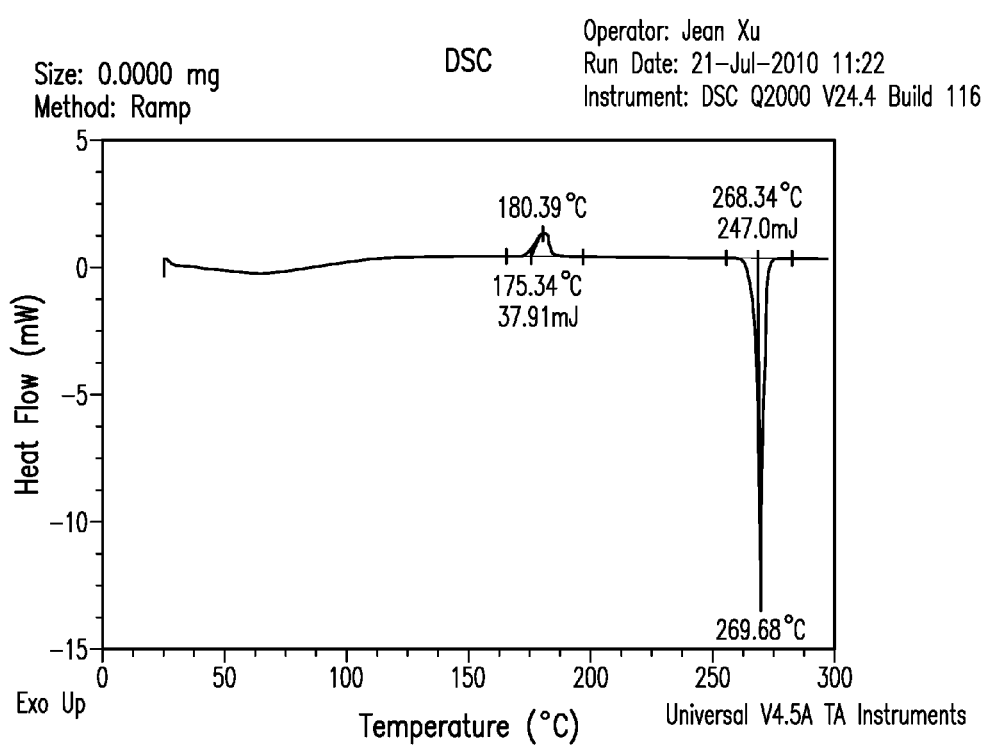
FIG. 23 depicts a differential scanning calorimetric thermogram of Form E of Compound 1.

In yet another embodiment, Form E of Compound 1 has a differential scanning calorimetric (DSC) thermogram substantially as shown in FIG. 23. In certain embodiments, Form E of Compound 1 has an endotherm with a peak temperature of about 270° C. in a DSC thermogram. In certain embodiments, Form E of Compound 1 has an endotherm with an onset temperature of about 268° C. in a DSC thermogram. In certain embodiments, Form E of Compound 1 has an endotherm with a peak temperature of about 270° C. and an onset temperature of about 268° C. in a DSC thermogram. In one embodiment, Form E of Compound 1 has a melting temperature of about 268-270° C. In certain embodiment, Form E of Compound 1 has a melting temperature of about 270° C.

Figure 24:
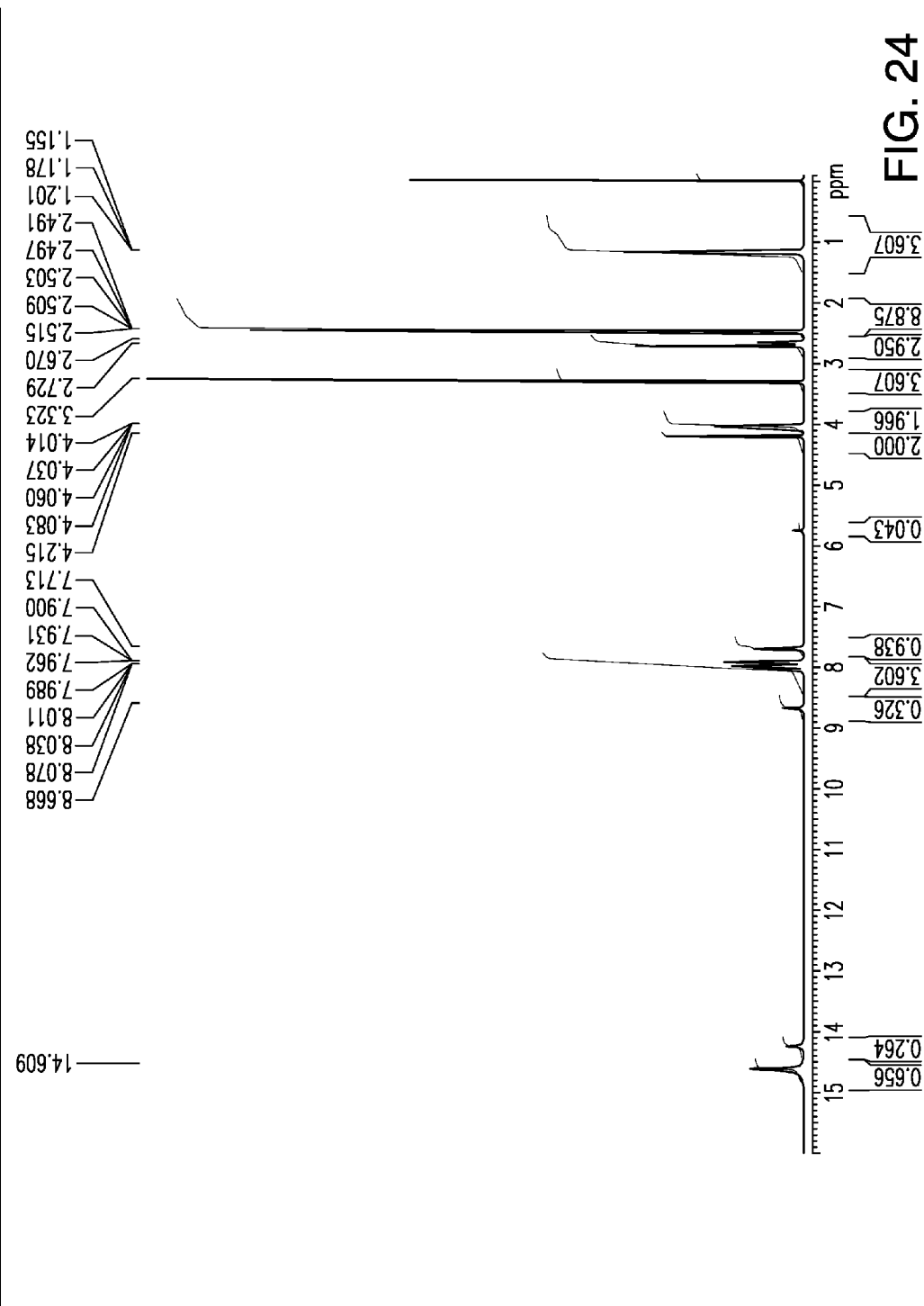
FIG. 24 depicts the $^1$H NMR Spectrum of Form E of Compound 1.

In another embodiment, Form E of Compound 1 has a $^1$H NMR spectrum substantially as shown in FIG. 24.

Figure 25:
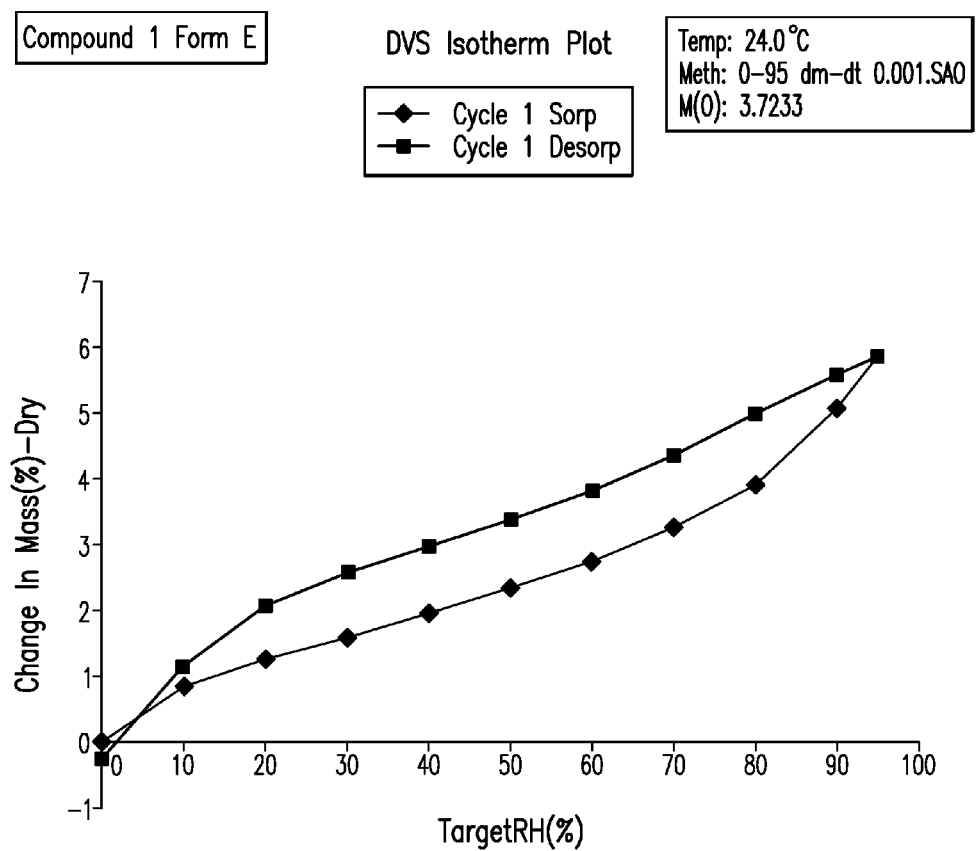
FIG. 25 depicts a dynamic vapor sorption plot of Form E of Compound 1.

In yet another embodiment, Form E of Compound 1 has a dynamic vapor sorption (DVS) plot substantially as shown in FIG. 25. In yet another embodiment, Form E of Compound 1 is non-hygroscopic, e.g., exhibits a mass gain of less than about 4% w/w of when subjected to an increase in humidity from about 0% to about 80% relative humidity (RH). In another embodiment, Form E of Compound exhibits a mass gain of about 1.1% w/w of when subjected to an increase in humidity from about 80% to about 90% relative humidity. In certain embodiments, Form E of Compound 1 exhibits no greater than about 10% w/w, no greater than about 7% w/w, no greater than about 6% w/w weight gain in response to an increase in humidity from about 0% to about 95% relative humidity at about 25° C. In certain embodiments, Form E of Compound 1 exhibits about 5.8% w/w weight gain in response to an increase in humidity from about 0% to about 95% relative humidity at about 25° C. In certain embodiments, Form E of Compound 1 exhibits no greater than about 10% w/w, no greater than about 5% w/w, no greater than about 46% w/w, no greater than about 3% w/w weight gain in response to an increase in humidity from about 0% to about 50% relative humidity at about 25° C. In certain embodiments, Form E of Compound 1 exhibits about 2.3% w/w weight gain in response to an increase in humidity from about 0% to about 50% relative humidity at about 25° C.

In still another embodiment, Form E of Compound 1 is substantially pure. In certain embodiments, the substantially pure Form E of Compound 1 is substantially free of other solid forms, e.g., amorphous form. In certain embodiments, the purity of the substantially pure Form E of Compound 1 is no less than about 95%, no less than about 96%, no less than about 97%, no less than about 98%, no less than about 98.5%, no less than about 99%, no less than about 99.5%, or no less than about 99.8%.

In certain embodiments, provided herein are methods for making Form A of Compound 1, comprising dissolving Compound 1 in DMF, heating and then cooling to room temperature, collecting solids by filtration, washing and drying. Further methods for making Form A are set forth in the examples provided herein.

In certain embodiments, provided herein are methods for making Form B of Compound 1, comprising dissolving Compound 1 in MeOH, heating and then cooling to room temperature, collecting solids by filtration, washing and drying. In certain embodiments, provided herein are methods for making Form B of Compound 1, comprising dissolving Compound 1 in MeOH at approximately 50° C.-70° C., rapidly cooling the solution (such as by placing into a refrigerator), collecting solids by filtration after about 24 hours and air drying.

In certain embodiments, provided herein are methods for making Form C of Compound 1, comprising dissolving Compound 1 in a mixture of MeOH and $H_2O$ (1:1), heating and then cooling to room temperature, collecting solids by filtration, washing and drying. In certain embodiments, provided herein are methods for making Form C of Compound 1, comprising dissolving Compound 1 in a mixture of MeOH and $H_2O$ (1:1) at approximately 50° C.-70° C., rapidly cooling the solution (such as by placing into a refrigerator), collecting solids by filtration after about 24 hours and air drying.

In certain embodiments, provided herein are methods for making Form C of Compound 1, comprising dissolving Compound 1 in a mixture of EtOH and $H_2O$ (1:1), heating and then cooling to room temperature, collecting solids by filtration, washing and drying. In certain embodiments, provided herein are methods for making Form C of Compound 1, comprising dissolving Compound 1 in a mixture of EtOH and $H_2O$ (1:1) at approximately 50° C.-70° C., rapidly cooling the solution (such as by placing into a refrigerator), collecting solids by filtration after about 24 hours and air drying.

In certain embodiments, provided herein are methods for making Form D of Compound 1, comprising dissolving Compound 1 in DMSO, adding MTBE, stirring the slurry, collecting solids by filtration, washing and drying. In certain embodiments, provided herein are methods for making Form D of Compound 1, comprising completely dissolving Compound 1 in DMSO at room temperature, adding MTBE to the mixture with stirring overnight, collecting the solids by filtration and air drying.

In certain embodiments, provided herein are methods for making Form E of Compound 1, comprising obtaining a slurry of Compound 1 in a 1:1 mixture of MeOH and DCM, stirring the slurry, collecting by filtration (such as centrifuge filtration), optionally washing and drying.

Pharmaceutically acceptable salts of the Heteroaryl Compounds can be formed by conventional and known techniques, such as by reacting a Heteroaryl Compound with a suitable acid as disclosed above. Such salts are typically formed in high yields at moderate temperatures, and often are prepared by merely isolating the compound from a suitable acidic wash in the final step of the synthesis. The salt-forming acid may dissolved in an appropriate organic solvent, or aqueous organic solvent, such as an alkanol, ketone or ester. On the other hand, if the Heteroaryl Compound is desired in the free base form, it may be isolated from a basic final wash step, according to known techniques. For example, a typical technique for preparing hydrochloride salt is to dissolve the free base in a suitable solvent, and dry the solution thoroughly, as over molecular sieves, before bubbling hydrogen chloride gas through it.

5.5 Methods of Use

Provided herein are methods for treating or preventing a cancer, comprising administering a formulation of Compound 1 provided herein to a patient having a cancer.

In some embodiments, the cancer is an advanced unresectable solid tumor, or a hematologic malignancy. For example, the hematologic malignancy is CLL, NHL, or MM. In some such embodiments, the cancer has progressed on standard anti-cancer therapy, or the patient is not able to tolerate standard anti-cancer therapy. In yet others, the cancer is a cancer for which no approved therapy exists. In some embodiments, the cancer is resistant to standard therapy. In another, the patient has relapsed after standard therapy. In one embodiment, the cancer is a neoplasm metastasis.

In certain embodiments, the cancer is a bloodborne tumor.

In certain embodiments, the cancer is a lymphoma, a leukemia or a multiple myeloma.

In certain embodiments, the cancer is non-Hodgkin's lymphoma. In certain embodiments, the non-Hodgkin's lymphoma is diffuse large B-cell lymphoma (DLBCL), follicular lymphoma (FL), acute myeloid leukemia (AML), mantle cell lymphoma (MCL), or ALK$^+$ anaplastic large cell lymphoma. In one embodiment, the non-Hodgkin's lymphoma is advanced solid non-Hodgkin's lymphoma. In one embodiment, the non-Hodgkin's lymphoma is diffuse large B-cell lymphoma (DLBCL).

In certain embodiments, the cancer is a B-cell lymphoma.

In certain embodiments, the B-cell lymphoma is a B-cell non-Hodgkin's lymphoma selected from diffuse large B-cell lymphoma, Burkitt's lymphoma/leukemia, mantle cell lymphoma, mediastinal (thymic) large B-cell lymphoma, follicular lymphoma, marginal zone lymphoma (including extranodal marginal zone B-cell lymphoma and nodal marginal zone B-cell lymphoma), lymphoplasmacytic lymphoma/Waldenstrom macroglobulinemia. In some embodiments, the B-cell lymphoma is chronic lymphocytic leukemia/small lymphocytic lymphoma (CLL/SLL). In one embodiment, the B-cell lymphoma is Waldenstrom macroglobulinemia.

In one embodiment, the cancer is T-cell prolymphocytic leukemia (T-PLL).

In one embodiment, the B-cell non-Hodgkin's lymphoma is refractory B-cell non-Hodgkin's lymphoma. In one embodiment, the B-cell non-Hodgkin's lymphoma is relapsed B-cell non-Hodgkin's lymphoma.

In certain embodiments, the cancer is a T-cell lymphoma.

The B-cell disorders chronic lymphocytic leukemia/small lymphocytic lymphoma (CLL/SLL) represent 2 ends of a spectrum of the same disease process differing in the degree of blood/marrow involvement (CLL) versus lymph node involvement (SLL).

In another embodiment, the cancer is CLL characterized by deletion of chromosome 11q22, loss of ATM expression, mutation of IgVH, wild type IgVH, wild type p53/ATM, mutation of p53 or dysfunctional p53.

In another embodiment, the cancer is T-PLL characterized by deletion of chromosome 11q22, loss of ATM expression, mutation of IgVH, wild type IgVH, wild type p53/ATM, mutation of p53 or dysfunctional p53.

In other embodiments, the cancer is a multiple myeloma.

In certain embodiments, the cancer is a cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

In other embodiments, the cancer is a solid tumor. In certain embodiments, the solid tumor is a relapsed or refractory solid tumor.

In one embodiment, the solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In certain embodiments, the neuroendocrine tumor is a symptomatic endocrine producing tumor or a nonfunctional tumor. In certain embodiments, the neuroendocrine tumor is locally unresectable, metastatic moderate, well differentiated, low (grade 1) or intermediate (grade 2).

In one embodiment, the solid tumor is non-small cell lung cancer (NSCLC).

In another embodiments the solid tumor is glioblastoma multiforme (GBM).

In another embodiment, the solid tumor is hepatocellular carcinoma (HCC).

In another embodiment, the solid tumor is breast cancer. In one embodiment, the breast cancer is hormone receptor positive. In one embodiment, the breast cancer is estrogen receptor positive (ER+, ER+/Her2 or ER+/Her2+). In one embodiment, the breast cancer is estrogen receptor negative (ER−/Her2+). In one embodiment, the breast cancer is triple negative (TN) (breast cancer that does not express the genes and/or protein corresponding to the estrogen receptor (ER), progesterone receptor (PR), and that does not overexpress the Her2/neu protein).

In one embodiment, the solid tumor is an advanced solid tumor.

In another embodiment, the cancer is head and neck squamous cell carcinoma.

In another embodiment, the cancer is E-twenty six (ETS) overexpressing castration-resistant prostate cancer.

In another embodiment, the cancer is E-twenty six (ETS) overexpressing Ewings sarcoma.

In another embodiment, the cancer is head and neck squamous cell carcinoma (HNSCC) characterized by deletion of chromosome 11q22 or loss of ataxia telangiectasia mutated (ATM) expression.

In another embodiment, the cancer is glioblastoma multiforme (GBM) characterized by O6-methylguanine-DNA methyltransferase (MGMT) methylation.

In other embodiments, the cancer is a cancer associated with the pathways involving mTOR, PI3K, or Akt kinases and mutants or isoforms thereof. Other cancers within the scope of the methods provided herein include those associated with the pathways of the following kinases: PI3Kα, PI3Kβ, PI3Kδ, KDR, GSK3α, GSK3β, ATM, ATX, ATR, cFMS, and/or DNA-PK kinases and mutants or isoforms thereof. In some embodiments, the cancers associated with mTOR/PI3K/Akt pathways include solid and blood-borne tumors, for example, multiple myeloma, mantle cell lymphoma, diffused large B-cell lymphoma, acute myeloid lymphoma, follicular lymphoma, chronic lymphocytic leukemia; and solid tumors, for example, breast, lung, endometrial, ovarian, gastric, cervical, and prostate cancer; glioblastoma; renal carcinoma; hepatocellular carcinoma; colon carcinoma; neuroendocrine tumors; head and neck tumors; and sarcomas, such as Ewing's sarcoma.

In certain embodiments, provided herein are methods for achieving a Response Evaluation Criteria in Solid Tumors (for example, RECIST 1.1) of complete response, partial response or stable disease in a patient having a solid tumor, comprising administering a formulation of Compound 1 provided herein to said patient. In certain embodiments, provided herein are methods for achieving a National Cancer Institute-Sponsored Working Group on Chronic Lymphocytic Leukemia (NCI-WG CLL) of complete response, partial response or stable disease in a patient having leukemia, comprising administering a formulation of Compound 1 provided herein to said patient. In certain embodiments, provided herein are methods for achieving a Prostate Cancer Working Group 2 (PCWG2) Criteria of complete response, partial response or stable disease in a patient having prostate cancer, comprising administering a formulation of Compound 1 provided herein to said patient. In certain embodiments, provided herein are methods for achieving an International Workshop Criteria (IWC) for non-Hodgkin's lymphoma of complete response, partial response or stable disease in a patient having non-Hodgkin's lymphoma, comprising administering a formulation of Compound 1 provided herein to said patient. In certain embodiments, provided herein are methods for achieving an International Uniform Response Criteria (IURC) for multiple myeloma of complete response, partial response or stable disease in a patient having multiple myeloma, comprising administering a formulation of Compound 1 provided herein to said patient. In certain embodiments, provided herein are methods for achieving a Responses Assessment for Neuro-Oncology (RANO) Working Group for glioblastoma multiforme of complete response, partial response or stable disease in a patient having glioblastoma multiforme, comprising administering a formulation of Compound 1 provided herein to said patient.

In certain embodiments, provided herein are methods for increasing survival without disease progression of a patient having a cancer, comprising administering a formulation of Compound 1 provided herein to said patient.

In certain embodiments, provided herein are methods for treating a cancer, the methods comprising administering a formulation of Compound 1 provided herein to a patient having a cancer, wherein the treatment results in prevention or retarding of clinical progression, such as cancer-related cachexia or increased pain.

In some embodiments, provided herein are methods for treating a cancer, the methods comprising administering a formulation of Compound 1 provided herein to a patient having a cancer, wherein the treatment results in one or more of inhibition of disease progression, increased Time To Progression (TTP), increased Progression Free Survival (PFS), and/or increased Overall Survival (OS), among others.

5.6 Pharmaceutical Compositions

Compound 1 made by the processes provided herein is useful for the preparation of pharmaceutical compositions, comprising an effective amount of Compound 1 and a pharmaceutically acceptable carrier or vehicle. In some embodiments, the pharmaceutical composition described herein are suitable for oral, parenteral, mucosal, transdermal or topical administration.

In one embodiment, the pharmaceutical compositions provided herein comprise Compound 1 and one or more pharmaceutically acceptable excipients or carriers. In one embodiment, the pharmaceutical compositions provided herein comprise Form A of Compound 1 and one or more pharmaceutically acceptable excipients or carriers. In one embodiment, the pharmaceutical compositions provided herein comprise Form B of Compound 1 and one or more pharmaceutically acceptable excipients or carriers. In one embodiment, the pharmaceutical compositions provided herein comprise Form C of Compound 1 and one or more pharmaceutically acceptable excipients or carriers. In one embodiment, the pharmaceutical compositions provided herein comprise Form D of Compound 1 and one or more pharmaceutically acceptable excipients or carriers. In one embodiment, the pharmaceutical compositions provided herein comprise Form E of Compound 1 and one or more pharmaceutically acceptable excipients or carriers.

In one embodiment, the pharmaceutical compositions provided herein comprise pharmaceutically acceptable salts, tautomers, isotopologues, metabolites and stereoisomers of Compound 1 and one or more pharmaceutically acceptable excipients or carriers.

In one embodiment, the pharmaceutically acceptable excipients and carriers are selected from binders, diluents, disintegrants and lubricants. In another embodiment, the pharmaceutically acceptable excipients and carriers further include one or more antioxidants (e.g. EDTA or BHT).

In certain embodiments, the binders include, but are not limited to, cellulose (e.g., microcrystalline cellulose, such as AVICEL® PH 101 and AVICEL® PH 102) and starch (e.g., pregelatinized starch (STARCH 1500®)). In one embodiment, the binder is cellulose. In another embodiment, the binder is microcrystalline cellulose. In yet another embodiment, the binder is AVICEL® PH 101. In yet another embodiment, the binder is AVICEL® PH 102. In yet another embodiment, the binder is starch. In yet another embodiment, the binder is pregelatinized starch. In still another embodiment, the binder is STARCH 1500®.

In certain embodiments, the diluents include, but are not limited to, lactose (e.g., lactose monohydrate (FAST FLO® 316) and lactose anhydrous), cellulose (e.g., microcrystalline cellulose, such as AVICEL® PH 101 and AVICEL® PH 102). In one embodiment, the diluent is lactose. In another embodiment, the diluent is lactose monohydrate. In yet another embodiment, the diluent is FAST FLO® 316. In yet another embodiment, the diluent is lactose anhydrous. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102).

In certain embodiments, the disintegrants include, but are not limited to, starch (e.g., corn starch) and carboxymethyl cellulose (e.g., croscarmellose sodium, such as AC-DI-SOL®). In one embodiment, the disintegrant is starch. In another embodiment, the disintegrant is corn starch. In yet another embodiment, the disintegrant is carboxymethyl cellulose. In yet another embodiment, the disintegrant is croscarmellose sodium. In still another embodiment, the disintegrant is AC-DI-SOL®.

In certain embodiments, the lubricants include, but are not limited to, starch (e.g., corn starch), magnesium stearate, and stearic acid. In one embodiment, the lubricant is starch. In another embodiment, the lubricant is corn starch. In yet another embodiment, the lubricant is magnesium stearate. In still another embodiment, the lubricant is stearic acid.

In another embodiment, the pharmaceutical compositions provided herein comprise Compound 1 and one or more pharmaceutically acceptable excipients or carriers, each independently selected from carboxymethylcellulose, cellulose, lactose, magnesium stearate, starch, stearic acid, mannitol, sodium starch glycolate, disodium EDTA, butylated hydroxy toluene (BHT), and silicon dioxide.

In another embodiment, the pharmaceutical compositions provided herein comprise Compound 1 and one or more pharmaceutically acceptable excipients or carriers, each independently selected from microcrystalline cellulose, lactose monohydrate, croscarmellose sodium, silicon dioxide, and magnesium stearate. In another embodiment, the pharmaceutical compositions provided herein comprise Compound 1 and one or more pharmaceutically acceptable excipients or carriers, each independently selected from microcrystalline cellulose, corn starch (for example, pregelatinized corn starch), crospovidone, silicon dioxide, and magnesium stearate. In another embodiment, the pharmaceutical compositions provided herein comprise Compound 1 and one or more pharmaceutically acceptable excipients or carriers, each independently selected from microcrystalline cellulose, lactose monohydrate, crospovidone, silicon dioxide, and magnesium stearate. In another embodiment, the pharmaceutical compositions provided herein comprise Compound 1 and one or more pharmaceutically acceptable excipients or carriers, each independently selected from microcrystalline cellulose, corn starch (for example, pregelatinized corn starch), croscarmellose sodium, silicon dioxide, and magnesium stearate.

In another embodiment, the pharmaceutical compositions provided herein comprise Compound 1 and one or more pharmaceutically acceptable excipients or carriers, each independently selected from mannitol, microcrystalline cellulose (for example, PH112), sodium starch glycolate, stearic acid, disodium EDTA, and magnesium stearate. In another embodiment, the pharmaceutical compositions provided herein comprise Compound 1 and one or more pharmaceutically acceptable excipients or carriers, each independently selected from mannitol, sodium starch glycolate, stearic acid, butylated hydroxy toluene, and magnesium stearate. In another embodiment, the pharmaceutical compositions provided herein comprise Compound 1 and one or more pharmaceutically acceptable excipients or carriers, each independently selected from microcrystalline cellulose (for example, PH112), sodium starch glycolate, stearic acid, butylated hydroxy toluene, and magnesium stearate. In another embodiment, the pharmaceutical compositions provided herein comprise Compound 1 and one or more pharmaceutically acceptable excipients or carriers, each independently selected from mannitol, sodium starch glycolate, stearic acid, butylated hydroxy toluene, disodium EDTA, and magnesium stearate. In another embodiment, the pharmaceutical compositions provided herein comprise Compound 1 and one or more pharmaceutically acceptable excipients or carriers, each independently selected from mannitol, microcrystalline cellulose (for example, PH112), sodium starch glycolate, stearic acid, butylated hydroxy toluene, disodium EDTA, and magnesium stearate. In another embodiment, the pharmaceutical compositions provided herein comprise Compound 1 and one or more pharmaceutically acceptable excipients or carriers, each independently selected from lactose, sodium starch glycolate, stearic acid, butylated hydroxy toluene, disodium EDTA, and magnesium stearate.

In another embodiment, the pharmaceutical compositions provided herein comprise Compound 1 and one or more pharmaceutically acceptable excipients or carriers, each independently selected from mannitol, microcrystalline cellulose (for example, PH112), sodium starch glycolate, stearic acid, butylated hydroxy toluene, disodium EDTA, and magnesium stearate.

In another embodiment, the pharmaceutical compositions provided herein comprise Compound 1 and one or more pharmaceutically acceptable excipients or carriers, each independently selected from mannitol, microcrystalline cellulose (for example, PH 112), sodium starch glycolate, silicon dioxide, stearic acid, and magnesium stearate. In another embodiment, the pharmaceutical compositions provided herein comprise Compound 1 and one or more pharmaceutically acceptable excipients or carriers, each independently selected from mannitol, microcrystalline cellulose (for example, PH 112), sodium starch glycolate, silicon dioxide, stearic acid, butylated hydroxy toluene, and magnesium stearate. In another embodiment, the pharmaceutical compositions provided herein comprise Compound 1 and one or more pharmaceutically acceptable excipients or carriers, each independently selected from mannitol, microcrystalline cellulose (for example, PH 112), sodium starch glycolate, silicon dioxide, stearic acid, disodium EDTA, and magnesium stearate. In another embodiment, the pharmaceutical compositions provided herein comprise Compound 1 and one or more pharmaceutically acceptable excipients or carriers, each independently selected from mannitol, microcrystalline cellulose (for example, PH 112), sodium starch glycolate, silicon dioxide, stearic acid, disodium EDTA, butylated hydroxy toluene, and magnesium stearate.

In another embodiment, the pharmaceutical compositions provided herein comprise Compound 1 and one or more pharmaceutically acceptable excipients or carriers, each independently selected from microcrystalline cellulose (for example, PH 102), mannitol, sodium carboxymethylcellulose, and magnesium stearate.

In another embodiment, the pharmaceutical compositions provided herein comprise Compound 1 and one or more pharmaceutically acceptable excipients or carriers, each independently selected from microcrystalline cellulose (for example, PH 102), pregelatinized starch, sodium carboxymethylcellulose, and magnesium stearate.

In another embodiment, the pharmaceutical compositions provided herein comprise Compound 1 and one or more pharmaceutically acceptable excipients or carriers, each independently selected from microcrystalline cellulose (for example, PH 102), lactose monohydrate, sodium carboxymethylcellulose, and magnesium stearate.

In another embodiment, the pharmaceutical compositions provided herein comprise Compound 1 and one or more pharmaceutically acceptable excipients or carriers, each independently selected from microcrystalline cellulose (for example, PH 102), mannitol, sodium carboxymethylcellulose, and magnesium stearate.

In another embodiment, the pharmaceutical compositions provided herein comprise Compound 1 and one or more pharmaceutically acceptable excipients or carriers, each independently selected from microcrystalline cellulose (for example, PH 102), pregelatinized starch, sodium carboxymethylcellulose, magnesium stearate.

In another embodiment, the pharmaceutical compositions provided herein comprise Compound 1 and one or more pharmaceutically acceptable excipients or carriers, each independently selected from microcrystalline cellulose (for example, PH 102), lactose monohydrate, sodium carboxymethylcellulose, and magnesium stearate.

In one embodiment, the pharmaceutical compositions provided herein comprise about 10-20% by weight of Compound 1, about 70-90% by weight of diluent(s)/binder(s), about 1-5% by weight of disintegrant(s), and about 0.1-2% by weight of lubricant(s).

In another embodiment, the pharmaceutical compositions provided herein comprise about 0.5% by weight of Compound 1 and about 63.75% by weight of microcrystalline cellulose, about 30% by weight of lactose monohydrate, about 4% by weight of croscarmellose sodium, about 1% by weight of silicon dioxide, and about 0.75% by weight of magnesium stearate. In another embodiment, the pharmaceutical compositions provided herein comprise about 0.5% by weight of Compound 1 and about 83.75% by weight of microcrystalline cellulose, about 10% by weight of corn starch (for example, pregelatinized corn starch), about 4% by weight of crospovidone, about 1% by weight of silicon dioxide, and about 0.75% by weight of magnesium stearate. In another embodiment, the pharmaceutical compositions provided herein comprise about 5% by weight of Compound 1 and about 59.25% by weight of microcrystalline cellulose, about 30% by weight of lactose monohydrate, about 4% by weight of crospovidone, about 1% by weight of silicon dioxide, and about 0.75% by weight of magnesium stearate. In another embodiment, the pharmaceutical compositions provided herein comprise about 5% by weight of Compound 1 and about 79.25% by weight of microcrystalline cellulose, about 10% by weight of corn starch (for example, pregelatinized corn starch), about 4% by weight of croscarmellose sodium, about 1% by weight of silicon dioxide, and about 0.75% by weight of magnesium stearate.

In another embodiment, the pharmaceutical compositions provided herein comprise about 0.5% by weight of Compound 1 and about 84% by weight of mannitol, about 10% by weight of microcrystalline cellulose (for example, PH112), about 3% by weight of sodium starch glycolate, about 1% by weight of stearic acid, about 0.5% by weight of disodium EDTA, and about 1% by weight of magnesium stearate. In another embodiment, the pharmaceutical compositions provided herein comprise about 0.5% by weight of Compound 1 and about 94.1% by weight of mannitol, about 3% by weight of sodium starch glycolate, about 1% by weight of stearic acid, about 0.4% by weight of butylated hydroxy toluene, and about 1% by weight of magnesium stearate. In another embodiment, the pharmaceutical compositions provided herein comprise about 0.5% by weight of Compound 1 and about 94.1% by weight of microcrystalline cellulose (for example, PH112), about 3% by weight of sodium starch glycolate, about 1% by weight of stearic acid, about 0.4% by weight of butylated hydroxy toluene, and about 1% by weight of magnesium stearate. In another embodiment, the pharmaceutical compositions provided herein comprise about 0.5% by weight of Compound 1 and one about 93.6% by weight of mannitol, about 3% by weight of sodium starch glycolate, about 1% by weight of stearic acid, about 0.4% by weight of butylated hydroxy toluene, about 0.5% by weight of disodium EDTA, and about 1% by weight of magnesium stearate. In another embodiment, the pharmaceutical compositions provided herein comprise about 0.5% by weight of Compound 1 and about 83.6% by weight of mannitol, about 10% by weight of microcrystalline cellulose (for example, PH112), about 3% by weight of sodium starch glycolate, about 1% by weight of stearic acid, about 0.4% by weight of butylated hydroxy toluene, about 0.5% by weight of disodium EDTA, and about 1% by weight of magnesium stearate. In another embodiment, the pharmaceutical compositions provided herein comprise about 0.5% by weight of Compound 1 and about 93.6% by weight of lactose, about 3% by weight of sodium starch glycolate, about 1% by weight of stearic acid, about 0.4% by weight of butylated hydroxy toluene, about 0.5% by weight of disodium EDTA, and about 1% by weight of magnesium stearate.

In another embodiment, the pharmaceutical compositions provided herein comprise about 0.5% by weight of Compound 1 and about 83.6% by weight of mannitol, about 10% by weight of microcrystalline cellulose (for example, PH112), about 3% by weight of sodium starch glycolate, about 1% by weight of stearic acid, about 0.4% by weight of butylated hydroxy toluene, about 0.5% by weight of disodium EDTA, and about 1% by weight of magnesium stearate.

In another embodiment, the pharmaceutical compositions provided herein comprise about 10% by weight of Form A of Compound 1, about 59.85% by weight of mannitol, about 25% by weight of microcrystalline cellulose, about 3% by weight of sodium starch glycolate, about 1% by weight of silicon dioxide, about 0.5% by weight of stearic acid, and about 0.65% by weight of magnesium stearate.

In another embodiment, the pharmaceutical compositions provided herein comprise about 10% by weight of Form A of Compound 1, about 59.45% by weight of mannitol, about 25% by weight of microcrystalline cellulose, about 3% by weight of sodium starch glycolate, about 1% by weight of silicon dioxide, about 0.5% by weight of stearic acid, about 0.4% BHT, and about 0.65% by weight of magnesium stearate.

In another embodiment, the pharmaceutical compositions provided herein comprise about 10% by weight of Form A of Compound 1, about 59.35% by weight of mannitol, about 25% by weight of microcrystalline cellulose, about 3% by weight of sodium starch glycolate, about 1% by weight of silicon dioxide, about 0.5% by weight of stearic acid, about 0.5% disodium EDTA, and about 0.65% by weight of magnesium stearate.

In another embodiment, the pharmaceutical compositions provided herein comprise about 10% by weight of Form A of Compound 1, about 58.95% by weight of mannitol, about 25% by weight of microcrystalline cellulose, about 3% by weight of sodium starch glycolate, about 1% by weight of silicon dioxide, about 0.5% by weight of stearic acid, about 0.5% disodium EDTA, about 0.4% BHT, and about 0.65% by weight of magnesium stearate.

In another embodiment, the pharmaceutical compositions provided herein comprise about 5% by weight of Form A of Compound 1, about 64.85% by weight of mannitol, about 25% by weight of microcrystalline cellulose, about 3% by weight of sodium starch glycolate, about 1% by weight of silicon dioxide, about 0.5% by weight of stearic acid, and about 0.65% by weight of magnesium stearate. In certain embodiments, the pharmaceutical composition is coated with Opadry Yellow. In certain embodiments, the pharmaceutical composition is coated with Opadry Pink.

In another embodiment, the pharmaceutical compositions provided herein comprise about 5% by weight of Form A of Compound 1, about 64.35% by weight of mannitol, about 25% by weight of microcrystalline cellulose, about 3% by weight of sodium starch glycolate, about 1% by weight of silicon dioxide, about 0.5% by weight of stearic acid, about 0.5% disodium EDTA, and about 0.65% by weight of magnesium stearate.

In another embodiment, the pharmaceutical compositions provided herein comprise about 0.7% by weight of Compound 1 and about 38.1% by weight of microcrystalline cellulose (for example, PH 102), about 57.2% by weight of mannitol, about 3% by weight of sodium carboxymethylcellulose, and about 1% by weight of magnesium stearate.

In another embodiment, the pharmaceutical compositions provided herein comprise about 0.7% by weight of Compound 1 and about 75.3% by weight of microcrystalline cellulose (for example, PH 102), about 20% by weight of pregelatinized starch, about 3% by weight of sodium carboxymethylcellulose, about 1% by weight of and magnesium stearate.

In another embodiment, the pharmaceutical compositions provided herein comprise about 0.7% by weight of Compound 1 and about 38.1% by weight of microcrystalline cellulose (for example, PH 102), about 57.2% by weight of lactose monohydrate, about 3% by weight of sodium carboxymethylcellulose, and about 1% by weight of magnesium stearate.

In another embodiment, the pharmaceutical compositions provided herein comprise about 25% by weight of Compound 1 and about 28.4% by weight of microcrystalline cellulose (for example, PH 102), about 42.6% by weight of mannitol, about 3% by weight of sodium carboxymethylcellulose, and about 1% by weight of magnesium stearate.

In another embodiment, the pharmaceutical compositions provided herein comprise about 25% by weight of Compound 1 and about 51% by weight of microcrystalline cellulose (for example, PH 102), about 20% by weight of pregelatinized starch, about 3% by weight of sodium carboxymethylcellulose, about 1% by weight of magnesium stearate.

In another embodiment, the pharmaceutical compositions provided herein comprise about 25% by weight of Compound 1 and about 28.4% by weight of microcrystalline cellulose (for example, PH 102), about 42.6% by weight of lactose monohydrate, about 3% by weight of sodium carboxymethylcellulose, and about 1% by weight of magnesium stearate.

In certain embodiments, provided herein are pharmaceutical compositions comprising an opaque coating. Without being limited by theory, it was found that a more opaque coating protected the drug product from degradation. In some embodiments, the pharmaceutical composition is formulated as a tablet. In some such embodiments, the tablet is film coated. In some embodiments, the tablet is film coated to a weight gain of 1-8%. In others, the film coating is about 4% by weight of the tablet.

In certain embodiments, provided herein are pharmaceutical compositions, wherein the amounts of the recited components can independently be varied by 1%, 2%, 3%, 4%, 5%, 6%, 7%, 8%, 9%, 10%, 15%, 20% or 25%.

The pharmaceutical compositions provided herein can be provided in a unit-dosage form or multiple-dosage form. A unit-dosage form, as used herein, refers to physically discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an individually packaged tablet or capsule. A unit-dosage form may be administered in fractions or multiples thereof. A multiple-dosage form is a plurality of identical unit-dosage forms packaged in a single container to be administered in segregated unit-dosage form.

In another embodiment, provided herein are unit dosage formulations that comprise between about 0.1 mg and about 2000 mg, about 1 mg and 200 mg, about 35 mg and about 1400 mg, about 125 mg and about 1000 mg, about 250 mg and about 1000 mg, or about 500 mg and about 1000 mg of Compound 1, or a pharmaceutically acceptable salt, isotopologue or solid form thereof.

In a particular embodiment, provided herein are unit dosage formulation comprising about 0.1 mg, about 0.25 mg, about 0.5 mg, about 1 mg, about 2.5 mg, about 5 mg, about 7.5 mg, about 8 mg, about 10 mg, about 15 mg, about 20 mg, about 25 mg, about 30 mg, about 35 mg, about 40 mg, about 45 mg, about 50 mg, about 60 mg, about 70 mg, about 75 mg, about 100 mg, about 125 mg, about 140 mg, about 150 mg, about 175 mg, about 200 mg, about 250 mg, about 280 mg, about 300 mg, about 350 mg, about 400 mg, about 500 mg, about 560 mg, about 600 mg, about 700 mg, about 750 mg, about 800 mg, about 1000 mg or about 1400 mg of a DHPP. In a particular embodiment, provided herein are unit dosage formulations that comprise about 2.5 mg, about 5 mg, about 7.5 mg, about 8 mg, about 10 mg, about 15 mg, about 20 mg, about 25 mg, about 30 mg, about 40 mg, about 45 mg, about 50 mg, about 60 mg or about 100 mg of Compound 1, or a pharmaceutically acceptable salt, tautomer, isotopologue or stereoisomer thereof. In a particular embodiment, provided herein are unit dosage formulations that comprise about 5 mg, about 7.5 mg, about 8 mg, and about 10 mg.

In some embodiments, a unit dosage form comprising Compound 1, or a pharmaceutically acceptable salt, isotopologue or solid form thereof can be administered once daily (QD), twice daily (BID), three times daily, four times daily or more often.

In certain embodiments, provided herein are methods for preparing a composition provided herein, comprising: (i) weighing out the desired amount of Compound 1, or a pharmaceutically acceptable salt, isotopologue or solid form (such as Form A, Form B, Form C, Form D or Form E) thereof and the desired amount of excipients (such as lactose monohydrate, croscarmellose sodium and/or microcrystalline cellulose); (ii) mixing or blending Compound 1, or a pharmaceutically acceptable salt, isotopologue or solid form thereof and the excipients; (iii) passing the mixture of Compound 1, or a pharmaceutically acceptable salt, isotopologue or solid form thereof and excipients through a screen (such as a 25 mesh screen); (iv) mixing or blending Compound 1, or a pharmaceutically acceptable salt, isotopologue or solid form thereof and the excipients after passage through the screen; (v) weighing out the desired amount of lubricating agents (such as stearic acid and magnesium stearate); (vi) passing the lubricating agents through a screen (such as a 35 mesh screen); (vii) mixing or blending Compound 1, or a pharmaceutically acceptable salt, isotopologue or solid form thereof, the excipients and the lubricating agents; (viii) compressing the mixture of Compound 1, or a pharmaceutically acceptable salt, isotopologue or solid form thereof, the excipients and the lubricating agents (such as into a tablet form); and optionally (ix) coating the compressed mixture of Compound 1, or a pharmaceutically acceptable salt, isotopologue or solid form thereof, the excipients and the lubricating agents with a coating agent (such as Opadry pink, yellow or beige). In certain embodiments, the methods for preparing a composition provided herein are carried out in the dark, under yellow light or in the absence of UV light.

In certain embodiments, the pharmaceutical compositions provided herein comprise Form A of Compound A, including substantially pure Form A.

6. EXAMPLES

The following Examples are presented by way of illustration, not limitation. The following abbreviations are used in descriptions and examples:

AmPhos: p-dimethylamino phenylditbutylphosphine
Boc: tert-Butoxycarbonyl
dba: dibenzylideneacetone
DIPEA: N,N-diisopropylethylamine
DMSO: Dimethylsulfoxide
EDTA: Ethylenediaminetetraacetate or ethylenediaminetetraacetic acid
ESI: Electrospray ionization
HPLC: High performance liquid chromatography
mp: Melting point
MS: Mass spectrometry
Ms: mesylate or methanesulfonyl
NBS: N-Bromosuccinimide
NMR: Nuclear magnetic resonance
NMP: N-methylpyrrolidinone
Tf: triflate or trifluoromethanesulfonyl
TFA: Trifluoroacetic acid
TLC: Thin layer chromatography
MTBE: methyl tert-butyl ether

6.1 Synthetic Examples

The following non-limiting synthetic examples show methods for the preparation of compounds provided herein. Chem-4D Draw (ChemInnovation Software, Inc., San Diego, Calif.) or ChemDraw Ultra (Cambridgesoft, Cambridge, Mass.) was used to generate names for chemical structures.

Example 1: 1-Ethyl-7-(2-methyl-6-(4H-1,2,4-triazol-3-yl)pyridin-3-yl)-3,4-dihydropyrazino[2,3-b]pyrazin-2(1H)-one

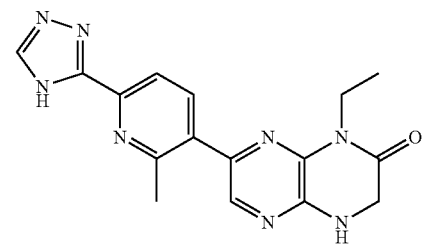 [SMILES: CCN1C(=O)CNc2ncc(-c3ccc(-c4nnc[nH]4)nc3C)nc21]

A. Ethyl 2-(3,5-dibromopyrazin-2-ylamino)acetate

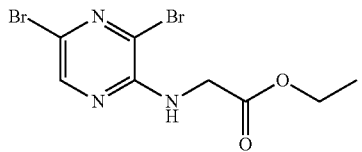

Amino-3,5-dibromopyrazine (1 equiv) in dimethylformamide was cooled to 0° C. and treated with cesium carbonate (1.3 equiv) and ethyl chloroacetate (1.2 equiv). The solution was warmed to 25° C. and further heated to 65° C. The reaction mixture was cooled to 25° C., filtered, and the solid was washed with dimethylformamide. The filtrate was added to ice-water and the slurry was agitated. The resulting solid was isolated, washed with water, and dried. The crude product was dissolved in methyl t-butyl ether with heating, cooled to rt, and concentrated to dryness. The solid was dissolved in ethyl acetate and concentrated to a thick slurry. The product was triturated with 2% ethyl acetate in heptane, filtered, washed with heptane, and dried to afford the title compound as a solid. MS (ESI) m/z 337.8 [M−1]$^+$, 339.8 [M+1]$^+$, 341.8 [M+3]$^+$.

B. 2-((3,5-dibromopyrazin-2-yl)amino)acetic acid and ethylamine

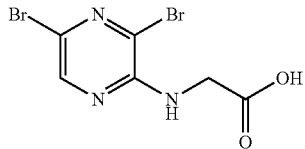

Ethyl 2-(3,5-dibromopyrazin-2-ylamino)acetate (1 equiv), tetrahydrofuran and sodium hydroxide in water (1.1 equiv) were combined and stirred at room temperature overnight. The reaction mixture was treated with dilute phosphoric acid (1.9 equiv) and heptane. The organic layer was concentrated to about 75% of its original volume and further distilled with addition of heptane until the reaction mixture was 80° C. The solution was treated with seed and distillation with addition of heptane was continued until reaching 85° C. The slurry was cooled and filtered, and the solids washed with heptane and dried to obtain 2-((3,5-dibromopyrazin-2-yl)amino)acetic acid as a solid. MS (ESI) m/z 309.9 [M+1].

C. 7-Bromo-1-ethyl-3,4-dihydropyrazino[2,3-b]pyrazin-2(1H)-one

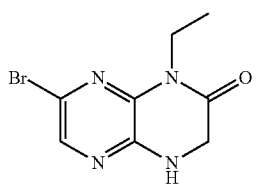

The 2-((3,5-dibromopyrazin-2-yl)amino)acetic acid and ethylamine (4 equiv, 70 wt % solution) were combined in water and the mixture was stirred at 90° C. The reaction mixture was cooled to 80° C. and treated with phosphoric acid (4 equiv), and the mixture was cooled to room temperature and the solids were collected by filtration. The product was dried to obtain 7-bromo-1-ethyl-3,4-dihydropyrazino[2,3-b]pyrazin-2(1H)-one as a solid. MS (ESI) m/z 256.9

D. 1-Ethyl-7-(4,4,5,5-tetramethyl-1,3,2-dioxaborolan-2-yl)-3,4-dihydropyrazino[2,3-b]pyrazin-2(1H)-one

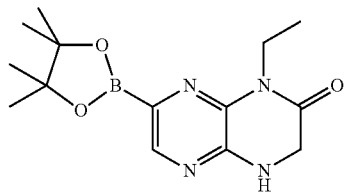 [SMILES: CCN1C(=O)CNc2ncc(B3OC(C)(C)C(C)(C)O3)nc21]

A mixture of 7-bromo-1-ethyl-3,4-dihydropyrazino[2,3-b]pyrazin-2(1H)-one (1 equiv), bis(pinacolato)diboron (1.5 equiv), and potassium acetate (3.0 equiv) were combined in tetrahydrofuran. The reaction was heated to reflux, cooled, treated with PdCl$_2$Amphos$_2$ (0.001 equiv), and heated to reflux. The reaction mixture was cooled to room temperature, filtered, and the collected solids were washed with tetrahydrofuran. The filtrate was treated with activated carbon at 50° C., filtered, treated with activated carbon at 50° C. a second time, and filtered. The filtrate was concentrated to 20% of the original volume, cooled, and treated with heptane. The resulting solids were collected by filtration, washed, and dried to obtain 1-ethyl-7-(4,4,5,5-tetramethyl-1,3,2-dioxaborolan-2-yl)-3,4-dihydropyrazino[2,3-b]pyrazin-2(1H)-one as a white solid.

E. 1-Ethyl-7-(2-methyl-6-(1-(tetrahydro-2H-pyran-2-yl)-1H-1,2,4-triazol-3-yl)pyridin-3-yl)-3,4-dihydropyrazino[2,3-b]pyrazin-2(1H)-one

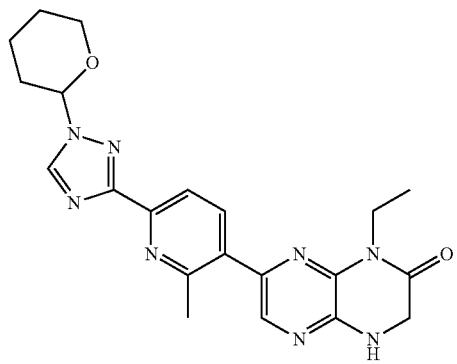 [SMILES: CCN1C(=O)CNc2ncc(-c3ccc(-c4ncn(C5CCCCO5)n4)nc3C)nc21]

A portion of 1-ethyl-7-(4,4,5,5-tetramethyl-1,3,2-dioxaborolan-2-yl)-3,4-dihydropyrazino[2,3-b]pyrazin-2(1H)-one (1 equiv), 3-bromo-2-methyl-6-(1-(tetrahydro-2H-pyran-2-yl)-1H-1,2,4-triazol-3-yl)pyridine (0.95 equiv), potassium hydrogen carbonate (2.3 equiv), and PdCl$_2$Amphos$_2$ (0.001 equiv) were treated with a mixture of tetrahydrofuran and water, and the reaction mixture was heated to 55° C. The reaction mixture was cooled and the organic layer was treated with activated carbon at ambient temperature and filtered. The filtrate was distilled to 70% of its original volume, cooled, treated with water, seeded, and treated with additional water. The solids were filtered and washed with tetrahydrofuran/water and dried to obtain 1-ethyl-7-(2-methyl-6-(1-(tetrahydro-2H-pyran-2-yl)-1H-1,2,4-triazol-3-yl)pyridin-3-yl)-3,4-dihydropyrazino[2,3-b]pyrazin-2(1H)-one as a solid.

F. 1-Ethyl-7-(2-methyl-6-(4H-1,2,4-triazol-3-yl)pyridin-3-yl)-3,4-dihydropyrazino[2,3-b]pyrazin-2(1H)-one

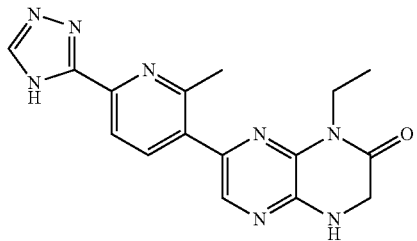 [SMILES: CCN1C(=O)CNc2ncc(-c3ccc(-c4nnc[nH]4)nc3C)nc21]

A portion of 1-ethyl-7-(2-methyl-6-(1-(tetrahydro-2H-pyran-2-yl)-1H-1,2,4-triazol-3-yl)pyridin-3-yl)-3,4-dihydropyrazino[2,3-b]pyrazin-2(1H)-one (1 equiv), butylated hydroxytoluene (0.002 equiv), reagent alcohol (90% ethanol, 5% methanol, 5% isopropanol), and dilute aqueous hydrogen chloride (1 equiv) were combined and heated to 60° C. The reaction mixture was cooled to 45° C., neutralized with dilute aqueous ammonium hydroxide, and filtered. The collected solids were washed with a reagent alcohol/water mixture and dried to obtain crude 1-ethyl-7-(2-methyl-6-(4H-1,2,4-triazol-3-yl)pyridin-3-yl)-3,4-dihydropyrazino[2,3-b]pyrazin-2(1H)-one as a solid. Crude 1-ethyl-7-(2-methyl-6-(4H-1,2,4-triazol-3-yl)pyridin-3-yl)-3,4-dihydropyrazino[2,3-b]pyrazin-2(1H)-one (1 equiv), butylated hydroxytoluene (0.002 equiv), reagent alcohol (90% ethanol, 5% methanol, 5% isopropanol) and water (4:1), and dilute aqueous hydrogen chloride (2 equiv) were combined and heated to 45° C., treated with a metal scavenger (SiliaBond® Thiol) (10 wt %), heated to 60° C., cooled to 45° C. and filtered. The filtrate was treated with activated carbon (10 wt %), heated to 45° C., and filtered. The filtrate was heated to 45° C., treated with dilute aqueous ammonium hydroxide, seeded with crystal Form A, treated with additional dilute aqueous ammonium hydroxide, cooled, and filtered. The collected solids were washed with a reagent alcohol/water mixture and dried to obtain 1-ethyl-7-(2-methyl-6-(4H-1,2,4-triazol-3-yl)pyridin-3-yl)-3,4-dihydropyrazino[2,3-b]pyrazin-2(1H)-one as Form A.

G. 1-Ethyl-7-(2-methyl-6-(4H-1,2,4-triazol-3-yl)pyridin-3-yl)-3,4-dihydropyrazino[2,3-b]pyrazin-2(1H)-one (Alternative approach)

Crude 1-ethyl-7-(2-methyl-6-(4H-1,2,4-triazol-3-yl)pyridin-3-yl)-3,4-dihydropyrazino[2,3-b]pyrazin-2(1H)-one (1 equiv) and butylated hydroxytoluene (0.002 equiv) in a mixture of 1-propanol and water (1.1) were treated with dilute aqueous hydrogen chloride (2.5 equiv), treated with a metal scavenger (SiliaBond® Thiol) (10 wt %), and filtered. The filtrate was treated with activated carbon (10 wt %) and filtered. The solution was charged to a dilute aqueous ammonium hydroxide solution at 60° C., and the reaction mixture was cooled, filtered, and washed with 1-propanol/water to obtain 1-ethyl-7-(2-methyl-6-(4H-1,2,4-triazol-3-yl)pyridin-3-yl)-3,4-dihydropyrazino[2,3-b]pyrazin-2(1H)-one as Form A.

H. 1-Ethyl-7-(2-methyl-6-(4H-1,2,4-triazol-3-yl)pyridin-3-yl)-3,4-dihydropyrazino[2,3-b]pyrazin-2(1H)-one (Alternative approach)

Crude 1-ethyl-7-(2-methyl-6-(4H-1,2,4-triazol-3-yl)pyridin-3-yl)-3,4-dihydropyrazino[2,3-b]pyrazin-2(1H)-one (1 equiv) and butylated hydroxytoluene (0.002 equiv) in a mixture of 1-propanol and water (1:1) were treated with dilute aqueous hydrogen chloride (2 equiv). The solution was treated with a metal scavenger (SiliaBond® Thiol) (10 wt %), and filtered. The filtrate was treated with activated carbon (10 wt %) and filtered. The filtrate was treated with a dilute aqueous ammonium hydroxide solution at 45° C., seeded, treated with additional dilute aqueous NH4OH solution, cooled, filtered, and washed with 1-propanol/water to obtain 1-ethyl-7-(2-methyl-6-(4H-1,2,4-triazol-3-yl)pyridin-3-yl)-3,4-dihydropyrazino[2,3-b]pyrazin-2(1H)-one as Form A.

MS (ESI) m/z 337.6 [M+1]$^+$ $^{13}$C NMR (75 MHz, DMSO-d$_6$) d=164.1, 160.9, 155.8, 155.4, 153.4, 152.0, 144.3, 142.9, 137.6, 137.1, 136.5, 135.2, 134.7, 133.2, 132.0, 119.1, 118.8, 45.7, 34.4, 23.9, 12. $^1$H NMR (300 MHz, DMSO-d$_6$) d=14.62 (br. s., 4H), 14.26 (br. s., 2H), 8.68 (br. s., 2H), 8.09 (br. s., 4H), 8.04-7.82 (m, 18H), 7.72 (br. s., 6H), 4.28-4.17 (m, 12H), 4.05 (d, J=7.2 Hz, 9H), 4.13-3.93 (m, 3H), 3.35 (br. s., 2H), 2.73 (br. s., 18H), 1.18 (t, J=7.0 Hz, 19H), 1.06 (s, 1H)

Example 2: Building Block Synthesis

The following building blocks were prepared and used in the preparations as described herein, or variations known in the art thereof.

3-Bromo-2-methyl-6-(1-(tetrahydro-2H-pyran-2-yl)-1H-1,2,4-triazol-3-yl)pyridine

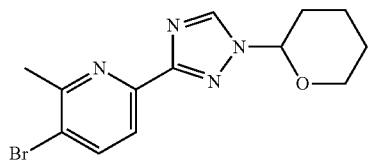 [SMILES: Cc1nc(-c2ncn(C3CCCCO3)n2)ccc1Br]

A. 3-Bromo-6-iodo-2-methylpyridine

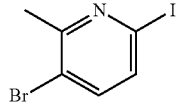

Sodium iodide (2 equiv) and 3,6-dibromo-2-methylpyridine (1 equiv) were combined in propionitrile and the resulting slurry was treated with iodotrimethylsilane (0.2 equiv) and heated to 95° C., with stirring, under nitrogen for 24 h. The slurry was cooled to room temperature, diluted with a 1:1 mixture of ethyl acetate and water and the aqueous and organic phases were separated. The organic layer was washed with saturated aqueous sodium bicarbonate solution, sodium thiosulfate (5% aqueous solution), and saturated aqueous sodium chloride solution. The organic phase was dried, filtered, and concentrated under reduced pressure to afford the desired product, as an oil, which crystallized to a solid. MS (ESI) m/z 297.8 [M]$^+$, 299.8 [M+2]$^+$.

B. 5-Bromo-6-methylpicolinonitrile

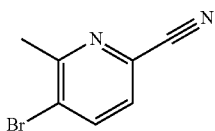

3-Bromo-6-iodo-2-methylpyridine (1 equiv) and acetonitrile were combined and copper cyanide (0.5 equiv), sodium cyanide (0.8 equiv) were added. The reaction slurry was heated to 80° C. for 24 h. The reaction solution was cooled to room temperature and diluted with ammonium hydroxide (0.5 M aqueous solution). The mixture was stirred 15-30 min, filtered through diatomaceous earth and the filter cake was washed with ethyl acetate. The filtrate and wash were combined and diluted with ethyl acetate. The aqueous and organic phases were separated and the organic layer was washed with ammonium hydroxide (0.5 M aqueous solution) and saturated aqueous sodium chloride, dried, filtered, and concentrated under reduced pressure to provide 5-bromo-6-methylpicolinonitrile as a. MS (ESI) m/z 196.9 [M]$^+$, 198.9 [M+2]$^+$.

C. 5-Bromo-6-methylpicolinimidohydrazide

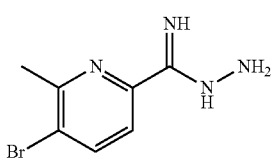

Hydrazine monohydrate (2 equiv) was added to a stirring 1.2 M suspension of 5-bromo-6-methylpicolinonitrile (1 equiv) in ethanol. The reaction mixture was heated to 50° C. for 24 h. The reaction was cooled to room temperature and filtered. The collected solid was washed with ethanol and t-butyl methyl ether. The solid was dried under vacuum to provide the title compound, as a solid. MS (ESI) m/z 228.9 [M]$^+$, 230.9 [M+2]$^+$.

D. 3-Bromo-2-methyl-6-(4H-1,2,4-triazol-3-yl)pyridine

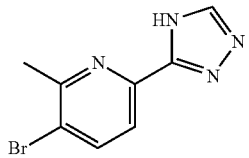

5-Bromo-6-methylpicolin-imido-hydrazide (1 equiv) and formic acid (15 equiv) were combined and heated to 100° C. for 6 h. The reaction was cooled to room temperature and diluted with methanol. The resulting slurry was partially concentrated under reduced pressure and the resulting mixture was diluted with methanol and partially concentrated under reduced pressure. The resulting solids were collected by filtration, washed with water and dried to provide the desired product, as a solid. MS (ESI) m/z 238.9 [M]$^+$, 240.9 [M+2]$^+$.

E. 3-Bromo-2-methyl-6-(1-(tetrahydro-2H-pyran-2-yl)-1H-1,2,4-triazol-3-yl)pyridine

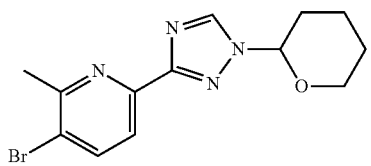 [SMILES: Cc1nc(-c2ncn(C3CCCCO3)n2)ccc1Br]

3-Bromo-2-methyl-6-(4H-1,2,4-triazol-3-yl)pyridine (1 equiv), 3,4-dihydro-2H-pyran (2 equiv) and methanesulfonic acid (0.1 equiv) were combined in tetrahydrofuran. The reaction was heated to 68° C. for 3.5 h, cooled to room temperature, and treated with triethylamine (0.4 equiv). The reaction mixture was concentrated under reduced pressure, treated with acetonitrile and concentrated under reduced pressure at 35° C. The residue was dissolved in acetonitrile (1 volume) and water (2.25 volumes), and the solids were collected by filtration, washed with a solution of 20% acetonitrile in water and dried. The crude product was triturated with hexanes, filtered, washed with hexanes and dried to provide the desired product, as a solid. MS (ESI) m/z 324.9 [M+2]$^+$.

6.2 Solid Forms 6.2.1 Polymorph Screen

A polymorph screen of Compound 1 was performed to investigate whether different solid forms could be generated under various conditions, such as different solvents, temperature and humidity changes. A total of five crystalline forms were found. Form A was found to be a stable anhydrous and non-hygroscopic crystalline form that melts at approximated 270° C. Forms B, C and E were found to be hydrates. Form D was found to be a DMSO solvate.

TABLE 1

Physical Characterization of Solid Forms of Compound 1

| Form | Representative crystallization solvent | XRPD/ morphology | DSC peaks (° C.) | TGA loss (wt %) | Water by KF (% w/w) | Moisture sorption (wt % at 90% RH | Comment |
|---|---|---|---|---|---|---|---|
| A | Starting material, various conditions | crystalline irregular | 269.6 | 0.01 | n/a | 0.4 | anhydrate |
| B | Methanol | crystalline needles | 98.4, 133.8, 143.5^, 158.8^, 267.8 | 9.48 | 11.2 | 20.7 | hydrate |
| C | MeOH/water EtOH/water | crystalline needles | 95.6, 122.7, 135.9^, 270.3 | 9.82 | 12.8 | 12.2 | di-hydrate |
| D | DMSO/MTBE DMSO/EtOAc | crystalline flake | 141.4, 269.0 | 18.6 | n/a | n/a | solvate |
| E | MeOH/DCM slurry | crystalline | 65.4, 180.4^, 268.0 | 3.14, 2.07 | 4.8 | 5.9 | hydrate |

^Exothermic peak in DSC trace;
n/a: not analyzed.

Form A

The XRPD pattern, crystal habit, TGA and DSC thermograms of Form A of Compound 1 are shown in FIGS. 2-4. Form A was found to lose up to 0.01% volatiles during TGA analysis upon 100° C. and exhibited a single melting peak at 269.6° C. The moisture sorption/desorption behavior of Form A was determined by DVS and the results are summarized in FIG. 5. Form A exhibited a 0.46% mass change relative to the dry mass when the relative humidity was increased from 0 to 95%. This indicated that the material is not hygroscopic. After undergoing the full adsorption/desorption cycle, the XRPD diffractogram of the sample showed that the material was unchanged from the initial Form A. Based on these characterization studies and those described below, Form A was found to be a stable anhydrous and non-hygroscopic crystalline material.

TABLE 2

X-Ray Diffraction Peaks for Form A of Compound 1

| Two-theta angle (°) (numbers in parenthesis are unrounded) | d Space (Å) | Relative Intensity (%) |
|---|---|---|
| 8.0 (7.96) | 11.1039 | 7.4 |
| 9.8 (9.81) | 9.0136 | 100.0 |
| 12.0 (11.99) | 7.3830 | 33.8 |
| 15.9 (15.93) | 5.5636 | 15.4 |
| 17.4 (17.37) | 5.1060 | 8.7 |
| 17.9 (17.95) | 4.9415 | 27.7 |
| 18.3 (18.35) | 4.8356 | 3.8 |
| 19.5 (19.51) | 4.5506 | 3.9 |
| 21.6 (21.61) | 4.1131 | 3.9 |
| 21.9 (21.91) | 4.0565 | 8.3 |
| 22.3 (22.29) | 3.9877 | 6.0 |
| 24.0 (23.97) | 3.7132 | 1.5 |
| 25.2 (25.19) | 3.5357 | 21.4 |
| 26.4 (26.39) | 3.3748 | 4.5 |
| 26.5 (26.48) | 3.3657 | 5.6 |
| 27.1 (27.08) | 3.2932 | 11.5 |
| 28.0 (27.96) | 3.1917 | 5.0 |
| 29.4 (29.45) | 3.0335 | 2.9 |
| 30.1 (30.09) | 2.9701 | 2.7 |
| 31.3 (31.29) | 2.8583 | 1.5 |
| 32.1 (32.14) | 2.7852 | 1.6 |
| 36.4 (36.44) | 2.4657 | 3.7 |
| 38.6 (38.65) | 2.3297 | 2.0 |
| 39.4 (39.38) | 2.2881 | 1.5 |

Form B

Form B had a crystalline XRPD pattern as shown in FIG. 7. TGA and DSC thermograms of Form B are shown in FIGS. 8 and 9, respectively. Form B was found to lose up to 9.48% volatiles during TGA analysis upon 150° C. and exhibited multiple endo- and exothermic events before final melting at 267.8° C., indicating a solvate or hydrate. The $^1$H NMR spectrum of the Form B sample did not show signals of organic solvent, suggesting that Form B was most likely a hydrate (FIG. 10). The Form B sample was further analyzed by KF and showed 11.2 wt % of water, confirming a hydrate.

TABLE 3

X-Ray Diffraction Peaks for Form B of Compound 1

| Two-theta angle (°) (numbers in parenthesis are unrounded) | d Space (Å) | Relative Intensity (%) |
|---|---|---|
| 4.9 (4.92) | 17.9597 | 36.3 |
| 7.5 (7.52) | 11.7609 | 80.1 |
| 8.6 (8.57) | 10.3161 | 39.4 |
| 10.4 (10.42) | 8.4877 | 100.0 |
| 10.9 (10.92) | 8.0986 | 17.0 |
| 11.7 (11.71) | 7.5559 | 64.5 |
| 12.1 (12.11) | 7.3062 | 23.1 |
| 12.7 (12.74) | 6.9469 | 27.4 |
| 14.4 (14.43) | 6.1398 | 9.1 |
| 15.0 (15.02) | 5.8970 | 6.6 |
| 16.2 (16.25) | 5.4557 | 13.2 |
| 17.5 (17.55) | 5.0541 | 9.7 |
| 17.9 (17.94) | 4.9456 | 33.5 |
| 18.5 (18.54) | 4.7852 | 8.0 |
| 19.9 (19.92) | 4.4563 | 6.1 |
| 20.4 (20.39) | 4.3547 | 6.8 |
| 21.9 (21.93) | 4.0527 | 12.0 |
| 22.4 (22.42) | 3.9653 | 15.0 |
| 23.6 (23.59) | 3.7709 | 12.4 |
| 24.5 (24.53) | 3.6291 | 18.6 |
| 25.5 (25.53) | 3.4898 | 24.5 |
| 26.4 (26.41) | 3.3752 | 9.9 |
| 27.3 (27.28) | 3.2694 | 16.0 |
| 29.0 (29.03) | 3.0762 | 5.1 |
| 29.8 (29.79) | 2.9994 | 6.8 |
| 30.5 (30.47) | 2.9337 | 6.3 |

Form C

Form C was obtained from recrystallization in MeOH/water or EtOH/water. Form C had a crystalline XRPD pattern as shown in FIG. 12. TGA and DSC thermograms of Form C are shown in FIGS. 13 and 14, respectively. Form C was found to lose up to 9.82% volatiles during TGA analysis upon 150° C. and exhibited a multiple endo- and exothermic events before melting around 270.3° C., indicating a solvate or hydrate. The $^1$H NMR spectrum of the Form C sample crystallized from EtOH/water did not shown signals of organic solvent, suggesting that Form C was most likely a hydrate. See FIG. 15.

TABLE 4

X-Ray Diffraction Peaks for Form C of Compound 1

| Two-theta angle (°) (numbers in parenthesis are unrounded) | d Space (Å) | Relative Intensity (%) |
|---|---|---|
| 5.9 (5.86) | 15.0746 | 5.2 |
| 6.1 (6.07) | 14.5697 | 3.9 |
| 7.4 (7.42) | 11.9142 | 8.8 |
| 9.3 (9.35) | 9.4565 | 56.0 |
| 11.7 (11.75) | 7.5317 | 100.0 |
| 12.2 (12.16) | 7.2798 | 5.6 |
| 12.3 (12.30) | 7.1935 | 3.6 |
| 14.4 (14.39) | 6.1570 | 3.1 |
| 14.7 (14.67) | 6.0405 | 1.7 |
| 17.3 (17.34) | 5.1129 | 6.0 |
| 17.9 (17.92) | 4.9504 | 3.2 |
| 18.3 (18.27) | 4.8550 | 1.0 |
| 18.7 (18.75) | 4.7329 | 2.4 |
| 19.9 (19.94) | 4.4535 | 10.4 |
| 23.7 (23.67) | 3.7597 | 8.5 |
| 24.0 (24.00) | 3.7080 | 5.5 |
| 24.3 (24.35) | 3.6552 | 1.9 |
| 25.0 (25.03) | 3.5576 | 1.7 |
| 25.7 (25.73) | 3.4627 | 1.4 |
| 26.2 (26.22) | 3.3986 | 3.1 |
| 26.5 (26.52) | 3.3611 | 2.5 |
| 27.1 (27.15) | 3.2851 | 1.0 |
| 28.3 (28.28) | 3.1537 | 4.3 |
| 28.4 (28.36) | 3.1518 | 3.5 |
| 28.9 (28.87) | 3.0905 | 2.6 |
| 29.6 (29.64) | 3.0111 | 1.4 |
| 29.9 (29.95) | 2.9814 | 2.6 |
| 30.3 (30.34) | 2.9436 | 1.6 |
| 31.1 (31.15) | 2.8691 | 2.3 |
| 31.6 (31.56) | 2.8322 | 2.0 |
| 34.8 (34.85) | 2.5723 | 3.6 |
| 35.1 (35.08) | 2.5560 | 3.3 |

Form D

Form D was obtained from solvent/anti-solvent crystallization from DMSO/MTBE or DMSO/EtOAc. Form D had a crystalline XRPD pattern as shown in FIG. 17. TGA and DSC thermograms of Form D are shown in FIGS. 18 and 19, respectively. Form D was found to lose up to 18.6% volatiles during TGA analysis upon 150° C. and exhibited a desolvation process at around 140° C., indicating a solvate or hydrate. The $^1$H NMR spectrum of the Form D sample showed about one molar equivalent (i.e., 18.9 wt %) of DMSO (FIG. 20), consistent with the TGA weight loss observed. These results suggested that Form D was a DMSO solvate.

TABLE 5

X-Ray Diffraction Peaks for Form D of Compound 1

| Two-theta angle (°) (numbers in parenthesis are unrounded) | d Space (Å) | Relative Intensity (%) |
|---|---|---|
| 6.1 (6.07) | 14.5687 | 7.6 |
| 6.5 (6.55) | 13.5026 | 37.3 |

TABLE 5-continued

X-Ray Diffraction Peaks for Form D of Compound 1

| Two-theta angle (°) (numbers in parenthesis are unrounded) | d Space (Å) | Relative Intensity (%) |
|---|---|---|
| 8.3 (8.29) | 10.6607 | 22.3 |
| 10.2 (10.21) | 8.6616 | 19.9 |
| 10.7 (10.72) | 8.2534 | 31.7 |
| 11.0 (11.04) | 8.0126 | 78.9 |
| 13.0 (13.05) | 6.7853 | 25.0 |
| 14.0 (14.02) | 6.3152 | 37.3 |
| 14.1 (14.14) | 6.2654 | 35.7 |
| 16.6 (16.57) | 5.3500 | 28.7 |
| 17.1 (17.10) | 5.1855 | 10.2 |
| 18.2 (18.18) | 4.8794 | 41.1 |
| 19.2 (19.24) | 4.6121 | 7.1 |
| 19.6 (19.58) | 4.5347 | 43.3 |
| 20.2 (20.24) | 4.3881 | 100.0 |
| 20.7 (20.71) | 4.2894 | 25.8 |
| 21.9 (21.94) | 4.0513 | 78.1 |
| 22.7 (22.66) | 3.9243 | 31.7 |
| 23.4 (23.44) | 3.7948 | 45.8 |
| 23.8 (23.81) | 3.7369 | 25.6 |
| 24.3 (24.34) | 3.6570 | 30.9 |
| 24.8 (24.85) | 3.5796 | 22.8 |
| 24.9 (24.91) | 3.5742 | 22.9 |
| 25.4 (25.44) | 3.5007 | 27.6 |
| 26.1 (26.09) | 3.4159 | 30.1 |
| 26.3 (26.30) | 3.3885 | 22.5 |
| 26.9 (26.91) | 3.3133 | 18.5 |
| 27.2 (27.22) | 3.2764 | 11.1 |
| 27.9 (27.94) | 3.1934 | 4.0 |
| 28.6 (28.65) | 3.1161 | 9.6 |
| 29.4 (29.39) | 3.0386 | 3.7 |
| 29.7 (29.69) | 3.0090 | 3.0 |
| 30.5 (30.48) | 2.9331 | 13.5 |
| 31.3 (31.31) | 2.8567 | 8.8 |
| 31.7 (31.66) | 2.8258 | 5.9 |
| 32.4 (32.43) | 2.7612 | 3.3 |
| 32.8 (32.84) | 2.7271 | 10.2 |
| 33.4 (33.40) | 2.6826 | 31.0 |
| 33.8 (33.85) | 2.6483 | 2.5 |
| 34.2 (34.19) | 2.6227 | 2.1 |
| 35.0 (34.98) | 2.5653 | 9.3 |
| 35.7 (35.66) | 2.5181 | 3.5 |
| 36.4 (36.43) | 2.4666 | 8.6 |
| 37.3 (37.31) | 2.4104 | 3.6 |
| 39.0 (39.03) | 2.3080 | 7.6 |

Form E

Form E was obtained from slurry of Form A in MeOH/DCM (1:1). Form E had a crystalline XRPD pattern as shown in FIG. 21. TGA and DSC thermograms of Form D are shown in FIGS. 22 and 23, respectively. Form E showed two-step weight losses by TGA: 3.14 wt % between 30-90° C. and 2.10 wt % between 90 to 210° C. The first weight loss corresponded to a broad DSC endotherm at around 60° C. The second weight loss seems to coincide with the DSC exotherm around 180° C. The $^1$H NMR spectrum of the Form E was consistent with COMPOUND 1 structure and did not show significant amount of organic solvent. The KF analysis of Form E sample showed 4.8 wt % of water. These results suggested that Form E is most likely a hydrate not a solvate. The water content and total TGA weight loss coincided with a mono-hydrate of Compound 1 which has a theoretical water content of 5.1 wt %.

TABLE 6

X-Ray Diffraction Peaks for Form E of Compound 1

| Two-theta angle (°) (numbers in parenthesis are unrounded) | d Space (Å) | Relative Intensity (%) |
|---|---|---|
| 3.5 (3.46) | 25.5444 | 7.1 |
| 7.0 (7.01) | 12.6185 | 17.7 |
| 9.3 (9.28) | 9.5264 | 100.0 |
| 10.5 (10.53) | 8.3986 | 20.0 |
| 12.1 (12.15) | 7.2824 | 6.6 |
| 12.7 (12.66) | 6.9922 | 11.1 |
| 15.3 (15.34) | 5.7775 | 23.8 |
| 16.1 (16.14) | 5.4911 | 5.0 |
| 18.6 (18.65) | 4.7582 | 29.5 |
| 19.6 (19.63) | 4.5229 | 7.7 |
| 21.5 (21.47) | 4.1383 | 11.0 |
| 22.1 (22.06) | 4.0301 | 6.0 |
| 23.2 (23.16) | 3.8403 | 13.1 |
| 24.7 (24.74) | 3.5991 | 2.8 |
| 25.5 (25.49) | 3.4941 | 3.4 |
| 26.5 (26.46) | 3.3683 | 1.6 |
| 28.1 (28.15) | 3.1703 | 3.8 |

The solvents used in the polymorph screen were either HPLC or reagent grade, including acetone, acetonitrile (ACN), n-butanol (n-BuOH), absolute ethanol (EtOH), ethanol/water (1:1), methanol (MeOH), 2-propanol (IPA), ethyl acetate (EtOAc), methylene chloride (DCM), methyl ethyl ketone (MEK), methyl t-butyl ether (MTBE), heptane, toluene, tetrahydrofuran (THF), dimethyl sulfoxide (DMSO), N-methylpyrrolidone (NMP), N,N-dimethylformamide (DMF) and water.

All of the solid samples generated in the polymorph screen were analyzed by XRPD. XRPD analysis was conducted on a Thermo ARL X'TRA X-ray powder diffractometer using Cu Kα radiation at 1.54 Å. The instrument was equipped with a fine focus X-ray tube. The voltage and amperage of the X-ray generator were set at 45 kV and 40 mA, respectively. The divergence slits were set at 4 mm and 2 mm and the measuring slits were set at 0.5 mm and 0.2 mm. Diffracted radiation was measured using a Peltier-cooled Si (Li) solid-state detector. A theta-two theta continuous scan at 2.40°/min (0.5 sec/0.02° step) from 1.5° to 40° 2θ was used. A sintered alumina standard was used to check the peak positions.

DSC analyses were performed on a TA instrument Q2000 Differential Scanning calorimeter. Indium was used as the calibration standard. Approximately 2-5 mg of sample was placed into a DSC pan. The sample was heated under nitrogen at a rate of 10° C./min, up to a final temperature of 300° C. Melting points were reported as the extrapolated onset temperatures.

TGA analyses were performed on a TA instrument Q5000 Thermogravimetric Analyzer. Calcium oxalate was used for a performance check. Approximately 5-20 mg of accurately weighed sample was placed on a pan and loaded into the TGA furnace. The sample was heated under nitrogen at a rate of 10° C./min, up to a final temperature of 300° C.

Morphology analysis of the samples was carried out on an Olympus microscope. Small amounts of samples were dispersed in mineral oil on a glass slide with cover slips and viewed with 20× or 50× magnification.

Hygroscopicity was determined on a Surface Measurement Systems DVS. Typically a sample size of 2-10 mg was loaded into the DVS instrument sample pan and the sample was analyzed on a DVS automated sorption analyzer at room temperature. The relative humidity was increased from 0% to 90% RH at 10% RH step then 95% RH. The relative humidity was then decreased in a similar manner to accomplish a full adsorption/desorption cycle. For selected hydrated forms, the analysis started at 50% RH and increased to 90% RH at 10% RH step. The relative humidity was then decreased in a similar manner to 0% RH followed by increasing to 50% RH.

$^1$H NMR spectra were obtained on a Bruker 300 MHz NMR spectrometer. Form B, Form C, and Form E samples were dissolved in DMSO-$d_6$. The Form D sample was dissolved in DMF-$d_6$.

6.2.2 Solubility and Stability Experiments

Solubility of Form A in selected aqueous and organic solvents was determined by mixing solid with solvents at room temperature. The solubility samples were filtered after 24 hours of agitation and quantified by an HPLC method, except for DMSO for which the solubility was estimated from visual observation of complete dissolution upon solvent addition. Solubility of Form B and Form C in water was also determined by the same HPLC method. The results are shown in Table 7 below.

TABLE 7

Solubility of Compound 1 Form A in Select Solvents

| Solvent | Solubility (mg/mL) (room temperature) |
|---|---|
| Water | 0.08 |
| 0.9% NaCl | 0.03 |
| 0.1N HCl | 7.10 |
| Acetate buffer pH 4.0 | 0.06 |
| Phosphate buffer pH 6.8 | 0.05 |
| Acetonitrile | 0.14 |
| Acetone | 0.46 |
| Methanol | 1.13 |
| Ethanol | 0.50 |
| Isopropanol | 0.28 |
| Ethyl acetate | 0.32 |
| Tetrahydrofuran | 5.50 |
| Heptane | <0.005 |
| Dimethyl Sulfoxide | >50 |

Reference: NB# 5536-29

To evaluate thermodynamic stability of Form A, slurries of Form A were performed at room temperature for 2 weeks in various solvents, including ACN, MeOH, MTBE, water and EtOH/Water (1:1). See Table 8 and Table 9. Experiments were carried out by adding an excess of Form A to 2 mL of a test solvent. The resulting mixture was agitated for at least 24 hours at room temperature and 50° C. separately. Upon reaching equilibrium, the saturated supernatant solution was removed and allowed to evaporate slowly in an open vial under nitrogen at room temperature and 50° C., respectively. The solid resulting from the equilibration was filtered and air-dried before analysis.

TABLE 8

Equilibration Experiments of Form A at Room Temperature

| Solvent | XRPD Result 24 hours |
|---|---|
| Acetone | Form A |
| Acetonitrile | Form A |
| n-Butanol | Form A |
| Ethanol | Form A |
| Ethyl acetate | Form A |
| Heptane | Form A |

TABLE 8-continued

Equilibration Experiments of
Form A at Room Temperature

| Solvent | XRPD Result 24 hours |
|---|---|
| Methanol | Form A |
| Methylene chloride | Form A |
| Methyl ethyl ketone | Form A |
| Methyl t-butyl ether | Form A |
| 2-Propanol | Form A |
| Toluene | Form A |
| Tetrahydrofuran | Form A |
| Water | Form A |
| Ethanol/Water (1:1) | Form A |

TABLE 9

Slurry Experiments of Form A at 50° C.

| Solvent | XRPD Result 24 hours |
|---|---|
| Acetone | Form A |
| Acetonitrile | Form A |
| n-Butanol | Form A |
| Ethanol | Form A |
| Ethyl acetate | Form A |
| Heptane | Form A |
| Methanol | Form A |
| Methyl ethyl ketone | Form A |
| 2-Propanol | Form A |
| Toluene | Form A |
| Tetrahydrofuran | Form A |
| Water | Form A |
| Ethanol/Water (1:1) | Form A |

Evaporation experiments were performed by adding an excess of Compound 1 to 2 mL of a test solvent. The resulting mixture was agitated for at least 24 hours at room temperature and 50° C. separately. Upon reaching equilibrium, the saturated supernatant solution was removed and allowed to evaporate slowly in an open vial under nitrogen at room temperature and 50° C., respectively. The solid resulting from the equilibration was filtered and air-dried before analysis. The results are summarized in Table 10.

TABLE 10

Evaporation Experiments of Form A at 50° C.

| Solvent | XRPD Result |
|---|---|
| Methanol | Form A + B (semi-crystalline) |
| Tetrahydrofuran | Amorphous, degraded |

The solid obtained from MeOH provided a semi-crystalline XRPD pattern with Form A peaks and additional unique peaks that were later found to attribute to Form B. The amorphous solid obtained from THF had changed the color to dark brown and LC-MS result showed that the oxidation occurred during the evaporation experiment.

Fast cooling recrystallization experiments were performed using single or mixed solvents according to the following procedure. Selected solvents (MeOH, MeOH/$H_2O$, EtOH/$H_2O$, THF/$H_2O$ and DMF) were saturated with Compound 1 at approximately 50-70° C. Once the solid was completely dissolved, the solution was rapidly cooled by placing into a refrigerator. Solids were isolated after 24 hours.

The results are summarized in Table 11. Three solid forms were founded from these experiments. Form A was obtained from DMF; Form B was obtained from MeOH; and a unique form designated as Form C was obtained from MeOH/$H_2O$ (1:1) and EtOH/$H_2O$ (1:1).

TABLE 11

Fast Cooling Recrystallization

| Solvent | Method | XRPD Result |
|---|---|---|
| MeOH | Dissolved at reflux Cooled to 4° C. | Form B |
| MeOH/$H_2O$ (1:1) | Dissolved at reflux Cooled to 4° C. | Form C |
| Ethanol/$H_2O$ (1:1) | Dissolved at ~50° C. Cooled to 4° C. | Form C |
| THF/$H_2O$ (1:1) | Dissolved at 50° C. Cooled to 4° C. | Form A + C |
| DMF | Dissolved at ~50° C. Cooled to 4° C. | Form A |

Anti-solvent recrystallization experiments were performed as described below, using DMSO or DMF as primary solvent and MTBE, water, or EtOAc as anti-solvents. The selected solvents (DMSO and NMP) were saturated with Compound 1 at room temperature. Once the solid was completely dissolved, an anti-solvent (Ethyl acetate, MTBE, or water) was added into the solution. The mixture was stirred at room temperature overnight. If no precipitation occurred, the vial was further cooled by placing into a refrigerator. The solid resulting from the recrystallization was filtered and air-dried before analysis.

The results are summarized in Table 12. A unique form designated as Form D was generated from crystallization using DMSO/MTBE or DMSO/EtOAc. Other combinations of solvents each generated Form A.

TABLE 12

Recrystallization with Anti-solvents

| Solvent | Anti-solvent | Ratio (Solvent/Anti-solvent) | XRPD Result |
|---|---|---|---|
| DMSO | MTBE | 1:15 | Form D |
| DMSO | Water | 1:7.5 | Form A |
| DMSO | Ethyl acetate | 1:15 | Form D |
| NMP | MTBE | 1:15 | Form A |
| NMP | Water | 1:7.5 | Form A |
| NMP | Ethyl acetate | 1:15 | Form A |

The stability of Form A was demonstrated by exposing the sample to a 40° C./75% RH environment for 1 month. Solid form of the exposed material was not changed compared to the initial unexposed sample. See Table 13. Form A was also found to be stable upon application of 2000-psi pressure for about 1 minute (FIG. 6), with slight increase in amorphous content.

TABLE 13

Stability of Form A

| Starting Form | Test Conditions | XRPD Results |
|---|---|---|
| Form A | 40° C./75% RH, 4 weeks, open vial | Form A |
| Form A | 40° C./75% RH, 4 weeks, closed vial | Form A |

Competitive slurries between Form A and Form B or Form A and Form C were also performed in MeOH and EtOH/water (1:1). Solids isolated from these slurries were all consistent with Form A. See Table 14. These results suggested that Form A was the most stable form.

TABLE 14

Form Transfer Experiments

| Starting Form | Solvent | Seed Form | Time | XRPD Result |
|---|---|---|---|---|
| Form A | H₂O | None | 2 weeks | Form A |
| Form A | MeOH | None | 2 weeks | Form A |
| Form A | MTBE | None | 2 weeks | Form A |
| Form A | Ethanol/Water (1:1) | None | 2 weeks | Form A |
| Form A | Acetonitrile | None | 2 weeks | Form A |
| Form B | Acetonitrile | None | 3 days | Form A |
| Form C | Acetonitrile | None | 3 days | Form A |
| Form C | MeOH/water (1:1) | None | 1 week | Form C |
| Form C | H₂O | None | 1 week | Form C |
| Form E | Acetonitrile | None | 1 week | Form A |
| Form E | MeOH/water (1:1) | None | 1 week | Form C |
| Form A | MeOH | Form B | 1 week | Form A |
| Form A | MeOH | Form C | 1 week | Form A |
| Form A | EtOH/H₂O (1:1) | Form B | 1 week | Form A |
| Form A | EtOH/H₂O (1:1) | Form C | 1 week | Form A |
| Form A | H₂O | Form B | 1 week | Form A |
| Form A | H₂O | Form C | 7 weeks | Form A + C |

6.3 Biological Examples

6.3.1 Biochemical Assays

TOR HTR-FRET Assay. The following is an example of an assay that can be used to determine the TOR kinase inhibitory activity of Compound 1. Compound 1 was dissolved in DMSO and prepared as 10 mM stocks and diluted appropriately for the experiments. Reagents were prepared as follows:

"Simple TOR buffer" (used to dilute high glycerol TOR fraction): 10 mM Tris pH 7.4, 100 mM NaCl, 0.1% Tween-20, 1 mM DTT. Invitrogen recombinant TOR enzyme (cat #PV4753) was diluted in this buffer to an assay concentration of 0.200 μg/mL.

ATP/Substrate solution: 0.075 mM ATP, 12.5 mM MnCl₂, 50 mM Hepes, pH 7.4, 50 mM β-GOP, 250 nM Microcystin LR, 0.25 mM EDTA, 5 mM DTT, and 3.5 μg/mL GST-p70S6.

Detection reagent solution: 50 mM HEPES, pH 7.4, 0.01% Triton X-100, 0.01% BSA, 0.1 mM EDTA, 12.7 μg/mL Cy5-αGST Amersham (Cat#PA92002V), 9 ng/mL α-phospho p70S6 (Thr389) (Cell Signaling Mouse Monoclonal #9206L), 627 ng/mL α-mouse Lance Eu (Perkin Elmer Cat#AD0077).

To 20 μL of the Simple TOR buffer is added 0.5 μL of test compound in DMSO. To initiate the reaction 5 μL of ATP/Substrate solution was added to 20 μL of the Simple TOR buffer solution (control) and to the compound solution prepared above. The assay was stopped after 60 min by adding 5 μL of a 60 mM EDTA solution; 10 μL of detection reagent solution was then added and the mixture was allowed to sit for at least 2 hours before reading on a Perkin-Elmer Envision Microplate Reader set to detect LANCE Eu TR-FRET (excitation at 320 nm and emission at 495/520 nm).

DNA-PK Assay.

DNA-PK assay is performed using the procedures supplied in the Promega DNA-PK assay kit (catalog # V7870). DNA-PK enzyme can be purchased from Promega (Promega cat#V5811).

6.4 Formulation Examples

Certain formulations comprising Compound 1 were prepared and tested for a number of physical and chemical properties. Modifications were then made and subsequent formulations were also tested, until formulations possessing desirable physical and chemical properties were found. The following example describes these formulations and their testing.

Study 1:

A $2^{3-1}$ study was designed to evaluate effect of diluents, disintegrant and drug loading on tablet physical properties and chemical stability. Formulation compositions are shown in Table 15. Initial tablet development was carried out in normal room UV light. The impurity profile is shown in Table 16.

TABLE 15

Formulation composition of various tablet formulations

| Coated tablet batch # Uncoated tablet batch # | HPD020-A-001 PD01-001 | HPD020-A-002 PD01-002 | HPD020-B-001 PD01-003 | HPD020-B-002 PD01-004 |
|---|---|---|---|---|
| Compound 1 (mg) | 0.5 | 0.5 | 5 | 5 |
| Microcrystalline Cellulose (mg) | 63.75 | 83.75 | 59.25 | 79.25 |
| Partially pregelatinized corn starch (mg) | | 10 | | 10 |
| Lactose monohydrate, spray dried (mg) | 30 | | 30 | |
| Crospovidone (mg) | | 4 | 4 | |
| Croscarmellose Na (mg) | 4 | | | 4 |
| Silicon dioxide (mg) | 1 | 1 | 1 | 1 |
| Magnesium Stearate (mg) | 0.75 | 0.75 | 0.75 | 0.75 |
| total uncoated tablet (mg) | 100 | 100 | 100 | 100 |
| Opadry II coating (mg) | 4 | 4 | 4 | 4 |
| total coated tablet (mg) | 104 | 104 | 104 | 104 |
| Color | Pink | Pink | Yellow | Yellow |

TABLE 16

Impurity profile

| Related impurities @ time zero | HPD020-A-001 | HPD020-A-002 | HPD020-B-001 | HPD020-B-002 |
|---|---|---|---|---|
| RRT 0.87 (oxid 1) | 0.27 | 0.31 | 0.26 | 0.24 |
| RRT 0.94 (oxid 2) | 0.32 | 0.33 | 0.22 | 0.25 |
| RRT 0.96 (oxid 3) | 0.56 | 0.56 | 0.47 | 0.48 |
| Total oxidative impurities@t₀ | 1.15 | 1.2 | 0.95 | 0.97 |

Conclusions: Compound 1 is prone to oxidation, especially in the presence of light and poses a chemical stability challenge.

Study 2:

A study was conducted to evaluate the effect of antioxidant (e.g., butylated hydroxyl toluene, BHT) and chelating agent (e.g., disodium edentate, Na₂-EDTA) on the stability of Compound 1 in formulated product. The impact of dosage form (tablet vs capsule) on the stability of Compound 1 was also evaluated.

Formulation compositions are shown in Table 17, while the stability data are presented in Table 18. All of the processes were carried out in dark.

TABLE 17

Formulation composition

| Ingredients | 122711-1 Capsule | 122711-2 Capsule | 122711-3 Capsule | 122711-4 Capsule | 122711-5 Tablet | 122711-6 Capsule |
|---|---|---|---|---|---|---|
| Compound 1 | 0.5 | 0.5 | 0.5 | 0.5 | 0.5 | 0.5 |
| Mannitol (Mannogem EZ) | 84 | 94.1 |  | 93.6 | 83.6 |  |
| MCC PH112 | 10 |  | 94.1 |  | 10 |  |
| Lactose |  |  |  |  |  | 93.6 |
| Sodium starch glycolate | 3 | 3 | 3 | 3 | 3 | 3 |
| stearic acid | 1 | 1 | 1 | 1 | 1 | 1 |
| Butylated hydroxy toluene |  | 0.4 | 0.4 | 0.4 | 0.4 | 0.4 |
| $Na_2$— EDTA | 0.5 |  |  | 0.5 | 0.5 | 0.5 |
| Mg stearate | 1 | 1 | 1 | 1 | 1 | 1 |
| Total | 100 | 100 | 100 | 100 | 100 | 100 |

TABLE 18

Stability data

| Batch # | 122711-1 | | 122711-2 | | 122711-3 | |
|---|---|---|---|---|---|---|
| Dosage Form | Capsule | | Capsule | | Capsule | |
| Time | $T_0$ | 4 wk | $T_0$ | 4 wk | $T_0$ | 4 wk |
| RRT 0.87 | 0.11 | 0.14 | 0.11 | 0.13 | 0.11 | 0.14 |
| RRT 0.94 | 0.08 | 0.10 | 0.09 | 0.11 | 0.08 | 0.11 |
| RRT 0.96 | 0.15 | 0.15 | 0.16 | 0.18 | 0.16 | 0.19 |
| Total of all the oxidative impurities | 0.34 | 0.39 | 0.36 | 0.42 | 0.35 | 0.44 |

| Batch # | 122711-4 | | 122711-5 | | 122711-6 | |
|---|---|---|---|---|---|---|
| Dosage Form | Capsule | | Tablet | | Capsule | |
| Time | $T_0$ | 4 wk | $T_0$ | 4 wk | $T_0$ | 4 wk |
| RRT 0.87 | 0.12 | 0.13 | 0.11 | 0.13 | 0.12 | 0.14 |
| RRT 0.94 | 0.08 | 0.10 | 0.08 | 0.10 | 0.08 | 0.10 |
| RRT 0.96 | 0.14 | 0.16 | 0.14 | 0.16 | 0.15 | 0.17 |
| Total of all the oxidative impurities | 0.34 | 0.39 | 0.33 | 0.39 | 0.35 | 0.41 |

Conclusion: Addition of BHT and $Na_z$-EDTA along with avoiding room light seemed to improve the stability profile of Compound 1 in formulated product. No difference was observed between the stability profile of tablet and capsule dosage forms.

Study 3:

Further study was conducted to study the influence of coating and desiccant on the stability of Compound 1 tablets. All processes were carried out under yellow light to prevent any UV light exposure to the Compound 1 formulations.

A formulation composition is provided in Table 19 and the stability data are presented in Table 20.

TABLE 19

Formulation composition of tablet

| Ingredients | % w/w |
|---|---|
| Compound 1 | 0.5 |
| Mannitol (Mannogem EZ) | 83.6 |
| MCC PH112 | 10 |
| Sodium starch glycolate | 3 |
| stearic acid | 1 |
| Butylated hydroxy toluene | 0.4 |
| $Na_2$-EDTA | 0.5 |
| Mg stearate | 1 |
| Total | 100 |

TABLE 20

Stability data

| | Total 40/75 | | | | | RRT0.87 40/75 | | | | |
|---|---|---|---|---|---|---|---|---|---|---|
| Time, wk | 0 | 2 | 4 | 8 | 12 | 0 | 2 | 4 | 8 | 12 |
| Uncoated | 0.84 | 1.04 | 0.95 | 1.83 | 2.12 | 0.18 | 0.31 | 0.31 | 0.60 | 0.76 |
| Coated | 0.62 | 0.67 | 0.60 | 0.96 | 1.10 | 0.14 | 0.17 | 0.19 | 0.25 | 0.30 |
| Coated/Desiccant | 0.60 | 0.60 | 0.54 | 0.79 | 0.90 | 0.13 | 0.15 | 0.16 | 0.21 | 0.26 |

| | RRT0.94 40/75 | | | | | RRT0.96 40/75 | | | | |
|---|---|---|---|---|---|---|---|---|---|---|
| Time, wk | 0 | 2 | 4 | 8 | 12 | 0 | 2 | 4 | 8 | 12 |
| Uncoated | 0.16 | 0.23 | 0.23 | 0.45 | 0.50 | 0.29 | 0.37 | 0.34 | 0.64 | 0.67 |
| Coated | 0.10 | 0.13 | 0.14 | 0.20 | 0.25 | 0.18 | 0.23 | 0.23 | 0.34 | 0.36 |
| Coated/Desiccant | 0.09 | 0.09 | 0.10 | 0.13 | 0.16 | 0.18 | 0.20 | 0.21 | 0.27 | 0.30 |

Conclusion: Coated tablets showed lower amounts of oxidative impurities compared to uncoated tablets. The presence of a desiccant showed slight improvement in stability.

Study 4:

Effect of BHT and EDTA in the tablet formulation on the stability of Compound 1 was evaluated. All processes were carried out under yellow light to prevent any UV light exposure to the Compound 1 formulations.

Formulation compositions are shown in Table 21 and stability data are presented in qs=quantum sufficit or quantity sufficient (enough to reach 100%).

Table 22. Film-coated tablets were manufactured using a blend/screen/blend process followed by compression and coating. The entire process was carried out under yellow light to minimize oxidation. Butylated hydroxytoluene (BHT) and disodium EDTA were found to improve the chemical stability of the active ingredient of the formulation.

extremes of the formulation. (Tables 23-28 below). Due to the maximum interaction between the API and excipients, low strength tablets were developed to determine the chemical stability of the active in a tablet. High strength tablets were developed to determine how the API dictates the mechanical properties of the tablet and to diagnose any potential formulation barriers.

Preparation of Tablets:

The blends according to Table 23 to Table 28 were prepared as follows. Microcrystalline cellulose was weighed and added to an amber colored straight sided glass jar. The lid was closed and the jar shaken in order to coat the inside of the jar. Active ingredient (Compound 1) was then added and blended for 10 minutes at 46 rpm using a Turbula mixer. The blend was passed through a 25 mesh screen and blended again for 10 minutes at 46 rpm using a Turbula mixer. The resulting blend was passed through a 35 mesh screen. Remaining excipients were then added, except for lubricant (magnesium stearate). The resulting mixture was blended for 10 minutes at 46 rpm using a Turbula mixer. 6 grams of the resulting blend was added an amber glass jar, lubricant was added and blended for 1 minute and 35 seconds at 46 rpm using a Turbula mixer. For low strength tablet formulations, 140 mg tablets were prepared using a 7.14 mm punch and die. For high strength tablet formulations, 400 mg tablets were prepared using a 10.3 mm punch and die.

TABLE 21

Exemplary Tablet Formulations

| | % w/w (mg) Batch # | | | | | | |
|---|---|---|---|---|---|---|---|
| Ingredients | 1 (PD01-070) | 2 (PD01-071) | 3 (PD01-069) | 4 (PD01-068) | 5 (PD01-074) | 6 (PD01-075) | 7 |
| Compound 1 (active ingredient) | 10 | 10 | 10 | 10 | 5 | 5 | 5 |
| Mannitol (Mannogem EZ) | qs | qs | qs | qs | 64.85 | 64.85 | 64.35 |
| Microcrystalline Cellulose (PH 112) | 25 | 25 | 25 | 25 | 25 | 25 | 25 |
| Sodium Starch Glycolate | 3 | 3 | 3 | 3 | 3 | 3 | 3 |
| Silicon dioxide | 1 | 1 | 1 | 1 | 1 | 1 | 1 |
| Stearic acid | 0.5 | 0.5 | 0.5 | 0.5 | 0.5 | 0.5 | 0.5 |
| Disodium EDTA | | | 0.5 | 0.5 | | | 0.5 |
| BHT | | 0.4 | | 0.4 | | | |
| Magnesium Stearate | 0.65 | 0.65 | 0.65 | 0.65 | 0.65 | 0.65 | 0.65 |
| Total | 100 | 100 | 100 | 100 | 100 | 100 | 100 |
| Color | Yellow | Yellow | Yellow | Yellow | Yellow | Pink | | qs = quantum sufficit or quantity sufficient (enough to reach 100%).

TABLE 22

Stability Data

| | Total impurities at 40° C./75% RH | | | |
|---|---|---|---|---|
| Batch# | 1(PD01-070) | 2(PD01-071) | 3(PD01-069) | 4(PD01-068) |
| time 0 | 0.77 | 0.66 | 0.58 | 0.62 |
| 1 month | 0.69 | 0.6 | 0.62 | 0.65 |
| 2 month | 0.79 | 0.69 | 0.72 | 0.75 |
| 3 month | 1.07 | 0.91 | 0.87 | 0.85 |

Conclusion: Formulations with EDTA and/or BHT both showed lower oxidative impurities compared to formulations without EDTA and BHT.

Blend Compatibility Experiments.

Based on binary excipient compatibility results, blend compatibility was completed to determine which combination of excipients were compatible with Compound 1. After being stressed for 4 weeks at 40° C./75% RH, Compound was stable with all excipient combinations. Following blend compatibility, tablets were compressed using 3 formulations at two strengths, low (1 mg) and high (25 mg) to study the

TABLE 23

Low Strength Tablet Formulation #1

| Brand | Ingredient | Source | Amount (weight %) |
|---|---|---|---|
| | Compound 1 | | 0.7 |
| Avicel PH-102 | microcrystalline cellulose | FMC Biopolymer | 38.1 |
| Pearlitol 160C | mannitol | Roquette | 57.2 |
| Ac-di-Sol | sodium carboxymethylcellulose | FMC Biopolymer | 3.0 |
| Tablube | magnesium stearate | Nitika Chemicals | 1.0 |

TABLE 24

Low Strength Tablet Formulation #2

| Brand | Ingredient | Source | Amount (weight %) |
|---|---|---|---|
|  | Compound 1 |  | 0.7 |
| Avicel PH-102 | microcrystalline cellulose | FMC Biopolymer | 75.3 |
| Starch 1500 | pregelatinized starch | Colorcon | 20.0 |
| Ac-di-Sol | sodium carboxymethylcellulose | FMC Biopolymer | 3.0 |
| Tablube | magnesium stearate | Nitika Chemicals | 1.0 |

TABLE 25

Low Strength Tablet Formulation #3

| Brand | Ingredient | Source | Amount (weight %) |
|---|---|---|---|
|  | Compound 1 |  | 0.7 |
| Avicel PH-102 | microcrystalline cellulose | FMC Biopolymer | 38.1 |
| Tablettose 80 | Lactose monohydrate | Meggle Pharma | 57.2 |
| Ac-di-Sol | sodium carboxymethylcellulose | FMC Biopolymer | 3.0 |
| Tablube | magnesium stearate | Nitika Chemicals | 1.0 |

TABLE 26

High Strength Tablet Formulation #1

| Brand | Ingredient | Source | Amount (weight %) |
|---|---|---|---|
|  | Compound 1 |  | 25.0 |
| Avicel PH-102 | microcrystalline cellulose | FMC Biopolymer | 28.4 |
| Pearlitol 160C | mannitol | Roquette | 42.6 |
| Ac-di-Sol | sodium carboxymethylcellulose | FMC Biopolymer | 3.0 |
| Tablube | magnesium stearate | Nitika Chemicals | 1.0 |

TABLE 27

High Strength Tablet Formulation #2

| Brand | Ingredient | Source | Amount (weight %) |
|---|---|---|---|
|  | Compound 1 |  | 25.0 |
| Avicel PH-102 | microcrystalline cellulose | FMC Biopolymer | 51.0 |
| Starch 1500 | pregelatinized starch | Colorcon | 20.0 |
| Ac-di-Sol | sodium carboxymethylcellulose | FMC Biopolymer | 3.0 |
| Tablube | magnesium stearate | Nitika Chemicals | 1.0 |

TABLE 28

High Strength Tablet Formulation #3

| Brand | Ingredient | Source | Amount (weight %) |
|---|---|---|---|
|  | Compound 1 |  | 25.0 |
| Avicel PH-102 | microcrystalline cellulose | FMC Biopolymer | 28.4 |
| Tablettose 80 | Lactose monohydrate | Meggle Pharma | 42.6 |
| Ac-di-Sol | sodium carboxymethylcellulose | FMC Biopolymer | 3.0 |
| Tablube | magnesium stearate | Nitika Chemicals | 1.0 |

The above formulations were subjected to a 6 week stability study.

HPLC analysis was performed using a Kinetex C18, 4.6×100 mm, 2.6 μm column. Mobile phase A: 20 mM ammonium acetate: acetonitrile (95:5 v/v); Mobile Phase B: 20 mM ammonium acetate: acetonitrile (10:90 v/v) using the following gradient:

| Time (min) | A % | B % | Curve |
|---|---|---|---|
| 0 | 100 | 0 | Linear |
| 1 | 100 | 0 | Linear |
| 10 | 0 | 100 | Linear |
| 10.1 | 100 | 0 | Linear |
| 16 | 100 | 0 | Linear |

Flow rate: 1 mL/min; column temperature: 40° C.; UV detection 250 nm; Injection vol.: 12 μL; run time: 16 min.

Low strength tablets were stressed for 6 weeks at 50° C./80% RH; where assay and dissolution was tested. After 6 weeks at 50° C./80% RH, the assay of the low strength tablets (1 mg) were comparable with the initial time point for the 3 formulations put on stability. The initial and 6 week dissolution for the low strength tablets were comparable within +/−5% for Formulation 1 and with +/−10% for Formulations 5 and 9.

| Week | assay | purity |
|---|---|---|
|  | Formulation 1 | |
| 0 | 96.0% | 98.2% |
| 6 | 98.6% | 98.6% |
|  | Formulation 5 | |
| 0 | 96.1% | 98.3% |
| 6 | 94.1% | 98.6% |
|  | Formulation 9 | |
| 0 | 105.7% | 98.4% |
| 6 | 106.2% | 98.7% |

High strength tablets were stressed for 4 weeks at 40° C./75% RH. Initially, the formulation contained 25% drug loading. However, the physico-mechanical properties of the compound would not allow for the development of tablets with acceptable physico-mechanical properties. Therefore, the drug loading was decreased to 10%. At the lower drug loading, the formulation had much more acceptable properties for tableting on a high speed press. After 4 weeks at 40° C./75% RH, no significant changes were observed in the dissolution of the high strength (25 mg) tablets for the 3 formulations.

Based on the results of the experiments, it would be difficult to formulate a tablet when the drug loading is higher than 10%. At higher drug loadings, the physico-mechanical properties of the formulation are dictated by the API rather than the excipients. At high drug loadings, the poor physical properties of the API lead towards cohesiveness and a poor flowability. A poorly flowing formulation would make it difficult to reproducibly manufacture tablets on a high speed tablet press. For both low and high strength tablets, Formulation 1 gave dissolution profiles with the smallest variation after being put on stability.

6.5 Tautomerism of Compound 1

Figure 26:
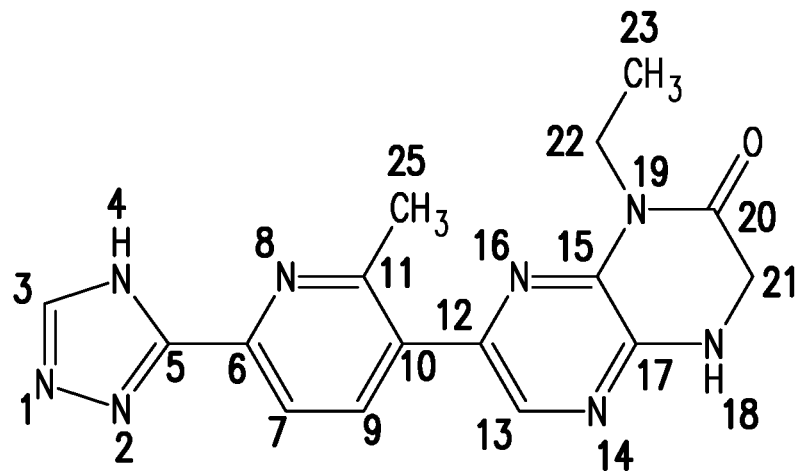
FIG. 26 depicts the tautomers of Compound 1.
Figure 26:
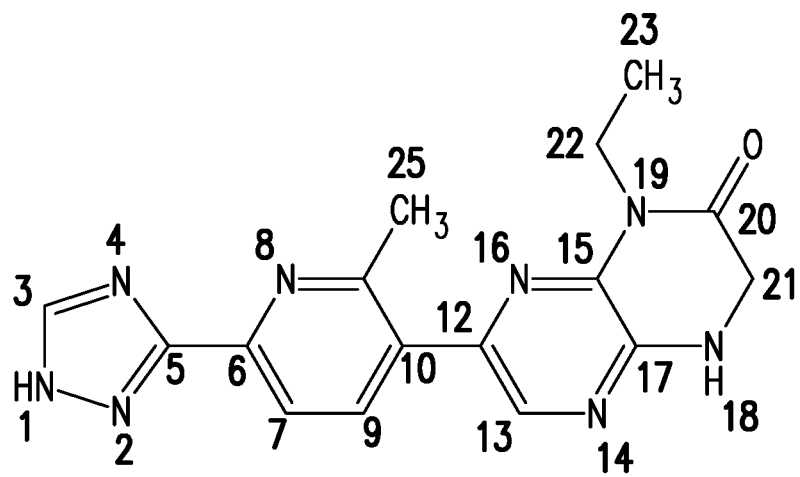
Figure 27:
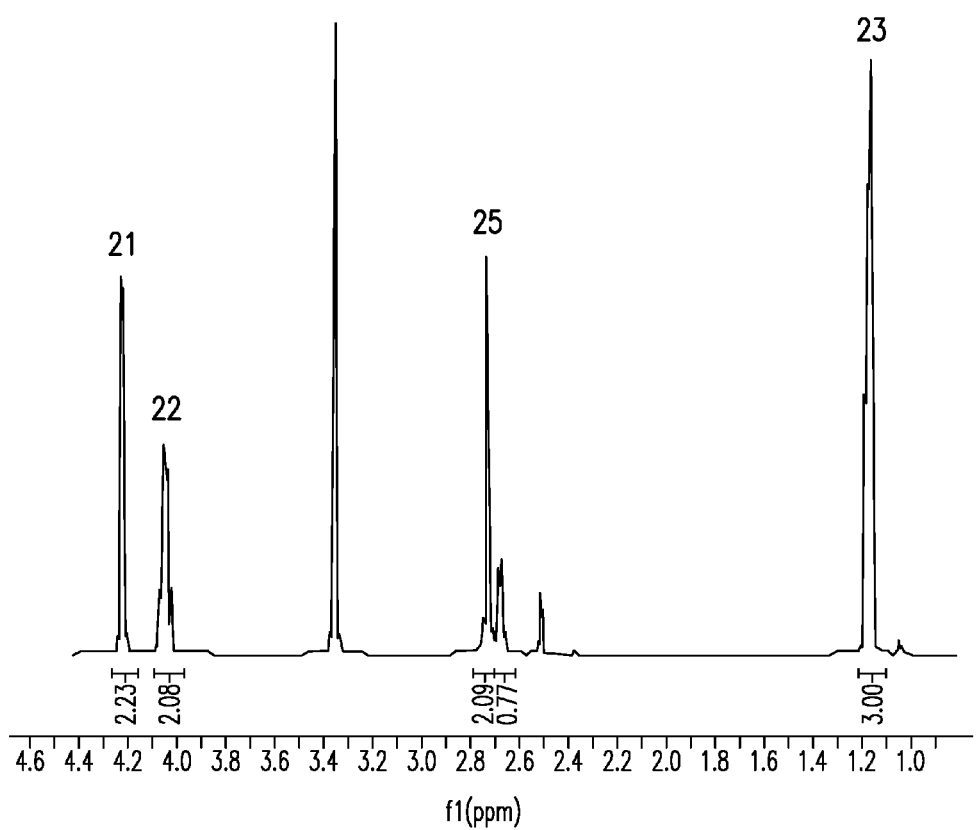
FIG. 27 depicts $^1$H NMR spectra of Compound 1 major tautomer.
Figure 27:
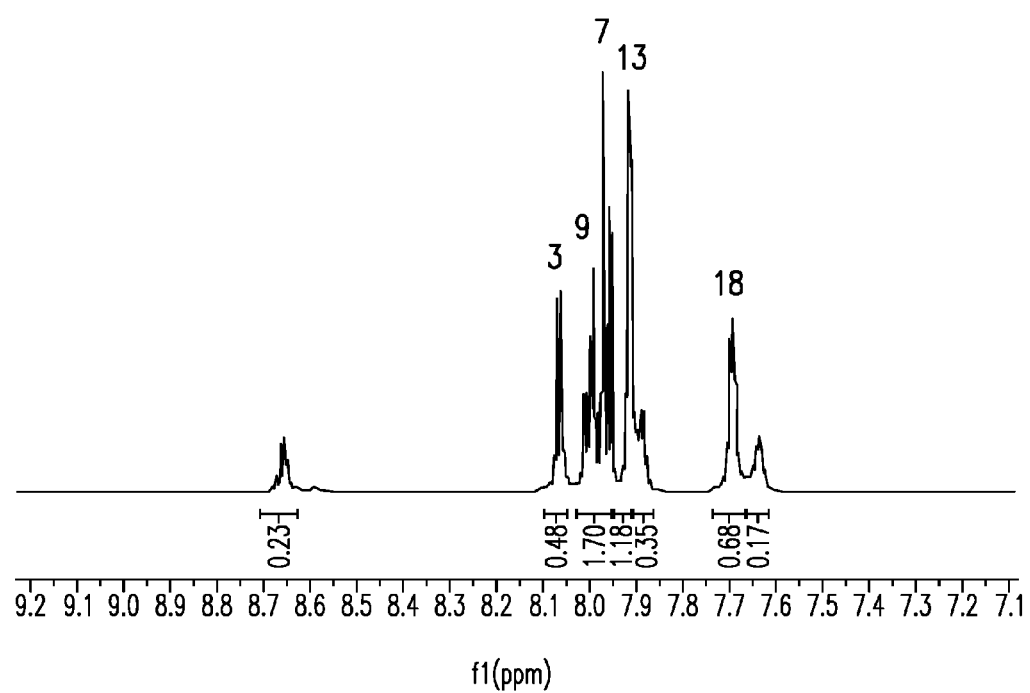
Figure 27:
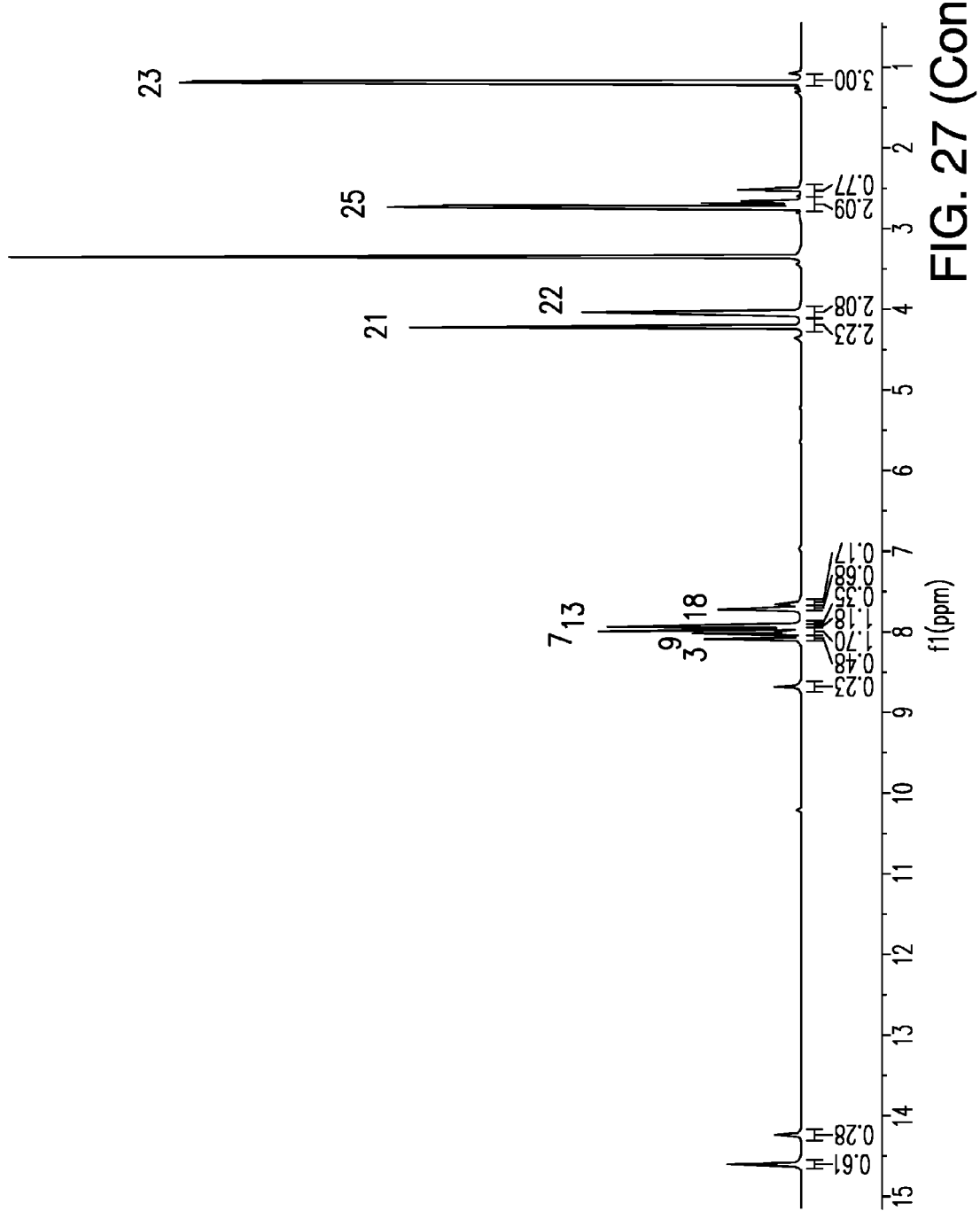
Figure 28:
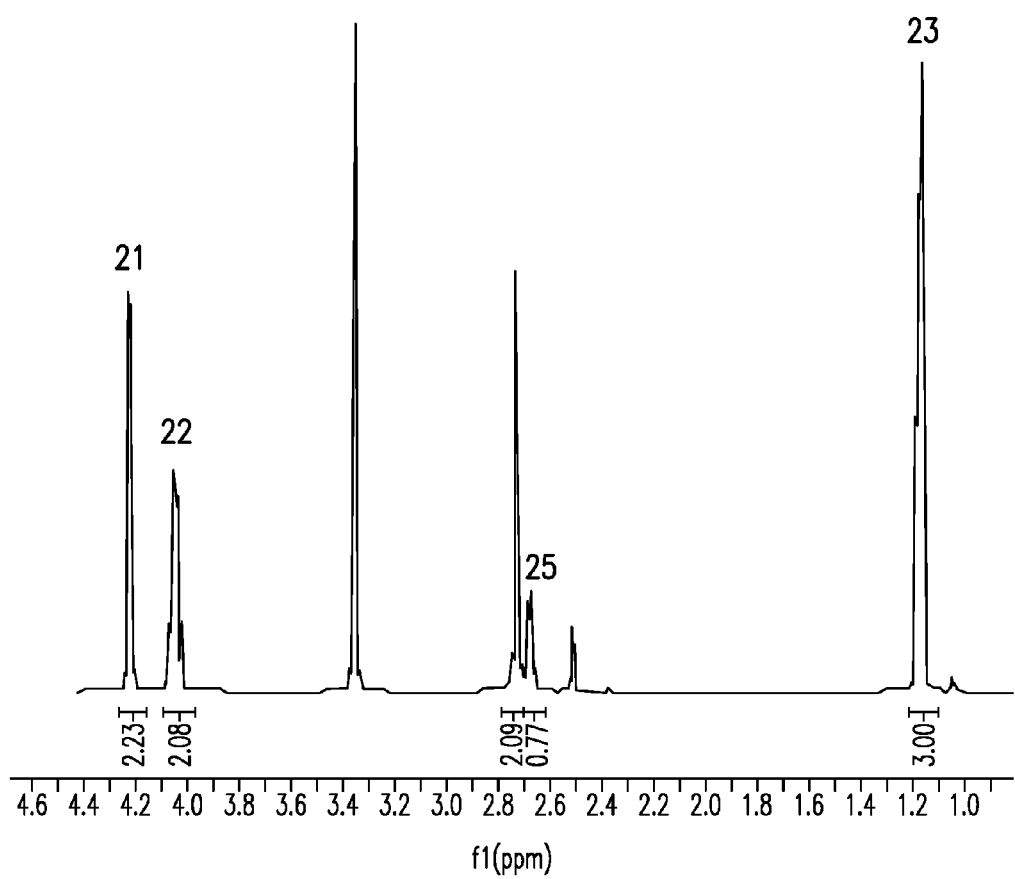
FIG. 28 depicts $^1$H NMR spectra of Compound 1 minor tautomer.
Figure 28:
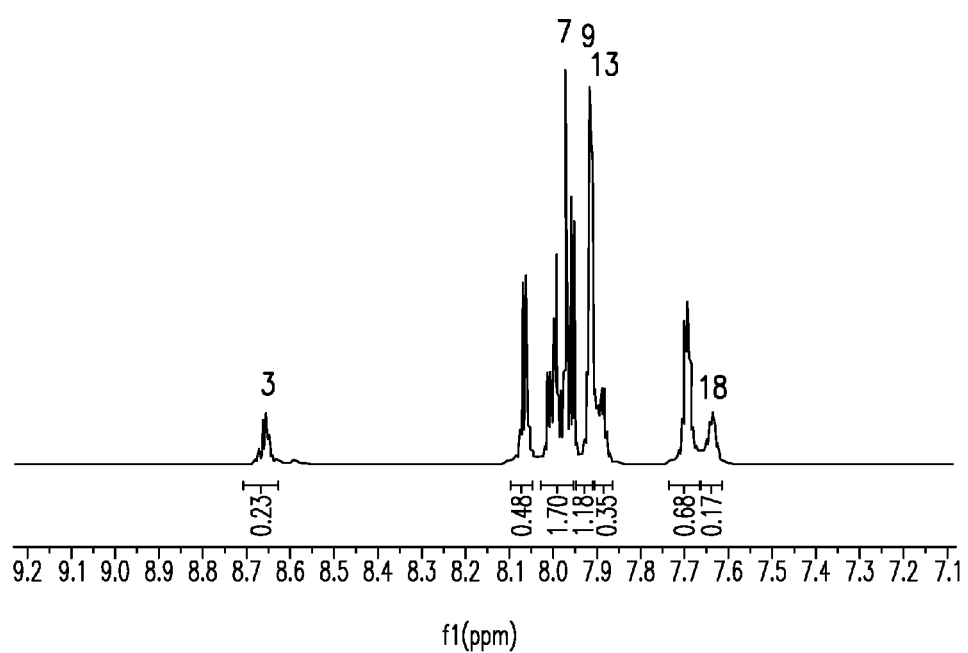
Figure 28:
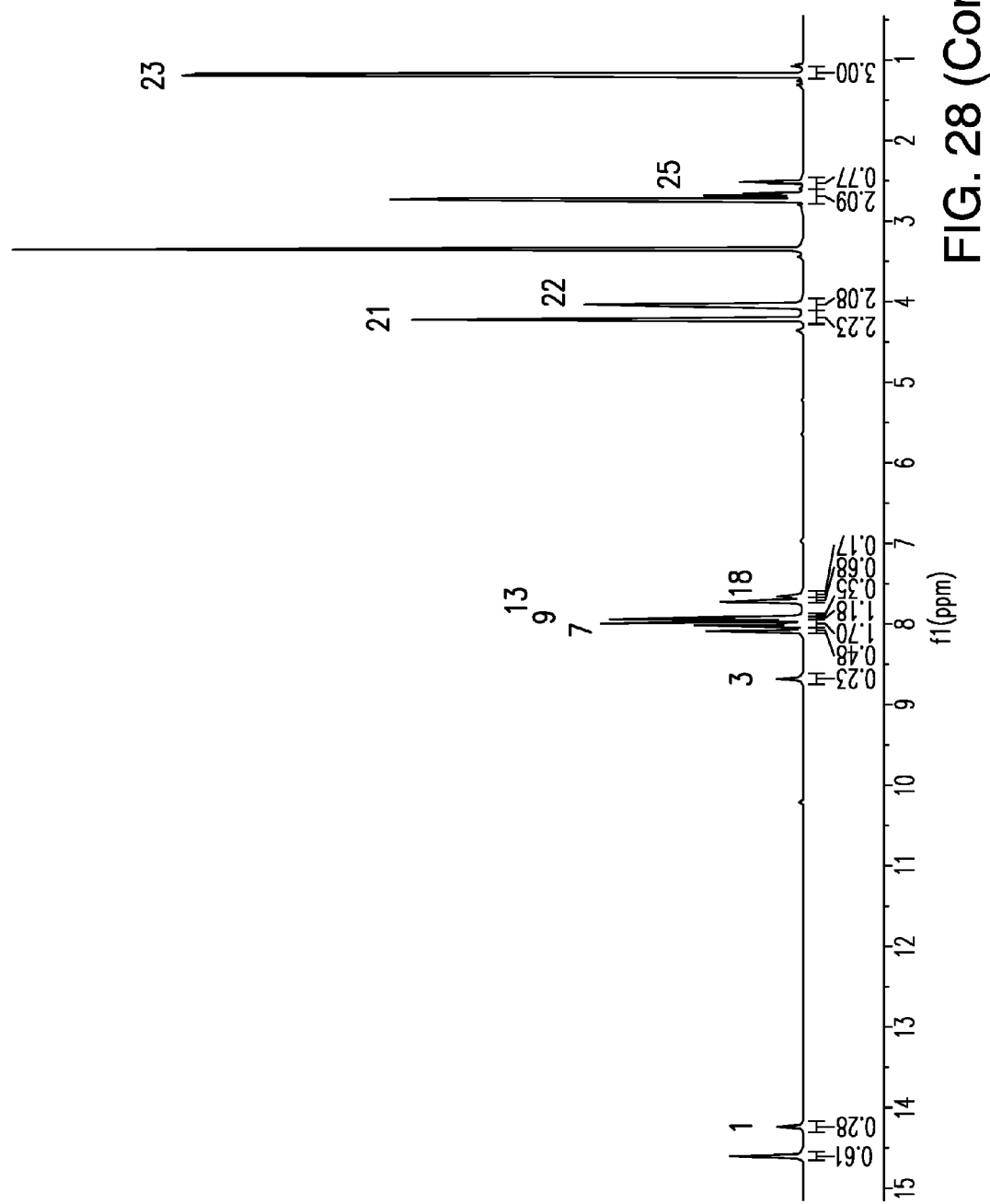
Figure 29:
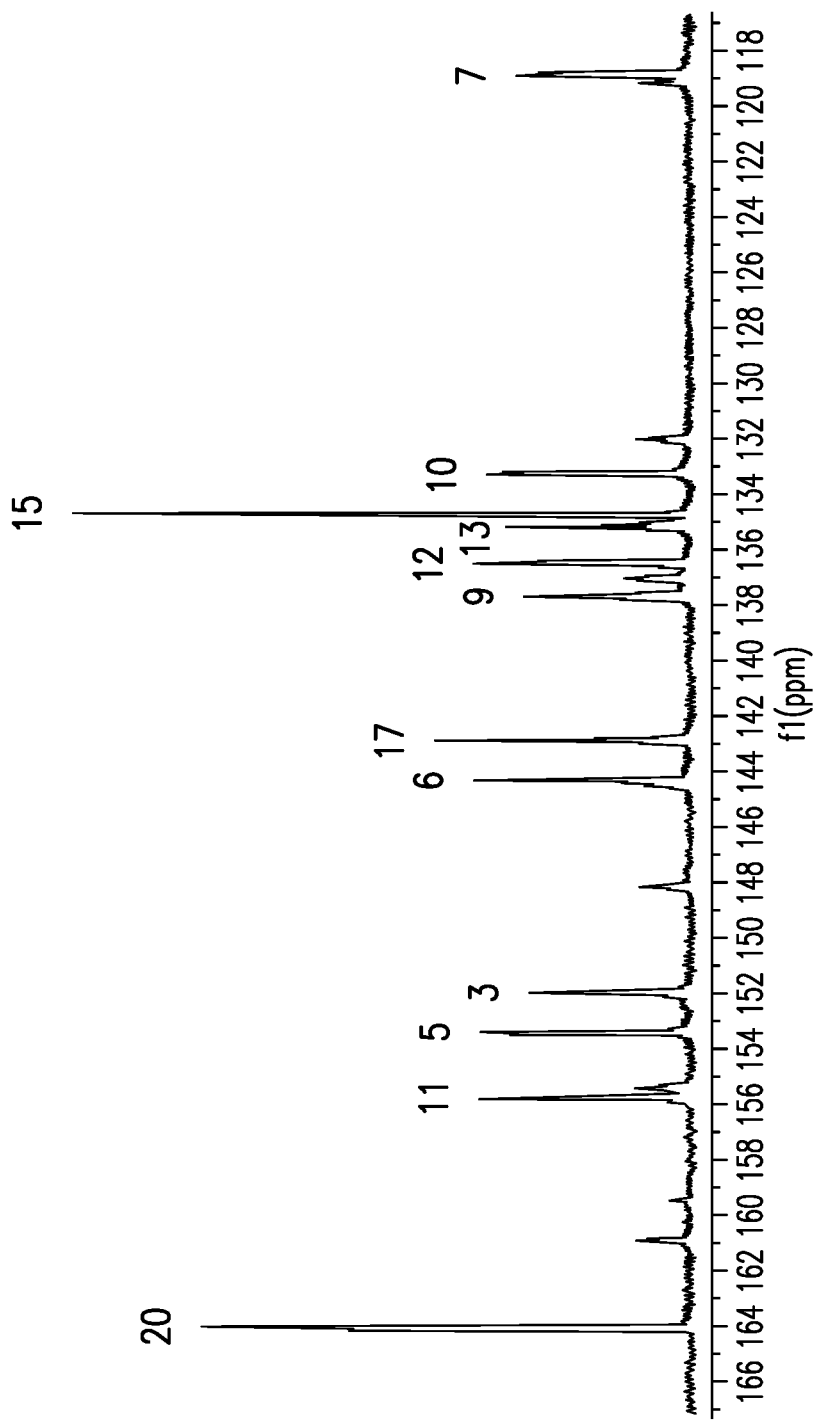
FIG. 29 depicts $^{13}$C NMR spectra of Compound 1 major tautomer.
Figure 29:
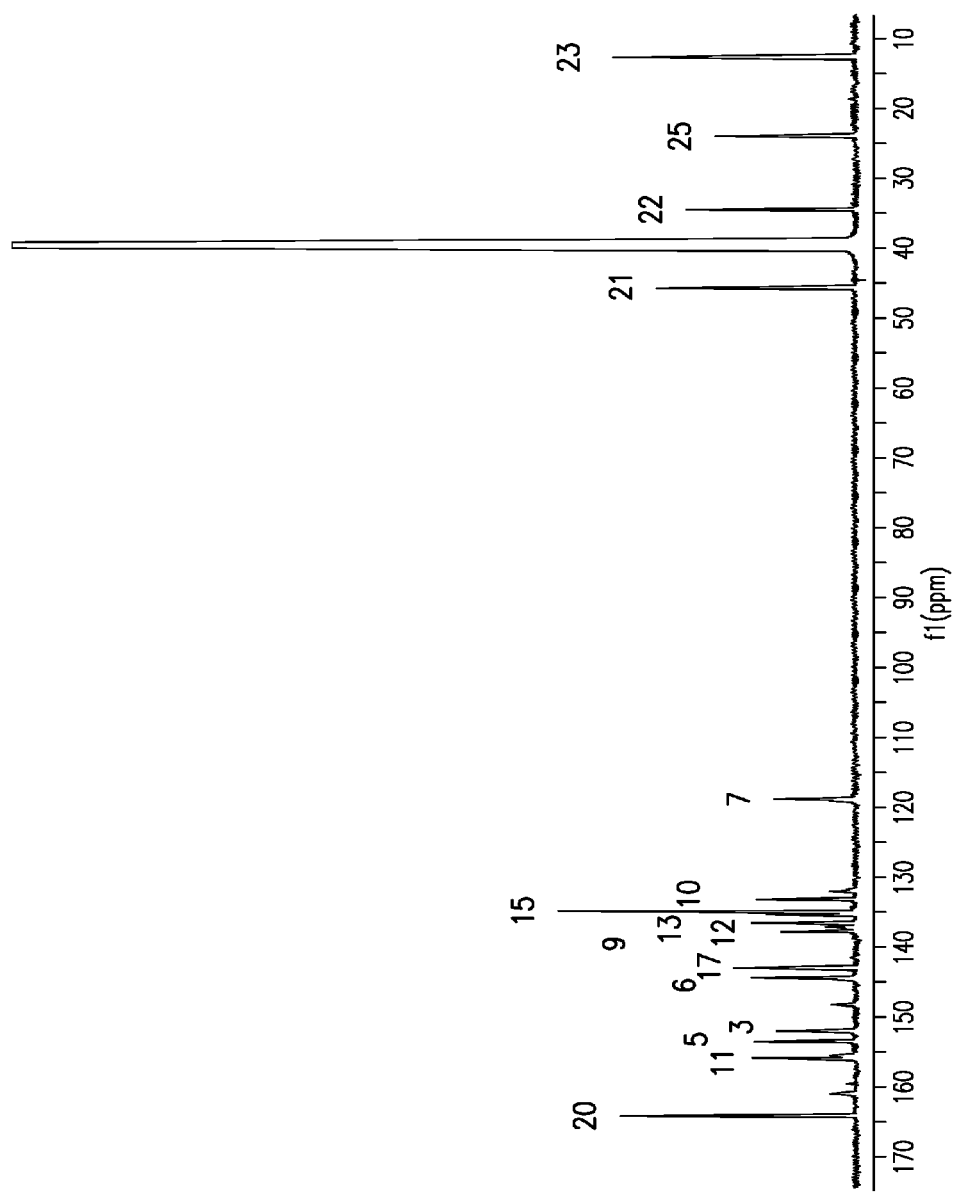
Figure 30:
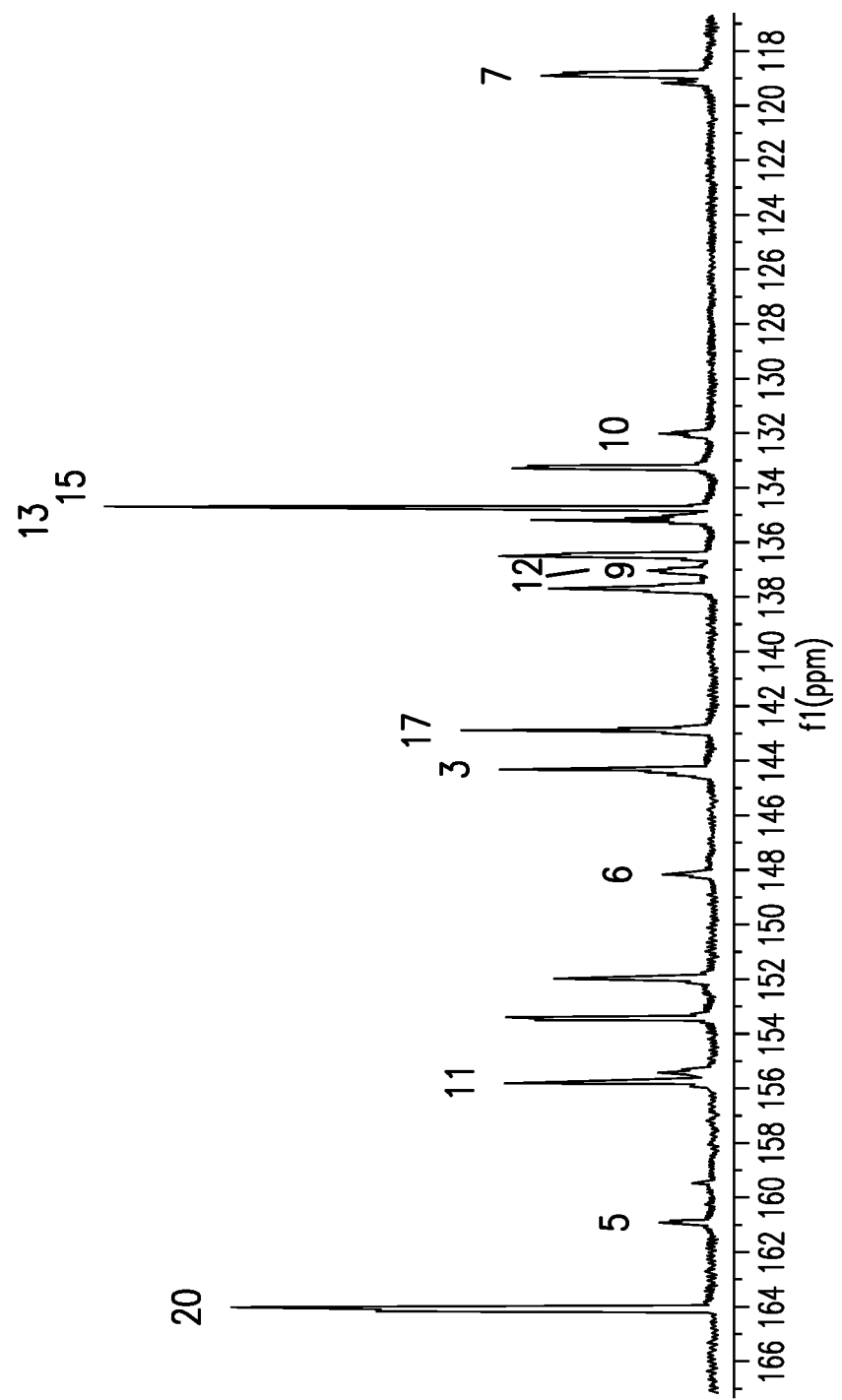
FIG. 30 depicts $^{13}$C NMR spectra of Compound 1 minor tautomer.
Figure 30:
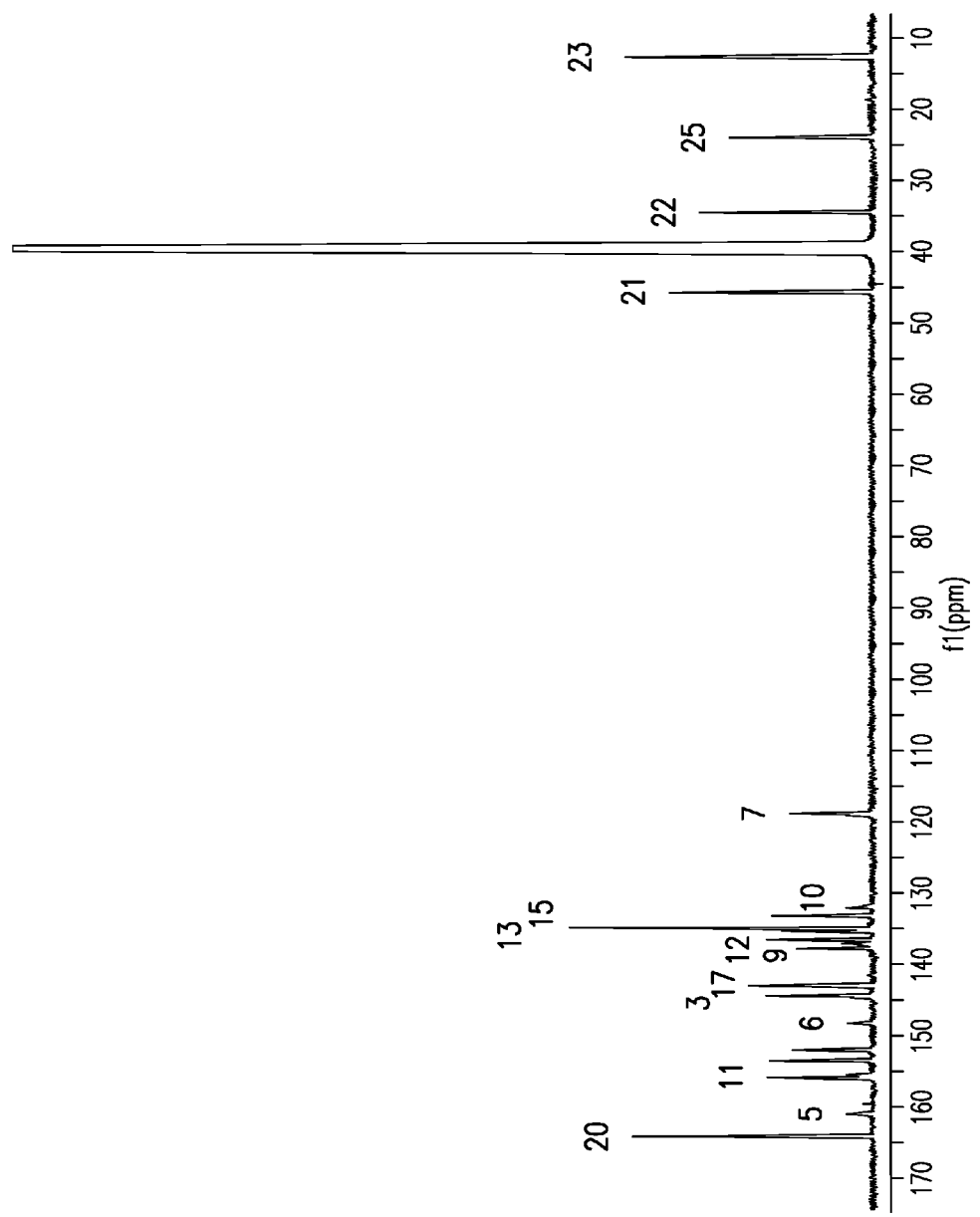
Figure 31:
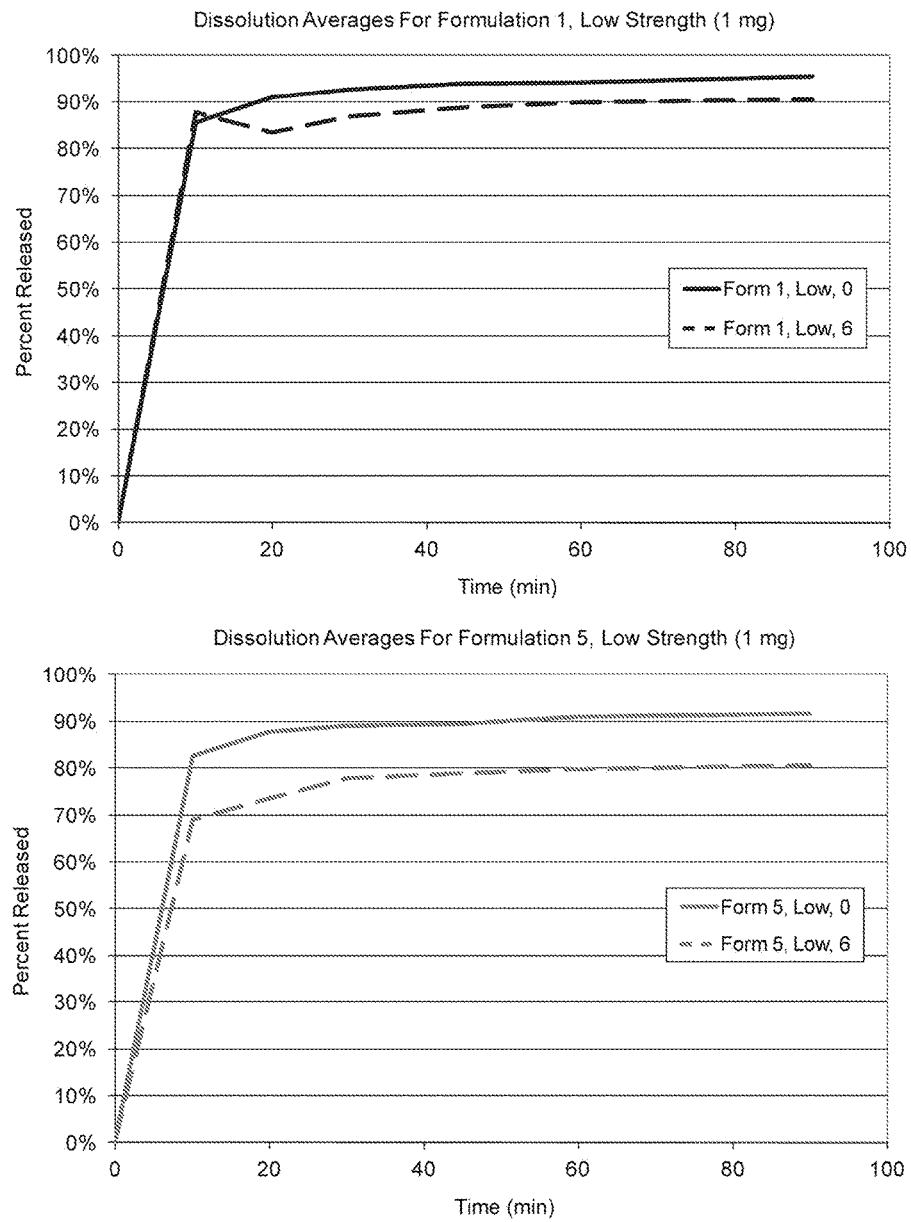
FIG. 31 depicts Dissolution Averages for low strength formulations.
Figure 31:
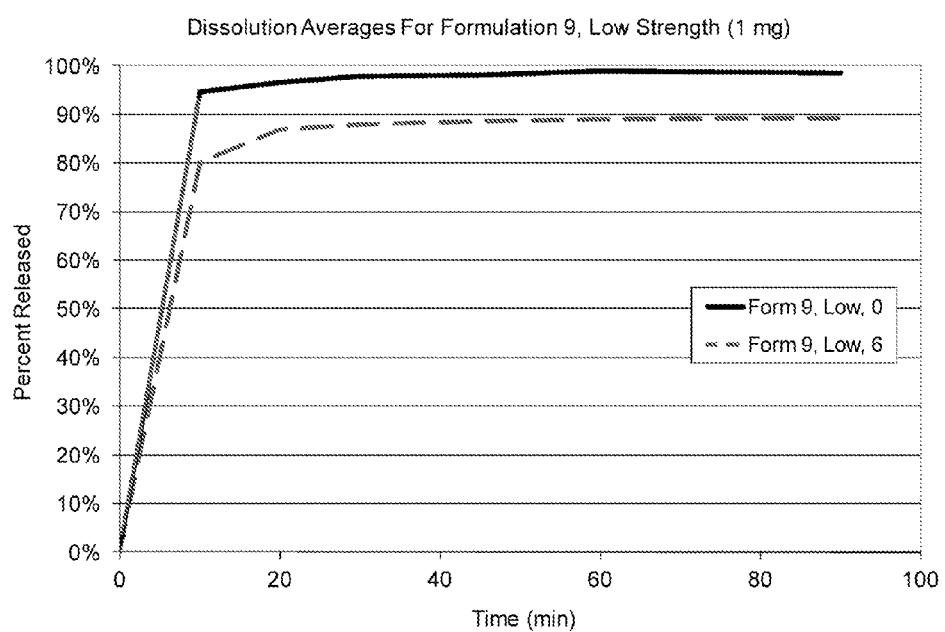
Figure 32:
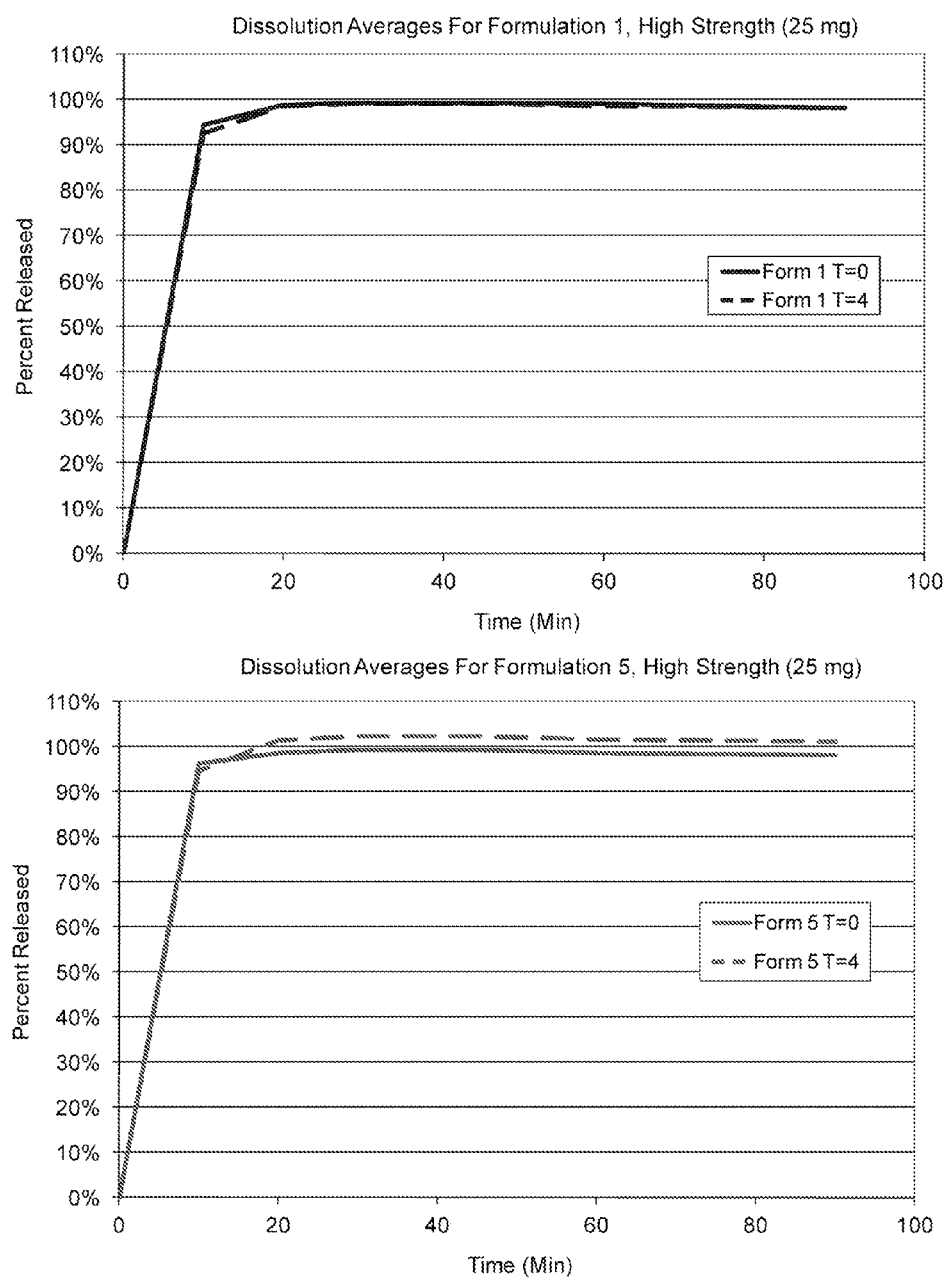
FIG. 32 depicts Dissolution Averages for high strength formulations.
Figure 32:
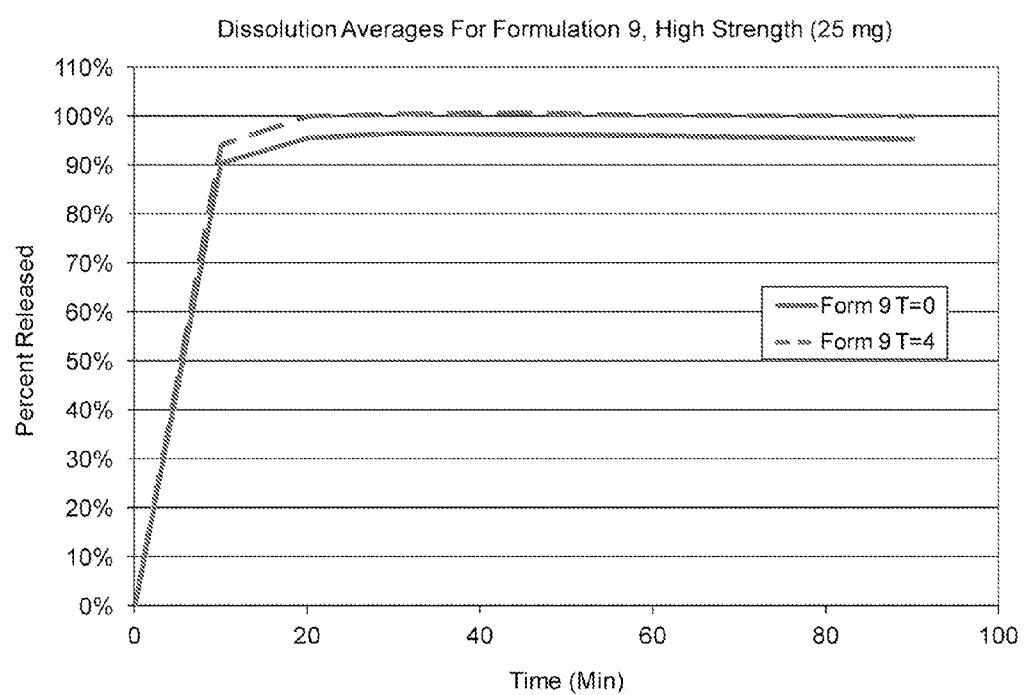

NMR studies were performed to analyze the tautomers of Compound 1. Two tautomers were observed at a relative abundance of 70/30 by NMR. See FIG. 26. A diagnostic $^{13}$C chemical shift of approx. 161 ppm for position 5 of the minor tautomer was observed, as compared to an approx. 150 ppm chemical shift for position 5 of the major tautomer. HMBC correlation between 1H and 3C/5C confirmed the result. NMR data are shown in FIGS. 27-30 and Table 29 and Table 30 below. All data were collected on a Varian Inova 500 NMR spectrometer in DMSO-$d_6$ at 25° C. with a Varian pentaprobe using vendor supplied pulse sequences. Quantitative $^1$H and $^{13}$C data were acquired with a 10 second relaxation delay in the presence of Cr(III) acetyl-acetonide.

TABLE 29

$^1$H and $^{13}$C NMR Signals for the tautomers of Compound 1

| Position | 13C | 1H |
|---|---|---|
| 3 | 152.0 | 8.07 |
| 4 | NA | 14.60 |
| 5 | 153.4 | NA |
| 6 | 144.3 | NA |
| 7 | 118.8 | 7.97 |
| 9 | 137.7 | 8.01 |
| 10 | 133.2 | NA |
| 11 | 155.8 | NA |
| 12 | 136.4 | NA |
| 13 | 135.2 | 7.92 |
| 15 | 134.7 | NA |
| 17 | 142.9 | NA |
| 18 | NA | 7.70 |
| 20 | 164.1 | NA |
| 21 | 45.7 | 4.21 |
| 22 | 34.6 | 4.04 |
| 23 | 12.4 | 1.17 |
| 25 | 23.9 | 2.72 |

TABLE 30

$^1$H and $^{13}$C NMR Signals for the tautomers of Compound 1

| Position | 13C | 1H |
|---|---|---|
| 1 | NA | 14.24 |
| 3 | 144.5 | 8.67 |
| 5 | 160.9 | NA |
| 6 | 148.1 | NA |
| 7 | 119.1 | 7.97 |
| 9 | 137.1 | 7.92 |
| 10 | 132.0 | NA |
| 11 | 155.4 | NA |
| 12 | 137.0 | NA |
| 13 | 135.0 | 7.92 |
| 15 | 134.7 | NA |
| 17 | 142.8 | NA |
| 18 | NA | 7.64 |
| 20 | 164.1 | NA |
| 21 | 45.7 | 4.21 |
| 22 | 34.6 | 4.04 |
| 23 | 12.4 | 1.17 |
| 25 | 23.9 | 2.66 |

6.6 Bioavailability/Food Effect Study

A tablet formulation of Compound 1 has been developed as an alternative to active pharmaceutical ingredient (API)-in-capsule (AIC) for future clinical studies provided the pharmacokinetic (PK) profiles of the two formulations are comparable. The PK of Compound 1 has been well characterized in subjects administered various doses and dosage regimens of Compound 1 AIC. This bioavailability/food effect substudy is designed to provide intrasubject PK comparisons for the current AIC and the newly formulated tablet, and to assess the effect of food on Compound 1 bioavailability to determine whether fasting restrictions around Compound 1 dosing can be lifted. The bioavailability study will involve up to 12 evaluable adult subjects with any solid tumor.

In a prior clinical study, Compound 1 was considered to be well tolerated across the dose range evaluated, and to show a safety profile consistent with published findings for other agents targeting mTOR and related cellular pathways. Per the protocol, both 25 mg QD and 10 mg BID were identified to be maximum tolerated dose (MTD) schedules, with the latter selected for further evaluation.

Based on the good tolerability of Compound 1, the intensity of routine monitoring procedures is reduced in this substudy to limit the investigative burden on subjects without compromising safety.

The primary objectives of this substudy, which is restricted to adults 18 years or older with any advanced solid tumor, are: (1) to characterize and evaluate the pharmacokinetics of Compound 1 administered as a single oral dose of tablet and API-in-capsule formulations and (2) to characterize the effect of food on the pharmacokinetics of Compound 1 administered as a single oral dose of Compound 1 with a high-fat meal.

The primary endpoints will characterize Compound 1 plasma and urinary PK in the same subjects under fasted conditions after administration of Compound 1 AIC and tablet, and under fed and fasted conditions after administration of the formulated tablet, for the following variables: $C_{max}$, $AUC0_{-inf}$, $AUC_{0-t}$, $T_{max}$, $t_{1/2}$, CL/F and Vz/F. PK parameters will be estimated using noncompartmental analyses.

Figure 33:
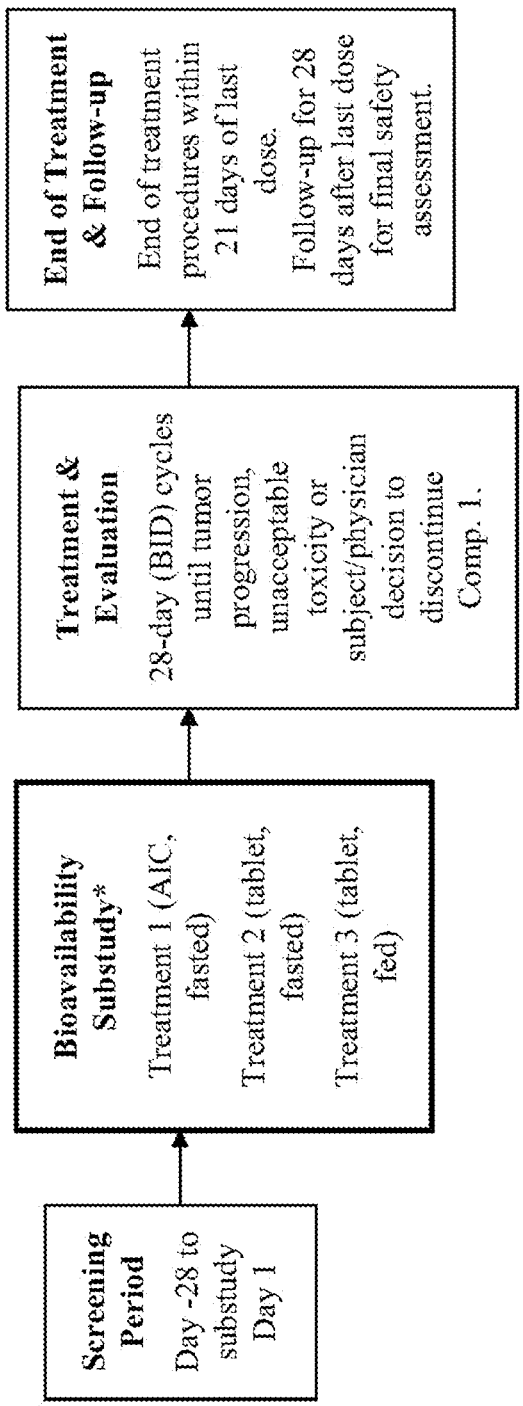
FIG. 33 depicts the overall Bioavailability Study design. ★Cross-over treatment sequence is randomized in blocks of 4 subjects. Each subject receives all 3 treatments.

The study has an open-label, randomized, single-dose, 3-treatment, 3-period, and 3-sequence design for 12 subjects. Subjects will complete this PK substudy over a period of approximately 10 to 19 days prior to starting the main phase of the study (FIG. 33). Three treatments will be administered in 3 separate periods to the same subjects following overnight fasts of at least 6 hours, as follows:

Treatment 1: One 10 mg reference Compound 1 AIC administered under fasted conditions.

Treatment 2: One 10 mg test Compound 1 tablet administered under fasted conditions.

Treatment 3: One 10 mg test Compound 1 tablet administered under fed conditions.

On Day 1 of Period 1, subjects will be randomized to one of the following 3 treatment sequences:

Sequence 1 (n=4): Treatment 1→Treatment 2→Treatment 3.

Sequence 2 (n=4): Treatment 2→Treatment 3→Treatment 1.

Sequence 3 (n=4): Treatment 3→Treatment 1→Treatment 2.

On Day 1 of Treatments 1 and 2, subjects will be administered a single dose of Compound 1 AIC or tablet, respectively with approximately 240 mL of non-carbonated, room temperature water. PK blood draw sampling will be predose, and at 0.5 hr±5 min, 1 hr±5 min, 1.5 hr±10 min, 3 hr±10 min, 5 hr±15 min, 8 hr±15 min, 24 hr±30 min, and 48 hr 60 min postdose.

On Day 1 of Treatment 3, 30 mins±5 mins following supervised feeding of a standardized breakfast, subjects will be administered a single dose of Compound 1 tablet. The timepoints for PK blood draw sampling will be pre-dose, and at 0.5 hr±5 min, 1 hr±5 min, 1.5 hr±10 min, 3 hr±10 min, 5 hr±15 min, 8 hr±15 min, 24 hr±30 min, and 48 hr 60 min postdose.

The 48-hour blood draws may be eliminated if results from the initial subjects show it to be unnecessary.

A standard high-fat meal provided at the investigational site will be consumed approximately 30 minutes prior to Treatment 3. The start and end time of meal consumption and approximate percent of meal consumed will be recorded. This meal comprises high-fat (approximately 50% of the total caloric content of the meal), high-calorie (approximately 800 to 1000 calories) nutrition with approximately 150, 250 and 500 to 600 calories derived from protein, carbohydrates and fat, respectively. A typical high-fat meal consists of 2 eggs fried in butter, 2 strips of bacon, 2 slices of toast with butter, 4 ounces of hash brown potatoes and 8 ounces of whole milk. Substitutions can be made as long as the meal provides a similar amount of calories from protein, carbohydrate and fat, and has comparable meal volume and viscosity.

The tablet will be administered with approximately 240 mL of non-carbonated, room temperature water. After dosing, subjects will continue to fast until at least 3 hours after dosing.

The interdose washout interval between Period 1, Day 1 and Period 2, Day 1, and Period 2, Day 1 and Period 3, Day 1 may range between 48 and 168 hours (2 to 7 days) depending on subject needs/schedules.

An evaluable subject is one who completes at least either Treatments 1 and 2 or Treatments 2 and 3; except in special circumstances approved by the Sponsor, all 3 treatment assessments will be completed by each subject. Non-evaluable subjects will be replaced at the discretion of the Sponsor.

After the final PK sample is collected on Day 3 of Period 3, subjects start the Treatment and Evaluation study phase of continuous dosing of daily 28-day cycles of Compound 1 AIC capsules without the need for rescreening.

Inclusion criteria are: (1) Understand and voluntarily sign an informed consent document before any study-related assessments/procedures are conducted; (2) Men and women, 18 years or older, with histological or cytological confirmation of advanced unresectable solid tumors, CLL, NHL, or MM, including those who have progressed on (or not been able to tolerate) standard anticancer therapy or for whom no other conventional therapy exists; subjects with Ewing's Sarcoma may be 12 years or older (3) Consent to screening tumor biopsy; (4) ECOG PS of 0 or 1; (5) the following laboratory values: (i) absolute neutrophil count (ANC)≥1.5× $10^9$/L; (ii) hemoglobin (Hgb)≥9 g/dl; (iii) platelets (plt)≥ $100 \times 10^9$/L; (iv) potassium within normal range, or correctable with supplements; (v) AST/SGOT and ALT/SGPT≤2.5×Upper Limit of Normal (ULN) or ≤5.0×ULN if liver tumor is present; (vi) serum total bilirubin ≤1.5× ULN or ≤2×ULN if liver tumor is present; (vii) serum creatinine ≤1.5×ULN, or 24-hr clearance ≥50 mL/min; and (viii) negative serum or urine pregnancy test within 72 hrs before starting study treatment in females of childbearing potential; and (6) able to adhere to the study visit schedule and other protocol requirements.

Exclusion criteria are: (1) Symptomatic central nervous system metastases; (2) Known acute or chronic pancreatitis; (3) Any peripheral neuropathy ≥NCI CTCAE grade 2; (4) Persistent diarrhea or malabsorption ≥NCI CTCAE grade 2, despite medical management. Impaired ability to swallow; (5) Impaired cardiac function or clinically significant cardiac diseases, including any of the following: (i) LVEF≤45% as determined by MUGA scan or ECHO; (ii) Complete left bundle branch, or bifascicular, block; (iii) Congenital long QT syndrome; (iv) Persistent or history of clinically meaningful ventricular arrhythmias or atrial fibrillation; (v) QTcF>460 msec on screening ECG (mean of triplicate recordings); (vi) Unstable angina pectoris or myocardial infarction ≤3 months prior to starting Compound 1; (vii) Other clinically significant heart disease such as congestive heart failure requiring treatment or uncontrolled hypertension (blood pressure ≥160/95 mmHg); (6) Diabetes mellitus on active treatment, or subjects with either of the following: (i) Fasting blood glucose (FBG)≥126 mg/dL (7.0 mmol/L), or (ii) HbA1c≥6.5%; (7) Other concurrent severe and/or uncontrolled concomitant medical conditions (eg, active or uncontrolled infection) that could cause unacceptable safety risks or compromise compliance with the protocol; (8) Prior systemic cancer-directed treatments or investigational modalities ≤5 half lives or 4 weeks, whichever is shorter, prior to starting study drug or who have not recovered from side effects of such therapy; (9) Major surgery ≤2 weeks prior to starting study drug or who have not recovered from side effects of such therapy. Subjects must have recovered from any effects of recent radiotherapy that might confound the safety evaluation of study drug. Autologous stem cell transplant ≤3 months prior to starting study drug; (10) Pregnancy or breastfeeding; (11) Adults of reproductive potential not employing two forms of birth control: (i) Females of childbearing potential must agree to use two adequate forms of contraception methods simultaneously (one must be non-hormonal) from the time of giving informed consent until 28 days after the last dose of Compound 1. Females of child-bearing potential, defined as sexually mature women who have not undergone a hysterectomy or bilateral oophorectomy, or who have not been naturally postmenopausal (ie, who have not menstruated at all) for >24 consecutive months and (ii) Males having partners who are female with child-bearing potential must agree that they and/or their partners will use at least two effective contraceptive methods (including one barrier method) when engaging in reproductive sexual activity throughout the study from the time of informed consent, and will avoid conceiving for 28 days after the last dose of Compound 1; (12) Known human immunodeficiency virus (HIV) infection; (13) Known chronic hepatitis B or C virus (HBV/HCV) infection, unless this is comorbidity in subjects with HCC; (14) Any significant medical condition, laboratory abnormality, or psychiatric illness that would prevent subjects from participating in the study, including the inability to swallow capsules in the absence of a gastric/jejunal feeding tube; (15) Any condition including the presence of laboratory abnormalities, which places subjects at unacceptable risk if they were to participate in the study; (16) Any condition that confounds the ability to interpret study data; and (17) Concurrent active second malignancy for which the subject is receiving therapy, excluding non-melanomatous skin cancer or carcinoma in situ of the cervix.

Subjects with hematologic malignancies or GBM are specifically excluded from participation, as are any subjects under 18 years of age.

Subjects will be assessed by phone or in the clinic 28±2 days after the last dose of Compound 1 to determine the status of any unresolved AEs and whether any new events occurred.

The Compound 1 plasma concentrations and PK parameters after administration of Treatments 1, 2 and 3 will be summarized using descriptive statistics. Plasma PK parameters will be calculated using non-compartmental methods and actual blood sampling times. Descriptive PK summary statistics (eg, N, mean, SD, CV %, geometric mean, geometric CV %, median, Min, and Max) will be presented as appropriate. Individual and mean concentration versus time profiles will be generated. Analyses of variance (ANOVA) will be performed on the natural log transformed $AUC_{0-t}$, $AUC_{0-\infty}$, and $C_{max}$ for Compound 1. The ANOVA model will include treatment (1, 2 or 3), sequence, and period as fixed effects, and subject nested within sequence as a random effect. The geometric mean ratios (treatment 2/1 and 3/2) and their 90% confidence intervals will be provided. For $T_{max}$ non-parametric analysis will be used to produce median differences.

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A method for treating a cancer, comprising administering to a patient having a cancer a crystal form of Compound 1

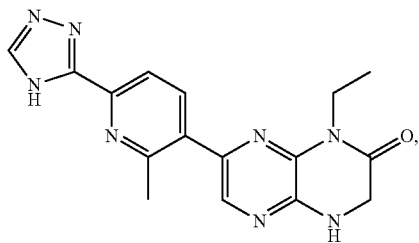

Compound 1 wherein the cancer is glioblastoma multiforme, head and neck squamous cell carcinoma, castration-resistant prostate cancer, Ewing's sarcoma, chronic lymphocytic leukemia or small lymphocytic lymphoma; and wherein the crystal form has an X-ray powder diffraction pattern comprising peaks
at 9.8, 12.0 and 17.9±0.2° 2θ;
at 7.5, 10.4 and 11.7±0.2° 2θ;
at 9.3, 11.7 and 19.9±0.2° 2θ;
at 11.0, 20.2 and 21.9±0.2° 2θ; or
at 9.3, 15.3 and 18.6±0.2° 2θ.

2. The method of claim 1, wherein the crystal form has an X-ray powder diffraction pattern comprising peaks at 9.8, 12.0 and 17.9±0.2° 2θ.

3. The method of claim 1, wherein the crystal form has an X-ray powder diffraction pattern comprising peaks at 7.5, 10.4 and 11.7±0.2° 2θ.

4. The method of claim 1, wherein the crystal form has an X-ray powder diffraction pattern comprising peaks at 9.3, 11.7 and 19.9±0.2° 2θ.

5. The method of claim 1, wherein the crystal form has an X-ray powder diffraction pattern comprising peaks at 11.0, 20.2 and 21.9±0.2° 2θ.

6. The method of claim 1, wherein the crystal form has an X-ray powder diffraction pattern comprising peaks at 9.3, 15.3 and 18.6±0.2° 2θ.

7. The method of claim 1, wherein the cancer is glioblastoma multiforme.

8. The method of claim 7, wherein the glioblastoma multiforme is characterized by O6-methylguanine-DNA methyltransferase (MGMT) methylation.

9. The method of claim 1, wherein the cancer is head and neck squamous cell carcinoma.

10. The method of claim 9, wherein the head and neck squamous cell carcinoma is characterized by deletion of chromosome 11q22 or loss of ataxia telangiectasia mutated (ATM) expression.

11. The method of claim 1, wherein the cancer is castration-resistant prostate cancer.

12. The method of claim 11, wherein the castration-resistant prostate cancer is E-twenty six (ETS) overexpressing castration-resistant prostate cancer.

13. The method of claim 1, wherein the cancer is Ewing's sarcoma.

14. The method of claim 13, wherein the Ewing's sarcoma is E-twenty six (ETS) overexpressing Ewings sarcoma.

15. The method of claim 1, wherein the cancer is chronic lymphocytic leukemia.

16. The method of claim 15, wherein the chronic lymphocytic leukemia is characterized by deletion of chromosome 11q22, loss of ataxia telangiectasia mutated (ATM) expression, mutation of IgVH, wild type IgVH, wild type p53/ATM, mutation of p53 or dysfunctional p53.

17. The method of claim 1, wherein the cancer is small lymphocytic lymphoma.

* * * * *